United States Patent
Lillaney et al.

(10) Patent No.: US 11,456,081 B1
(45) Date of Patent: Sep. 27, 2022

(54) SENSITIVE DRUG DISTRIBUTION SYSTEMS AND METHODS

(71) Applicant: Jazz Pharmaceuticals, Inc., Palo Alto, CA (US)

(72) Inventors: Prasheel Vashdev Lillaney, Redwood City, CA (US); Sherice Reneé Mills, San Carlos, CA (US); Gary Joseph Appio, Manahawkin, NJ (US)

(73) Assignee: Jazz Pharmaceuticals, Inc., Palo Alto, CA (US)

( * ) Notice: Subject to any disclaimer, the term of this patent is extended or adjusted under 35 U.S.C. 154(b) by 233 days.

(21) Appl. No.: 16/032,501

(22) Filed: Jul. 11, 2018

Related U.S. Application Data

(60) Provisional application No. 62/607,221, filed on Dec. 18, 2017, provisional application No. 62/534,892, filed on Jul. 20, 2017.

(51) Int. Cl.
*G16H 70/40* (2018.01)
*G16H 70/20* (2018.01)
*G16H 40/20* (2018.01)
*G16H 20/13* (2018.01)
*G16H 10/60* (2018.01)
*G16H 20/10* (2018.01)

(52) U.S. Cl.
CPC ............ *G16H 70/40* (2018.01); *G16H 10/60* (2018.01); *G16H 20/10* (2018.01); *G16H 20/13* (2018.01); *G16H 40/20* (2018.01); *G16H 70/20* (2018.01)

(58) Field of Classification Search
CPC ........ G16H 70/40; G16H 40/20; G16H 10/60; G16H 20/10; G16H 70/20; G16H 20/13
See application file for complete search history.

(56) References Cited

U.S. PATENT DOCUMENTS

| 3,556,342 A | 1/1971 | Guarr |
| 3,921,196 A | 11/1975 | Patterson |

(Continued)

FOREIGN PATENT DOCUMENTS

| EP | 0527027 A1 | 2/1993 | |
| WO | WO-2007036970 A1 * | 4/2007 | ............. G09B 5/065 |

OTHER PUBLICATIONS

RN.com, Age-Specific Considerations in Patient Care, Published Oct. 1, 2004, AMN Healthcare, Inc. (Year: 2004).*

(Continued)

*Primary Examiner* — Jonathan Durant
*Assistant Examiner* — Anne-Marie K Alderson
(74) *Attorney, Agent, or Firm* — Schwegman Lundberg & Woessner, P.A.

(57) ABSTRACT

A drug distribution system and method utilizes a central pharmacy and database to track all prescriptions for a sensitive drug. Information is kept in the database regarding all physicians allowed to prescribe the sensitive drug, and all patients receiving the drug. Abuses are identified by monitoring data in the database for prescription patterns by physicians and prescriptions obtained by patients and/or caregivers. Further verification is made that the physician is eligible to prescribe the drug by consulting a separate database, and optionally whether any actions are taken against the physician. Multiple controls beyond those for normal drugs are imposed on the distribution depending on the sensitivity of the drug.

15 Claims, 18 Drawing Sheets

(56) References Cited

U.S. PATENT DOCUMENTS

| | | | |
|---|---|---|---|
| 4,847,764 A | 7/1989 | Halvorson | |
| 4,976,351 A | 12/1990 | Mangini et al. | |
| 5,737,539 A | 4/1998 | Edelson et al. | |
| 5,845,255 A | 12/1998 | Mayaud | |
| 5,924,074 A | 7/1999 | Evans | |
| 5,963,919 A | 10/1999 | Brinkley et al. | |
| 6,021,392 A | 2/2000 | Lester et al. | |
| 6,045,501 A | 4/2000 | Elsayed et al. | |
| 6,055,507 A | 4/2000 | Cunningham | |
| 6,112,182 A | 8/2000 | Akers et al. | |
| 6,154,738 A | 11/2000 | Call | |
| 6,315,720 B1 | 11/2001 | Williams et al. | |
| 6,347,329 B1 | 2/2002 | Evans | |
| 6,561,977 B2 | 5/2003 | Williams et al. | |
| 6,564,121 B1 | 5/2003 | Wallace et al. | |
| 6,587,829 B1 | 7/2003 | Camarda et al. | |
| 6,687,676 B1 | 2/2004 | Denny | |
| 6,755,784 B2 | 6/2004 | Williams et al. | |
| 6,952,681 B2 | 10/2005 | McQuade et al. | |
| 7,058,584 B2 | 6/2006 | Kosinski et al. | |
| 7,519,540 B2 | 4/2009 | Mayaud | |
| 7,668,730 B2 | 2/2010 | Reardon et al. | |
| 7,765,106 B2 | 7/2010 | Dayton et al. | |
| 7,765,107 B2 | 7/2010 | Dayton et al. | |
| 7,797,171 B2 | 9/2010 | Reardan et al. | |
| 7,810,726 B2 | 10/2010 | De La Huerga | |
| 7,895,059 B2 | 2/2011 | Reardan et al. | |
| 8,457,988 B1 | 6/2013 | Reardan et al. | |
| 8,589,182 B1 | 11/2013 | Reardan et al. | |
| 8,731,963 B1 | 5/2014 | Reardan et al. | |
| 9,801,852 B2 | 10/2017 | Allphin | |
| 10,572,630 B1* | 2/2020 | Schmeling | G06Q 10/1093 |
| 2001/0001144 A1 | 5/2001 | Kapp | |
| 2001/0042050 A1 | 11/2001 | Fletcher et al. | |
| 2001/0047281 A1 | 11/2001 | Keresman, III et al. | |
| 2002/0010661 A1 | 1/2002 | Waddington et al. | |
| 2002/0032581 A1 | 3/2002 | Reitberg | |
| 2002/0032582 A1 | 3/2002 | Feeney, Jr. et al. | |
| 2002/0042725 A1 | 4/2002 | Mayaud | |
| 2002/0042762 A1 | 4/2002 | McQuade et al. | |
| 2002/0052762 A1 | 5/2002 | Kobylevsky et al. | |
| 2002/0111833 A1 | 8/2002 | Dick | |
| 2002/0143320 A1 | 10/2002 | Levin | |
| 2002/0161607 A1 | 10/2002 | Subich | |
| 2002/0177232 A1 | 11/2002 | Melker et al. | |
| 2003/0033168 A1 | 2/2003 | Califano et al. | |
| 2003/0046110 A1 | 3/2003 | Gogolak | |
| 2003/0050731 A1 | 3/2003 | Rosenblum | |
| 2003/0050802 A1 | 3/2003 | Jay et al. | |
| 2003/0050803 A1 | 3/2003 | Marchosky | |
| 2003/0074225 A1 | 4/2003 | Borsand et al. | |
| 2003/0093295 A1 | 5/2003 | Lilly et al. | |
| 2003/0110060 A1 | 6/2003 | Clementi | |
| 2003/0127508 A1 | 7/2003 | Jones | |
| 2003/0144876 A1 | 7/2003 | Kosinski et al. | |
| 2003/0160698 A1 | 8/2003 | Andreasson et al. | |
| 2003/0197366 A1 | 10/2003 | Kusterbeck | |
| 2003/0229519 A1 | 12/2003 | Eidex et al. | |
| 2003/0233256 A1 | 12/2003 | Cardenas et al. | |
| 2004/0008123 A1 | 1/2004 | Carrender et al. | |
| 2004/0019567 A1 | 1/2004 | Herceg et al. | |
| 2004/0019794 A1* | 1/2004 | Moradi | G06Q 50/22 |
| | | | 713/185 |
| 2004/0078237 A1 | 4/2004 | Kaafarani et al. | |
| 2004/0107117 A1 | 6/2004 | Denny | |
| 2004/0117126 A1 | 6/2004 | Fetterman et al. | |
| 2004/0122712 A1 | 6/2004 | Hill, Sr. et al. | |
| 2004/0122713 A1 | 6/2004 | Hill, Sr. et al. | |
| 2004/0162740 A1 | 8/2004 | Ericsson et al. | |
| 2004/0176985 A1 | 9/2004 | Lilly et al. | |
| 2005/0090425 A1 | 4/2005 | Reardan et al. | |
| 2005/0177398 A1* | 8/2005 | Watanabe | G16H 40/67 |
| | | | 705/3 |
| 2005/0216309 A1 | 9/2005 | Reardan et al. | |
| 2005/0222874 A1 | 10/2005 | Reardan et al. | |
| 2006/0062734 A1 | 3/2006 | Melker et al. | |
| 2010/0138237 A1* | 6/2010 | Reardan | G16H 20/10 |
| | | | 705/2 |
| 2010/0299158 A1 | 11/2010 | Siegel | |
| 2011/0119085 A1 | 5/2011 | Reardan et al. | |
| 2011/0145018 A1* | 6/2011 | Fotsch | G16H 15/00 |
| | | | 705/3 |
| 2012/0046970 A1 | 2/2012 | Potts et al. | |
| 2012/0065999 A1 | 3/2012 | Takatoku et al. | |
| 2012/0209623 A1 | 8/2012 | Reardan et al. | |
| 2012/0308973 A1* | 12/2012 | Marsac | A63H 3/02 |
| | | | 434/236 |
| 2012/0310670 A1* | 12/2012 | Pruitt | G16H 10/60 |
| | | | 705/3 |
| 2013/0226339 A1* | 8/2013 | Ervin | G16H 10/40 |
| | | | 700/240 |
| 2013/0332189 A1* | 12/2013 | Manning | G06Q 50/22 |
| | | | 705/2 |
| 2014/0074283 A1* | 3/2014 | Blackburn | G16H 20/13 |
| | | | 700/237 |
| 2014/0188504 A1 | 7/2014 | Reardan et al. | |
| 2014/0207480 A1 | 7/2014 | Reardan et al. | |
| 2014/0207481 A1 | 7/2014 | Reardan et al. | |
| 2014/0329213 A1* | 11/2014 | Ruman | G09B 19/0076 |
| | | | 434/236 |
| 2015/0202588 A1 | 7/2015 | Allphin | |
| 2016/0154947 A1 | 6/2016 | Reardan et al. | |
| 2016/0180058 A1 | 6/2016 | Reardan | |
| 2016/0184185 A1* | 6/2016 | Kim | G16H 20/13 |
| | | | 221/1 |
| 2016/0357924 A1* | 12/2016 | Jenkins | G06N 5/048 |
| 2017/0024547 A1* | 1/2017 | Bidani | G06F 16/248 |
| 2017/0326033 A1* | 11/2017 | Kraft | G16H 40/67 |
| 2021/0020317 A1 | 1/2021 | Lillaney et al. | |
| 2021/0295971 A1 | 9/2021 | Mills et al. | |

OTHER PUBLICATIONS

"2001 FDA Advisory Committees Meeting Documents by Center", U.S. Food and Drug Adminstration, [Online]. Retrieved from the Internet: <URL: http://www.fda.gov/ohrms/dockets/ac/01docsbc.htm>, (2001), 2 pgs.

"Advisory Commettees: CDER 2001 Meeting Documents", (2001), 16 pgs.

"Affidavit of Christopher Butler", [Online]. Retrieved from the Internet: <URL: http://web.archive.orwweb/20010309112600/http://www, fda.gov/ ohrms/dockets/ac/acmenu.htm>, (Jun. 15, 2012), 362 pgs.

"Amneal Pharmaceuticals LLC and Par Pharmaceutical, Inc.'s Exhibit List", Inter Partes Review of U.S. Pat. No. 7,765,106, (Jan. 8, 2015), 7 pgs.

"Amneal Pharmaceuticals LLC and Par Pharmaceutical, Inc.'s Exhibit List (Inter Partes Review of U.S. Pat. No. 7,765,107)", United States Patent and Trademark Office Before the Patent Trial and Appeal Board *Amneal Pharmaceuticals LLC and Par Pharmaceutical, Inc.* Petitioners v.*Jazz Pharmaceuticals, Inc.*Patent OwnerCase IPR: Unassigned U.S. Pat. No. 7,765,107, (Jan. 8, 2015), 7 pgs.

"Amneal Pharmaceuticals LLC and Par Pharmaceutical, Inc.'s Exhibit List (Inter Partes Review of U.S. Pat. No. 8,589,182)", United States Patent and Trademark Office Before the Patent Trial and Appeal Board *Amneal Pharmaceuticals LLC and Par Pharmaceutical, Inc.* Petitioners v.*Jazz Pharmaceuticals, Inc.*Patent Owner Case IPR: Unassigned U.S. Pat. No. 8,589,182, (Jan. 8, 2015), 7 pgs.

"Amneal Pharmaceuticals LLC's Power of Attorney", *Amneal Pharmaceuticals LLC and PAR Pharmaceutical, Inc.* v. *Jazz Pharmaceuticals, LLC*. Inter Partes Review of U.S. Pat. No. 7,765,106, (Jan. 7, 2015), 3 pgs.

"Amneal Pharmaceuticals, LLC's Power of Attorney", Amneal Pharmaceuticals, LLC's Power of Attorney for Inter Partes Review of U.S. Pat. No. 7,765,107, (Jan. 8, 2015), 3 pgs.

"Amneal Pharmaceuticals, LLC's Power of Attorney", *Amneal Pharmaceuticals, LLC, Par Pharmaceutical, Inc., and Roxane*

(56) References Cited

OTHER PUBLICATIONS

*Laboratories, Inc.* v. *Jazz Pharmaceuticals, Inc.* United States District Court, District of New Jersey, (Jun. 24, 2014), 3 pgs.
"Amneal Pharmaceuticals, LLC's Power of Attorney", *Amneal Pharmaceuticals, LLC, and Par Pharmaceutical, Inc.* v. *Jazz Pharmaceuticals, Inc.* United States District Court, District of New Jersey, (Jul. 7, 2014), 3 pgs.
"Amneal Pharmaceuticals, LLC's Power of Attorney", *Amneal Pharmaceuticals, LLC, and Par Pharmaceutical, Inc.* v. *Jazz Pharmaceuticals, Inc.* United States District Court, District of New Jersey, (Jul. 9, 2014), 3 pgs.
"Amneal Pharmaceuticals, LLC, Par Pharmaceutical, Inc., and Roxane Laboratories, Inc.'s Exhibit List (CBM Patent Review of U.S. Pat. No. 7,895,059)", *Amneal Pharmaceuticals, LLC, Par Pharmaceutical, Inc., and Roxane Laboratories, Inc.* v. *Jazz Pharmaceuticals, Inc.* United States District Court, District of New Jersey, (Jun. 24, 2014), 6 pgs.
"Amneal Pharmaceuticals, LLC, Par Pharmaceutical, Inc., and Roxane Laboratories, Inc.'s Exhibit List (CBM Patent Review of U.S. Pat. No. 8,457,988)", *Amneal Pharmaceuticals, LLC, and Par Pharmaceutical, Inc.* v. *Jazz Pharmaceuticals, Inc.* United States District Court, District of New Jersey, (Jul. 7, 2014), 6 pgs.
"Amneal Pharmaceuticals, LLC, Par Pharmaceutical, Inc., and Roxane Laboratories, Inc.'s Exhibit List (CBM Patent Review of U.S. Pat. No. 8,589,182)", *Amneal Pharmaceuticals, LLC, and Par Pharmaceutical, Inc.* v. *Jazz Pharmaceuticals, Inc.* United States District Court, District of New Jersey, (Jul. 9, 2014), 6 pgs.
"Amneal Pharmaceuticals, LLC's Power of Attorney", United States Patent and Trademark Office Before the Patent Trial and Appeal Board *Amneal Pharmaceuticals, LLC. and Par Pharmaceutical, Inc.* Petitioners v.*Jazz Pharmaceuticals, Inc.*Patent Owner Case CBM: Unassigned U.S. Pat. No. 8,457,988, (Jul. 7, 2014), 3 pgs.
"Amneal Pharmaceuticals, LLC's Power of Attorney", *Amneal Pharmaceuticals LLC and PAR Pharmaceutical, Inc.* Petitioners v. *Jazz Pharmaceuticals, LLC* U.S. Pat. No. 8,589,182, (Jan. 8, 2015), 3 pgs.
"Amneal Pharmaceuticals, LLC's Power of Attorney for Inter Partes Review of U.S. Pat. No. 8,731,963", *Amneal Pharmaceuticals LLC and Par Pharmaceutical, Inc.* v. *Jazz Pharmaceuticals, Inc.* Case IPR: Unassigned, 4 pgs.
"An Interview with Orphan Medical about Xyrem", http://www.talkaboutsleep.com/sleepdisorders/archives/Narcolepsy_xyrem_interview.htm, (Feb. 12, 2001), 3 pgs.
"Answer, Defenses, and Counterclaims", *Jazz Pharmaceuticals, Inc.* v. *Amneal Pharmaceuticals, LLC*, (United States District Court, District of New Jersey Civil Action No. 13-391 ES-SCM, (Apr. 15, 2013), 22 pgs.
"U.S. Appl. No. 10/322,348, Advisory Action dated Feb. 5, 2007", 3 pgs.
"U.S. Appl. No. 10/322,348, Appeal Brief filed May 21, 2007", 32 pgs.
"U.S. Appl. No. 10/322,348, Appeal Brief filed Jul. 18, 2007", 32 pgs.
"U.S. Appl. No. 10/322,348, Examiner Interview Summary dated Oct. 21, 2009", 3 pgs.
"U.S. Appl. No. 10/322,348, Final Office Action dated Oct. 18, 2006", 14 pgs.
"U.S. Appl. No. 10/322,348, Final Office Action dated Dec. 29, 2005", 11 pgs.
"U.S. Appl. No. 10/322,348, Non Final Office Action dated Jun. 17, 2005", 26 pgs.
"U.S. Appl. No. 10/322,348, Non Final Office Action dated Jun. 19, 2006", 18 pgs.
"U.S. Appl. No. 10/322,348, Non Final Office Action dated Jun. 29, 2005", 12 pgs.
"U.S. Appl. No. 10/322,348, Notice of Allowance dated Dec. 31, 2009", 16 pgs.
"U.S. Appl. No. 10/322,348, Notice of Non-Complaint Appeal Brief mailed Jun. 28, 2007", 2 pqs.
"U.S. Appl. No. 10/322,348, Preliminary Amendment dated Sep. 30, 2004", 11 pgs.
"U.S. Appl. No. 10/322,348, Reply Brief filed Dec. 3, 2007", 4 pgs.
"U.S. Appl. No. 10/322,348, Response filed Jan. 17, 2007 to Final Office Action dated Oct. 18, 2006", 17 pgs.
"U.S. Appl. No. 10/322,348, Response filed Mar. 29, 2006 to Final Office Action dated Dec. 29, 2005", 11 pgs.
"U.S. Appl. No. 10/322,348, Response filed Aug. 8, 2006 to Non Final Office Action dated Jun. 19, 2006", 10 pgs.
"U.S. Appl. No. 10/322,348, Response filed Sep. 29, 2005 to Non Final Office Action dated Jun. 29, 2005", 19 pgs.
"U.S. Appl. No. 10/322,348, Response filed Nov. 2, 2009 to Final Office Action dated Oct. 18, 2006 and Advisory Action dated Feb. 5, 2007", 16 pgs.
"U.S. Appl. No. 10/731,915, Non Final Office Action dated Aug. 12, 2005", 22 pgs.
"U.S. Appl. No. 10/731,915, Non Final Office Action dated Oct. 5, 2004", 21 pgs.
"U.S. Appl. No. 10/731,915, Response filed Feb. 2, 2005 to Non Final Office Action mailed", 17 pgs.
"U.S. Appl. No. 10/979,665, Non-Final Office Action dated Nov. 17, 2009", 19 pgs.
"U.S. Appl. No. 10/979,665, Notice of Allowance dated Apr. 30, 2010", 8 pgs.
"U.S. Appl. No. 10/979,665, Preliminary Amendment filed Jun. 22, 2006", 7 pgs.
"U.S. Appl. No. 10/979,665, Preliminary Amendment dated Nov. 2, 2004", 3 pgs.
"U.S. Appl. No. 10/979,665, Response filed Mar. 11, 2010 to Non Final Office Action dated Nov. 17, 2009", 13 pgs.
"U.S. Appl. No. 10/979,665, Response filed Jul. 14, 2009 to Restriction Requirement dated Jun. 25, 2009", 8 pgs.
"U.S. Appl. No. 10/979,665, Restriction Requirement dated Jun. 25, 2009", 7 pgs.
"U.S. Appl. No. 11/097,651, Examiner Interview Summary dated May 27, 2010", 3 pgs.
"U.S. Appl. No. 11/097,651, Final Office Action dated Nov. 12, 2009", 14 pgs.
"U.S. Appl. No. 11/097,651, Non-Final Office Action dated Mar. 3, 2010", 19 pgs.
"U.S. Appl. No. 11/097,651, Non-Final Office Action dated May 29, 2009", 21 pgs.
"U.S. Appl. No. 11/097,651, Notice of Allowance dated Jul. 23, 2010", 9 pgs.
"U.S. Appl. No. 11/097,651, Preliminary Amendment dated Apr. 1, 2005", 6 pgs.
"U.S. Appl. No. 11/097,651, Response filed Feb. 9, 2010 to Final Office Action dated Nov. 12, 2009", 11 pgs.
"U.S. Appl. No. 11/097,651, Response filed Jun. 3, 2010 to Non Final Office Action dated Mar. 3, 2010", 12 pgs.
"U.S. Appl. No. 11/097,651, Response filed Sep. 17, 2009 to Non Final Office Action dated May 29, 2009", 10 pgs.
"U.S. Appl. No. 11/097,985, Non Final Office Action dated Sep. 14, 2009", 22 pgs.
"U.S. Appl. No. 11/097,985, Notice of Allowance dated Mar. 10, 2010", 11 pgs.
"U.S. Appl. No. 11/097,985, Preliminary Amendment dated Apr. 1, 2005", 7 pgs.
"U.S. Appl. No. 11/097,985, Response filed Nov. 3, 2009 to Non Final Office Action dated Sep. 14, 2009", 15 pgs.
"U.S. Appl. No. 11/097,985, Supplemental Notice of Allowability dated Jun. 29, 2010", 3 pgs.
"U.S. Appl. No. 12/704,097, Non-Final Office Action dated Sep. 24, 2010", 5 pgs.
"U.S. Appl. No. 12/704,097, Notice of Allowance dated Dec. 21, 2010", 8 pgs.
"U.S. Appl. No. 12/704,097, Response filed Nov. 4, 2010 to Non Final Office Action dated Sep. 24, 2010", 12 pgs.
"U.S. Appl. No. 13/013,680, Response filed Jun. 12, 2012 to Restriction Requirement dated Dec. 14, 2011", 9 pgs.
"U.S. Appl. No. 13/013,680, Restriction Requirement dated Dec. 14, 2011", 7 pgs.

(56) References Cited

OTHER PUBLICATIONS

"U.S. Appl. No. 13/592,202 , Response filed Jul. 25, 2013 to Non Final Office Action dated Jun. 5, 2013", 15 pgs.
"U.S. Appl. No. 13/592,202, Examiner Interview Summary dated Jul. 9, 2013", 3 pgs.
"U.S. Appl. No. 13/592,202, Final Office Action dated Oct. 31, 2013", 18 pgs.
"U.S. Appl. No. 13/592,202, Non Final Office Action dated Jun. 5, 2013", 14 pgs.
"U.S. Appl. No. 13/592,202, Notice of Allowance dated Jan. 15, 2014", 5 pgs.
"U.S. Appl. No. 13/592,202, Notice of Allowance dated Mar. 14, 2014", 5 pgs.
"U.S. Appl. No. 13/592,202, Response filed Feb. 15, 2013 to Restriction Requirement dated Jan. 16, 2013", 8 pgs.
"U.S. Appl. No. 13/592,202, Response filed Dec. 31, 2013 to Final Office Action dated Oct. 31, 2013", 11 pgs.
"U.S. Appl. No. 13/592,202, Restriction Requirement dated Jan. 16, 2013", 6 pgs.
"U.S. Appl. No. 13/595,676 , Response filed May 31, 2013 to Non Final Office Action dated Mar. 21, 2013", 14 pgs.
"U.S. Appl. No. 13/595,676, Examiner Interview Summary dated May 30, 2013", 3 pgs.
"U.S. Appl. No. 13/595,676, Non Final Office Action dated Mar. 21, 2013", 16 pgs.
"U.S. Appl. No. 13/595,676, Notice of Allowance dated Sep. 17, 2013", 6 pgs.
"U.S. Appl. No. 13/595,757, Examiner Interview Summary dated Mar. 12, 2013", 3 pgs.
"U.S. Appl. No. 13/595,757, Non Final Office Action dated Jan. 17, 2013", 6 pgs.
"U.S. Appl. No. 13/595,757, Notice of Allowance dated Mar. 21, 2013", 68 pgs.
"U.S. Appl. No. 13/595,757, Response filed Mar. 7, 2013 to Non Final Office Action dated Jan. 17, 2013", 8 pgs.
"U.S. Appl. No. 14/196,603, Examiner Interview Summary dated Mar. 3, 2015", 3 pgs.
"U.S. Appl. No. 14/196,603, Final Office Action dated Jul. 14, 2014", 6 pgs.
"U.S. Appl. No. 14/196,603, Final Office Action dated Aug. 6, 2015", 9 pgs.
"U.S. Appl. No. 14/196,603, Non Final Office Action dated Apr. 18, 2014", 8 pgs.
"U.S. Appl. No. 14/196,603, Non Final Office Action dated Dec. 17, 2014", 6 pgs.
"U.S. Appl. No. 14/196,603, Preliminary Amendment filed Mar. 11, 2014", 10 pgs.
"U.S. Appl. No. 14/196,603, Response filed Apr. 14, 2014 to Non Final Office Action dated Dec. 17, 2014", 22 pgs.
"U.S. Appl. No. 14/196,603, Response filed May 20, 2014 to Non Final Office Action dated Apr. 18, 2014", 11 pgs.
"U.S. Appl. No. 14/196,603, Response filed Nov. 6, 2014 to Final Office Action dated Jul. 14, 2014", 16 pgs.
"U.S. Appl. No. 14/196,603, Response filed Apr. 16, 2015 to Non Final Office Action dated Dec. 17, 2014", 22 pgs.
"U.S. Appl. No. 14/219,904, Final Office Action dated Oct. 16, 2015", 20 pgs.
"U.S. Appl. No. 14/219,904, Non Final Office Action dated Mar. 2, 2015", 19 pgs.
"U.S. Appl. No. 14/219,904, Non Final Office Action dated May 6, 2014", 16 pgs.
"U.S. Appl. No. 14/219,904, Preliminary Amendment filed Mar. 20, 2014", 9 pgs.
"U.S. Appl. No. 14/219,904, Response filed Nov. 3, 2014 to Non Final Office Action dated May 6, 2014", 14 pgs.
"U.S. Appl. No. 14/219,941, Final Office Action dated Sep. 3, 2015", 17 pgs.
"U.S. Appl. No. 14/219,941, Non Final Office Action dated Feb. 23, 2015", 16 pgs.

"U.S. Appl. No. 14/219,941, Non Final Office Action dated May 2, 2014", 16 pgs.
"U.S. Appl. No. 14/219,941, Preliminary Amendment filed Mar. 20, 2014", 12 pgs.
"U.S. Appl. No. 14/219,941, Response filed Jun. 5, 2015 to Non Final Office Action dated Feb. 23, 2015", 21 pgs.
"U.S. Appl. No. 14/219,941,Response filed Oct. 31, 2014 to Non Final Office Action dated May 2, 2014", 15 pgs.
"U.S. Appl. No. 15/014,831, Preliminary Amendment filed Feb. 4, 2016", 11 pgs.
"U.S. Appl. No. 15/057,898, Preliminary Amendment filed Mar. 3, 2016", 18 pgs.
"U.S. Appl. No. 13/013,680, Preliminary Amendment filed Jun. 13, 2012", 4 pgs.
"U.S. Appl. No. 14/219,904, Response dated Jul. 8, 2015 to Non-Final Office Action filed Mar. 2, 2015", 19 pgs.
"Approved Labeling for Xyrem. Application No. 21-196", Center for Drug Evaluation and Research, (Jul. 17, 2002), 48 pgs.
"Ascent Pharmaceutical ANDA filing", Part 1, (Jun. 13, 2017), 44 pgs.
"Ascent Pharmaceutical ANDA filing", Part 2, (Jun. 13, 2017), 53 pgs.
"Briefing Booklet for the Peripheral and Central Nervous System Drugs Advisory Committee Meeting", Orphan Medical, Inc., (Jun. 6, 2001), 353 pgs.
"CDER 2001 Advisory Committee Meeting Documents", [Online]. Retrieved from the Internet: <URL: https://web.archive.org/web/20011004081740/http://www.fda.gov/ohrms/dockets/ac/cder01.htm>, (Oct. 4, 2001), 11 pgs.
"CDER 2001 Meeting Documents", [Online]. Retrieved from the Internet: <URL: https://web.archive.org/web/20010617210030/http://www.fda.gov/ohrms/dockets/ac/cder01.htm>, (Jun. 17, 2001), 7 pgs.
"Certified File History for U.S. Pat. No. 7,895,059", IPR of U.S. Pat. No. 7,895,059, (Jan. 14, 2014), 818 pgs.
"Civil Action No. 2: 13-cv-00391-ES-JAD (consolidated)", Defendant Par Pharmaceutical, Inc.'s Amended Invalidity Contentions (United States District Court of New Jersey), (Jun. 10, 2014), 64 pgs.
"Civil Action No. 2:13-cv-00391-ES-SCM (consolidated)", Defendant Amneal Pharmaceuticals, LLC's Preliminary Invalidity Contentions (United States District Court of New Jersey), (Nov. 7, 2013), 182 pgs.
"Civil Cover Sheet", *Jazz Pharmaceuticals, Inc. v. Amneal Pharmaceuticals, LLC*, (United States District Court, District of New Jersey), (Sep. 12, 2013), 2 pgs.
"Civil Cover Sheet", *Jazz Pharmaceuticals, Inc. v. Par Pharmaceuticals, Inc.*, (United States District Court, District of New Jersey), Case 2:13-cv-07884-ES-JAD, (Dec. 27, 2013), 1 pg.
"Civil Cover Sheet", *Jazz Pharmaceuticals, Inc. v. Amneal Pharmaceuticals, LLC*, (United States District Court, District of New Jersey), (Jan. 18, 2013), 2 pgs.
"Civil Docket", *Jazz Pharmaceuticals, Inc. v. Roxane Laboratories, Inc.*, (United States District Court, District of New Jersey Civil Action No. 2:10-CV-06108-ES-CLW), (Nov. 22, 2010), 15 pgs.
"Complaint for Patent Infringement", *Jazz Pharmaceuticals, Inc. v. Amneal Pharmaceuticals, LLC*, (United States District Court, District of New Jersey), (Jan. 18, 2013), 17 pgs.
"Complaint for Patent Infringement", *Jazz Pharmaceuticals, Inc. v. Par Pharmaceuticals, Inc*, (United States District Court, District of New Jersey), Case 2:13-cv-07884-ES-JAD, (Dec. 27, 2013), 26 pgs.
"Complaint for Patent Infringement", *Jazz Pharmaceuticals, Inc. v. Roxane Laboratories, Inc.*, (United States District Court, District of New Jersey Civil Action No. 10-6108 (ES-CLW), (Nov. 22, 2010), 14 pgs.
"Complaint for Patent Infringement", *Jazz Pharmaceuticals, Inc. and Jazz Pharmaceuticals Ireland Ltd., v. Watson Laboratories, Inc.*, (United States District Court, District of New Jersey, (Dec. 11, 2014), 30 pgs.
"Complaint for Patent Infringement Exhibit 1025 for CBM Patent U.S. Pat. No. 7,895,059", *Jazz Pharmaceuticals, Inc. v. Roxane Laboratories, Inc.*, (United States District Court, District of New Jersey Civil Action No. 2:11-CV-02523-ES-MCA), (May 2, 2011), 36 pgs.

(56) References Cited

OTHER PUBLICATIONS

"Complaint for Patent Infringement Part 1 of Exhibit 1025 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", *Jazz Pharmaceuticals, Inc.* v. *Par Pharmaceuticals, Inc,* (United States District Court, District of New Jersey, Civil Action No. 2:13-CV-07884-ES-JAD), 116 pgs.

"Complaint for Patent Infringement Part 1 of Exhibit 1026 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", *Jazz Pharmaceuticals, Inc.* v. *Par Pharmaceuticals, Inc,* (United States District Court, District of New Jersey, Civil Action No. 2:13-CV-07884-ES-JAD), 116 pgs.

"Complaint for Patent Infringement Part. 2 of Exhibit 1025 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", 116 pgs.

"Complaint for Patent Infringement Part 2 of Exhibit 1026 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", *Jazz Pharmaceuticals, Inc.* v. *Par Pharmaceuticals, Inc,* (United States District Court, District of New Jersey, Civil Action No. 2:13-CV-07884-ES-JAD), 116 pgs.

"Complaint for Patent Infringement Part 3 of Exhibit 1025 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", 116 pgs.

"Complaint for Patent Infringement Part 3 of Exhibit 1026 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", *Jazz Pharmaceuticals, Inc.* v. *Par Pharmaceuticals, Inc,* (United States District Court, District of New Jersey, Civil Action No. 2:13-CV-07884-ES-JAD), 116 pgs.

"Complaint for Patent Infringement Part 4 of Exhibit 1024 for CBM Patents: U.S. Pat. No. 6,780,889, U.S. Pat. No. 7,262,219, U.S. Pat. No. 7,668,730, U.S. Pat. No. 7,765,106, and U.S. Pat. No. 7,765,107", *Jazz Pharmaceuticals, Inc.* v. *Roxane Laboratories, Inc,* (United States District Court, District of New Jersey, Civil Action No. 2:10-CV-06108-SDW-MCA, 174 pgs.

"Complaint for Patent Infringement Part 4 of Exhibit 1025 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", 116 pgs.

"Complaint for Patent Infringement Part 4 of Exhibit 1026 for CBM Patents: U.S. Pat. No. 6,472,431, U.S. Pat. No. 6,780,889, U.S. Pat. No. 7,262,219, U.S. Pat. No. 7,851,506, U.S. Pat. No. 8,263,650, U.S. Pat. No. 8,324,275, U.S. Pat. No. 8,461,203, U.S. Pat. No. 7,668,730, U.S. Pat. No. 7,765,106, U.S. Pat. No. 7,765,107, U.S. Pat. No. 7,895,059, U.S. Pat. No. 8,457,988, and U.S. Pat. No. 8,589,182", *Jazz Pharmaceuticals, Inc.* v. *Par Pharmaceuticals, Inc,* (United States District Court, District of New Jersey, Civil Action No. 2:13-CV-07884-ES-JAD), 116 pgs.

"Complaint for Patent Infringement with Exhibits A & B", *Jazz Pharmaceuticals, Inc.* v. *Amneal Pharmaceuticals, LLC,* (United States District Court, District of New Jersey), (Sep. 12, 2013), 76 pgs.

"Controlled Substances Act", Drugs of Abuse, U.S. Department of Justice, Drug Enforcement Administration, (1997), 9 pgs.

"Dayton Reardan, Exhibit 1011", LinkedIn, [Online]. Retrieved from the Internet: <URL: https://www.linkedin.com/pub/dayton-reardan/12/18/475[03/09/2015 3:22:23 PM]>, (Accessed Mar. 9, 2015), 3 pgs.

"Decision Denying Patent Owner's Request for Rehearing 37 C.F.R. § 42.71(d)", United States Patent and Trademark Office Before the Patent Trial and Appeal Board *Par Pharmaceutical, Inc. and Amneal Pharmaceuticals LLC,* v. *Jazz Pharmaceuticals, Inc.*, IPR2015-00551 U.S. Pat. No. 8,457,988 B1, (Dec. 22, 2016), 10 pgs.

"Decision Denying Patent Owner's Request for Rehearing 37 C.F.R. § 42.71(d)", United States Patent and Trademark Office Before the Patent Trial and Appeal Board *Par Pharmaceutical, Inc. and Amneal Pharmaceuticals LLC,* v. *Jazz Pharmaceuticals, Inc.*, IPR2015-00546 U.S. Pat. No. 7,765,106 B2, (Dec. 22, 2016), 8 pgs.

"Decision for Institution of Inter Partes Review 37 C.F.R. § 42.108 of U.S. Pat. No. 7,765,106", *Par Pharmaceutical, Inc. and Amneal Pharmaceuticals LLC* v. *Jazz Pharmaceuticals, Inc.*, (Jul. 28, 2015), 43 pgs.

"Decision for Institution of Inter Partes Review 37 C.F.R. § 42.108 of U.S. Pat. No. 7,765,107", *Par Pharmaceutical, Inc. and Amneal Pharmaceuticals LLC* v. *Jazz Pharmaceuticals, Inc.*, (Jul. 28, 2015), 42 pgs.

"Decision for Institution of Inter Partes Review 37 C.F.R. § 42.108 of U.S. Pat. No. 8,457,988 and U.S. Pat. No. 7,668,730", *Par Pharmaceutical, Inc. and Amneal Pharmaceuticals LLC* v. *Jazz Pharmaceuticals, Inc.*, (Jul. 28, 2015), 47 pgs.

"Decision for Institution of Inter Partes Review 37 C.F.R. § 42.108 of U.S. Pat. No. 8,731,963 B1", *Amneal Pharmaceuticals LLC and Par Pharmaceutical, Inc.* v. *Jazz Pharmaceuticals, Inc.* Case IPR2015-01903, 25 pgs.

"Declaration by Dr. Jeffrey Fudin, Regarding U.S. Pat. No. 7,895,059 Under 37 C.F.R. § 42.63(a) Exhibit 1006", *Coalition for Affordable Drugs III LLC* v. *Jazz Pharmaceuticals, Inc.* United States District Court, District of New Jersey, (Apr. 6, 2015), 151 pgs.

"Declaration of Robert J. Valuck, Ph.D, R. Ph.", *Amneal Pharmaceuticals, LLC, and Par Pharmaceutical, Inc,* v. *Jazz Pharmaceuticals, Inc.* United States District Court, District of New Jersey Covered Business Method Patent Review of U.S. Pat. No. 8,457,988, (Jul. 6, 2014), 121 pgs.

"Declaration of Robert J. Valuck, Ph.D, R. Ph.", *Amneal Pharmaceuticals, LLC, Par Pharmaceutical, Inc., and Roxane Laboratories, Inc.* v. *Jazz Pharmaceuticals, Inc.* United States District Court, District of New Jersey, (Jun. 23, 2014), 93 pgs.

"Declaration of Robert J. Valuck, Ph.D, R. Ph. (for CBM Patent Review of U.S. Pat. No. 7,668,730)", *Par Pharmaceutical, Inc. and Roxane Laboratories, Inc.* v. *Jazz Pharmaceuticals, Inc.* United States District Court, District of New Jersey, (Jul. 8, 2014), 87 pgs.

"Declaration of Robert J. Valuck, Ph.D, R. Ph. (for CBM Patent Review of U.S. Pat. No. 7,765,106)", *Roxane Laboratories, Inc. and Par Pharmaceutical, Inc.* v. *Jazz Pharmaceuticals, Inc.* United States District Court, District of New Jersey, (Jul. 28, 2014), 117 pgs.

"Declaration of Robert J. Valuck, Ph.D, R. Ph. (for CBM Patent Review of U.S. Pat. No. 8,589,182)", *Amneal Pharmaceuticals, LLC, and Par Pharmaceutical, Inc.* v. *Jazz Pharmaceuticals, Inc.* United States District Court, District of New Jersey, (Jul. 8, 2014), 84 pgs.

"Declaration of Robert J. Valuck, Ph.D., R.Ph", *Amneal Pharmaceuticals, LLC, and Par Pharmaceutical, Inc.* v. *Jazz Pharmaceuticals, Inc.*—Inter Partes Review of U.S. Pat. No. 7,765,106 (Exhibit 1007), (Jan. 8, 2015), 202 pgs.

"Declaration of Robert J. Valuck, Ph.D., R.Ph.", United States Patent and Trademark Office Before the Patent Trial and Appeal

(56) References Cited

OTHER PUBLICATIONS

Board *Par Pharmaceutical, Inc*.Petitioner v.*Jazz Pharmaceuticals, Inc*. Patent Owner U.S. Pat. No. 7,895,059, (Jan. 7, 2015), 137 pgs.
"Declaration of Robert J. Valuck, Ph.D., R.Ph.", United States Patent and Trademark Office Before the Patent Trial and Appeal Board *Par Pharmaceutical, Inc.*, Petitioner v. *Jazz Pharmaceuticals, Inc*.Patent Owner Case IPR: Unassigned U.S. Pat. No. 8,457,988, (Jan. 7, 2015), 173 pgs.
"Declaration of Robert J. Valuck, Ph.D., R.Ph.", *Amneal Pharmaceuticals LLC and Par Pharmaceutical, Inc*. Petitioners v.*Jazz Pharmaceuticals, Inc*. Patent Owner, (Jan. 8, 2015), 202 pgs.
"Declaration of Robert J. Valuck, Ph.D., R.Ph.", United States Patent and Trademark Office Before the Patent Trial and Appeal Board *Amneal Pharmaceuticals LLC and Par Pharmaceutical, Inc.*, Petitioners v.*Jazz Pharmaceuticals, Inc*.Patent Owner Case IPR: Unassigned, (Jan. 8, 2015), 150 pgs.
"Declaration of Robert J. Valuck, Ph.D., R.Ph.U.S. Pat. No. 7,668,730", *Amneal Pharmaceuticals, LLC, and Par Pharmaceutical, Inc*, v. *Jazz Pharmaceuticals, Inc.*, (Jan. 7, 2015), 129 pgs.
"Detailed Factual and Legal Basis of Non-Infringement and/or Invalidity", Amneal Pharmaceuticals, LLC, (Dec. 12, 2012), 3 pgs.
"Detailed Factual and Legal Basis of Non-Infringement and/or Invalidity", Amneal Pharmaceuticals, LLC, (Dec. 7, 2012), 6 pgs.
"Diversion Prevention Through Responsible Distribution", NADDI Regional Training, (May 2001), 12 pages.
"Diversion Prevention Through Responsible Distribution", NADDI Regional Training Tennessee, (Jun. 2001), 14 Pages.
"Diversion Prevention Through Responsible Distribution", NADDI National Conference, (Nov. 2001), 15 pages.
"Email accepting service of complaint Civil Action No. 13-7884", (Jan. 13, 2014), 2 pgs.
"Exhibits A-D", *Jazz Pharmaceuticals v Amneal Pharmaceuticals, LLC*, (Jan. 18, 2013), 151 pgs.
"Exhibits D-G", *Jazz Pharmaceuticals v Amneal Pharmaceuticals, LLC*, (Jan. 18, 2013), 123 pgs.
"Fed. R. Civ. P. Rule 7.1 Disclosure Statement", *Jazz Pharmaceuticals, Inc. v. Amneal Pharmaceuticals, LLC*, (United States District Court, District of New Jersey), (Sep. 12, 2013), 2 pgs.
"Fed. R. Civ. P. Rule 7.1 Disclosure Statement", *Jazz Pharmaceuticals, Inc. v. Amneal Pharmaceuticals, LLC*, (United States District Court, District of New Jersey), (Jan. 18, 2013), 2 pgs.
"Fed. R. Civ. P. Rule 7.1 Disclosure Statement", *Jazz Pharmaceuticals, Inc, v. Par Pharmaceuticals, Inc.*, (United States District Court, District of New Jersey), Case 2:13-cv-07884-ES-JAD, (Dec. 27, 2013), 2 pgs.
"File History for U.S. Pat. No. 7,765,107", AMN1002 IPR of U.S. Pat. No. 7,765,107, (Jul. 27, 2010), 309 pgs.
"File History for U.S. Pat. No. 8,589,182", (May 20, 2014), 210 pgs.
"Final Minutes: Peripheral and Central Nervous System Drugs Advisory Committee", [Online]. Retrieved from the Internet: <URL: http://www.fda.gov/ohrms/dockets/ac/01/minutes/3754m1.htm>, (Jun. 6, 2001), 6 pgs.
"Final Written Decision 35 U.S.C. § 318(a) and 37 C.F.R. § 42.73 for U.S. Pat. No. 8,731,963 B1", *Amneal Pharmaceuticals, LLC and Par Pharmaceutical, Inc, v. Jazz Pharmaceuticals, Inc.*, Case IPR2015-01903, (Mar. 22, 2017), 36 pgs.
"Final Written Decision for Inter Partes Review of U.S. Pat. No. 7,765,106 B2", Inter Partes Review Case No. IPR2015-00546 Before Jacqueline Wright Bonilla, Brian P. Murphy, and Jon B. Tornquist,, (Jul. 27, 2016), 54 pgs.
"Final Written Decision for Inter Partes Review of U.S. Pat. No. 7,765,107 B2", Inter Partes Review Case No. IPR2015-00547 Before Jacqueline Wright Bonilla, Brian P. Murphy, and Jon B. Tornquist,, (Jul. 27, 2016), 55 pgs.
"Final Written Decision for Inter Partes Review of U.S. Pat. No. 7,895,059 B2", Inter Partes Review Case No. IPR2015-00548 Before Jacqueline Wright Bonilla, Brian P. Murphy, and Jon B. Tornquist, (Jul. 27, 2016), 60 pgs.
"Final Written Decision for Inter Partes Review of U.S. Pat. No. 8,457,988 B1 and U.S. Pat. No. 7,668,730 B2", Inter Partes Review Case No. IPR2015-00551, IPR2015-00554 Before Jacqueline Wright Bonilla, Brian P. Murphy, and Jon B. Tornquist,, (Jul. 27, 2016), 63 pgs.
"Final Written Decision for Inter Partes Review of U.S. Pat. No. 8,589,182 B1", Inter Partes Review Case No. IPR2015-00545 Before Jacqueline Wright Bonilla, Brian P. Murphy, and Jon B. Tornquist,, (Jul. 27, 2016), 49 pgs.
"Inter Partes Review of U.S. Pat. No. 8,731,963 Par and Amneal Exhibit List", *Amneal Pharmaceuticals LLC and Par Pharmaceutical, Inc. v. Jazz Pharmaceuticals, Inc*. Case IPR: Unassigned, 7 pgs.
"Jazz Pharmaceuticals, Inc.'s Opening Markman Brief", *Jazz Pharmaceuticals, Inc. v. Roxane Laboratories, Inc.*, United States District Court, District of New Jersey Civil Action No. 10-6108 (ES) (CLW), (Dec. 5, 2011), 34 pgs.
"Jazz Pharmaceuticals, Inc.'s Responsive Markman Brief", *Jazz Pharmaceuticals, Inc. v. Roxane Laboratories, Inc.*, (United States District Court, District of New JerseyCivil Action No. 10-6108 (ES) (CLW)), (Feb. 21, 2012), 41 pgs.
"Joint Claim Construction and Prehearing Statement", *Jazz Pharmaceuticals, Inc. v. Roxane Laboratories, Inc.*, (United States District Court, District of New Jersey Civil Action No. 10-6108 (ES) (CLW)), (Oct. 21, 2011), 31 pgs.
"Letter dated Jun. 3, 2014 from Kathryn Jones, Esq. ( IP Counsel Ranbaxy Inc.) to Suzanne Sawochka Hooper (Jazz Pharmaceuticals) and Bruce C. Cozadd (Jazz Pharmaceuticals) with Attachments A & B", Re: Notice of Paragraph IV Certification. Re: NDA 021196 Xyrem® Sodium Oxybate 500 mg/mL Oral Sol. w/ respect to U.S. Pat. Nos.: 6,780,889; 7,262,219; 7,668,730; 7,765,106; 7,765,107; 7,851,506; 7,895,059; 8,263,650; 8,324,275; 8,457,988; & 8,589,182, (Jun. 3, 2014), 84 pgs.
"Letter dated Jun. 6, 2014 from Kathryn Jones, Esq. ( IP Counsel Ranbaxy Inc.) to Suzanne Sawochka Hooper (Jazz Pharmaceuticals) and Bruce C. Cozadd (Jazz: Pharmaceuticals)", Re: Notice of Paragraph IV Certification. Re: NDA 021196 Xyrem® Sodium Oxybate 500 mg/mL Oral Sol. w/ respect to U.S. Pat. Nos. 6,780,889; 7,262,219; 7,668,730; 7,765,106; 7,765,107; 7,851,506; 7,895,059; 8,263,650; 8,324,275; 8,457,988; 8,589,182, 8,731,963, (Jun. 6, 2014), 3 pgs.
"Letter dated Jul. 3, 2014 from Michelle Bonomi-Huvala (Senior VP Corporate Regulatory Affairs for Par Pharmaceutical, Inc.) to Jazz Pharmaceuticals, Inc.", Re: Sodium Oxybate 500 mg/ml Oral Solution (XYREM®) U.S. Pat. No. 8,731,963, Notice of Paragragh IV Certification, (Jul. 3, 2014), 50 pgs.
"Letter dated Oct. 14, 2010 from Randall S. Wilson (Roxane Labs) to Bruce C. Cozadd (Jazz Pharmaceuticals)", Re: Patent Notice Pursuant to Section 505(b)(3)(B) [21 USC Sec. 355(b)(3)(B)], (Oct. 14, 2010), 11 pgs.
"Letter from Theodora McCormick to Magistrate Judge Cathy L. Waldor", (w/ Exhibits), (Feb. 27, 2012), 60 pgs.
"Letter from Theodora McCormick to Magistrate Judge Cathy L. Waldor", (w/ Exhibits), (Mar. 19, 2012), 104 pgs.
"Letter from Theodora McCormick to Magistrate Judge Cathy L. Waldor", (Mar. 29, 2012), 4 pgs.
"Letter from Wockhardt Bio AG regarding Paragraph IV—Part 1", Pursuant to § 505G)(2)(B)(ii) of the Fed. Food, Drug & Cosmetic Act for U.S. Pat. Nos.: 6,780,889; 7,262,219; 7,668,730; 7,765,106; 7,765,107; 7,851,506; 7,895,059; 8,253,650; 8,324,275; 8,457,988; 8,589,182; 8,731,963; 8,772,306; 8,859,619; 8,952,062; and, (Jun. 5, 2015), 1-67.
"Letter from Wockhardt Bio AG regarding Paragraph IV—Part 2", Pursuant to § 505G)(2)(B)(ii) of the Fed. Food, Drug & Cosmetic Act for U.S. Pat. Nos.: 6,780,889; 7,262,219; 7,668,730; 7,765,106; 7,765,107; 7,851,506; 7,895,059; 8,263,650; 8,324,275; 8,457,988; 8,589,182; 8,731,963; 8,772,306; 8,859,619; 8,952,062; and, (Jun. 5, 2015), 68-137.
"Lupin Paragraph IV Notice_Part 1", U.S. Pat. Nos. 6,780,889B2, 7,262,219B2, 7,668,730B2, 7,765,106B2 ,7,765,107B2, 7,851,506B2, 7,895,059B2, 8,263,650B2, 8,324,275B2, 8,457,988B2, 8,589,182B2, 8,731,963B2, 8,772,306B2, 8,859,619B2, 9,050,302B2AreInvalid, Unenforceable,and/orWillNotBeInfringed, (Jul. 23, 2015), 74 pgs.

(56) References Cited

OTHER PUBLICATIONS

"Lupin Paragraph IV Notice_Part 2", U.S. Pat. Nos. 6,780,889B2, 7,262,219B2, 7,668,730B2, 7,765,106B2 ,7,765,107B2, 7,851,506B2, 7,895,059B2, 8,263,650B2, 8,324,275B2, 8,457,988B2, 8,589,182B2, 8,731,963B2, 8,772,306B2, 8,859,619B2, 9,050,302B2AreInvalid, Unenforceable,and/orWillNotBeInfringed, (Jul. 23, 2015), 74 pgs.
"Lupin Paragraph IV Notice_Part 3", U.S. Pat. Nos. 6,780,889B2, 7,262,219B2, 7,688,730B2, 7,765,106B2, ,7,765,107B2, 7,851,506B2, 7,895,059B2, 8,263,650B2, 8,324,275B2, 8,457,988B2, 8,589,182B2, 8,731,963B2, 8,772,306B2, 8,859,619B2, 9,050,302B2AreInvalid, Unenforceable,and/orWillNotBeInfringed, (Jul. 23, 2015), 74 pgs.
"Lupin Paragraph IV Notice_Part 4", U.S. Pat. Nos. 6,780,889B2, 7,262,219B2, 7,668,730B2, 7,765,106B2 ,7,765,107B2, 7,851,506B2, 7,895,059B2, 8,263,650B2; 8,324,275B2, 8,457,988B2, 8,589,182B2, 8,731,963B2, 8,772,306B2, 8,859,619B2, 9,050,302B2AreInvalid, Unenforceable,and/orWillNotBeInfringed, (Jul. 23, 2015), 74 pgs.
"Lupin Paragraph IV Notice_Part 5", U.S. Pat. Nos. 6,780,889B2, 7,262,219B2, 7,668,730B2, 7,765,106B2 ,7,765,107B2, 7,851,506B2, 7,895,059B2, 8,263,650B2, 8,324,275B2, 8,457,988B2, 8,589,182B2, 8,731,963B2, 8,772,306B2, 8,859,619B2, 9,050,302B2AreInvalid, Unenforceable,and/orWillNotBeInfringed, (Jul. 23, 2015), 77 pgs.
"Lupin Paragraph IV Notice_Part 6", U.S. Pat. Nos. 6,780,889B2, 7,262,219B2, 7,668,730B2, 7,765,106B2 ,7,765,107B2, 7,851,506B2, 7,895,059B2, 8,263,650B2, 8,324,275B2, 8,457,988B2, 8,589,182B2, 8,731,963B2, 8,772,306B2, 8,859,619B2, 9,050,302B2AreInvalid, Unenforceable,and/orWillNotBeInfringed, (Jul. 23, 2015), 75 pgs.
"Making Good in Your Own Mail-Order Business", Changing Times—The Kiplinger Magazine, (Oct. 1980), 66-68.
"Managing the Risks from Medical Product Use: Report to the FDA Commissioner from the Task Force on Risk Management", U.S. Department of Health and Human Services Food and Drug Administration, (May 1999), 164 pgs.
"Mandatory Notices by Jazz Pharmaceuticals, Inc.", *Amneal Pharmaceuticals, LLC, and Par Pharmaceutical, Inc. v. Jazz Pharmaceuticals, Inc.* Case IPR2015-01903, (Oct. 5, 2015), 9 pgs.
"Mandatory Notices by Jazz Pharmaceuticals, Inc.", *Wockhardt Bio AG v. Jazz Pharmaceuticals, Inc.*Case IPR2015-01816 Wockhardt _ 059 IPR, 9 pgs.
"Mandatory Notices by Jazz Pharmaceuticals, Inc.", *Wockhardt Bio AG v. Jazz Pharmaceuticals, Inc.*CaseIPR 2015-01815 Wockhardt_ 106 IPR, 9 pgs.
"Mandatory Notices by Jazz Pharmaceuticals, Inc.", *Wockhardt Bio AG v. Jazz Pharmaceuticals, Inc.*CaseIPR 2015-01820 Wockhardt_ 107 IPR, 9 pgs.
"Mandatory Notices by Jazz Pharmaceuticals, Inc.", *Wockhardt Bio AG v. Jazz Pharmaceuticals, Inc.*CaseIPR 2015-01814 Wockhardt_ 988 IPR, 9 pgs.
"Mandatory Notices by Jazz Pharmaceuticals, Inc.", *Wockhardt Bio AG v. Jazz Pharmaceuticals, Inc.*CaseIPR 2015-01813 Wockhardt_ 182 IPR, 10 pgs.
"Mandatory Notices by Jazz Pharmaceuticals, Inc.", *Wockhardt Bio AG v. Jazz Pharmaceuticals, Inc.*CaseIPR 2015-01818 Wockhardt_ 730 IPR, 9 pgs.
"Markman Opinion, filed Sep. 14, 2012, in the case of *Jazz Pharmaceuticals, Inc.,* Plaintiff, v. *Roxane Laboratories, Inc.,* Defendant (United States District Court for the District of New Jersey, Civil 10-6108 ES)", (Sep. 14, 2012), 43 pgs.
"Motion for Joinder Inter Partes Review of U.S. Pat. No. 7,668,730", United States Patent, and Trademark Office before the Patent Trial and Appeal Board *Wockhardt Bio Ag* Petitioner v. *Jazz Pharmaceuticals, Inc.* Case IPR: IPR2015-01820, (Aug. 27, 2015), 14 pgs.
"Motion for Joinder Inter Partes Review of U.S. Pat. No. 7,765,106", *Wockhardt Bio AG, Wockhardt Limited, Wockhardt USA LLC, and Morton Grove Pharmaceuticals, Inc.* v. *Jazz Pharmaceuticals, Inc.* Case IPR: IPR2015-01815, (Aug. 27, 2015), 14 pgs.
"Motion for Joinder Inter Partes Review of U.S. Pat. No. 7,765,107", United States Patent and Trademark Office Before the Patent Trial and Appeal Board *Wockhardt Bio AG* Petitioner v. *Jazz Pharmaceuticals, Inc.* Case IPR: IPR2015-01820, (Aug. 27, 2015), 14 pgs.

"Motion for Joinder Inter Partes Review of U.S. Pat. No. 7,895,059", United States Patent and Trademark Office Before the Patent Trial and Appeal Board *Wockhardt Bio AG* Petitioner v. *Jazz Pharmaceuticals, Inc.* Patent Owner Case IPR: IPR2015-01816, (Aug. 27, 2015), 14 pgs.
"Motion for Joinder Under 35 U.S.C. § 315(c) and 37 C.F.R. §§ 42.22 and 42.122(b)", United States Patent and Trademark Office Before the Patent Trial and Appeal Board *Wockhardt Bio AG* Petitioner v. *Jazz Pharmaceuticals, Inc.* Patent Owner Case IPR: IPR2015-01814, (Aug. 27, 2015), 14 pgs.
"NASCSA National Conference", Orphan Medical, Inc., (Nov. 2000), 8 pgs.
"Notice of Electronic Filing: Civil inital Pleadings (Attorney/Credit Card) Use Case 33-1", US District Court, District of new Jersey [LIVE], (Jan. 18, 2013), 2 pgs.
"Notice of Electronic Filing: Civil Inital Pleadings (Attorney/Credit Card) Use Case 33-1)", *Jazz Pharmaceuticals, Inc.* v. *Amneal Pharmaceuticals, LLC,* (United States District Court, District of New Jersey [LIVE]), (Sep. 12, 2013), 1 pg.
"Notice of Filing Date Accorded to Petition and Time for Filing Patent Owner Preliminary Response for CBM Patent U.S. Pat. No. 7,668,730", (Jul. 21, 2014), 3 pgs.
"Notice of Filing Date Accorded to Petition and Time for Filing Patent Owner Preliminary Response for CBM Patent U.S. Pat. No. 8,589,182", (Jul. 21, 2014), 3 pgs.
"Notice of Paragraph IV Certification Concerning ANDA 203631 for Sodium Oxybate Oral Solution, 500 mg/mL", Amneal Pharmaceuticals, LLC, (Dec. 7, 2012), 4 pgs.
"Notice of Paragraph IV Certification Concerning ANDA 203631 for Sodium Oxybate Oral Solution. 500 mg/mL", Amneal Pharmaceuticals, LLC, (Dec. 12, 2012), 4 pgs.
"Notice of Paragraph IV Certification on behalf of Par Pharmaceutical", Detailed Statement of the Factual and Legal Bases for Par's Paragraph IV Patent Certification and Offer of Confidential Access, (Nov. 20, 2013), 190 pgs.
"Notice of Paragraph IV Certification on behalf of PAR Pharmaceutical, Inc., Pursuant to § 505(j)(2)(B)(ii) of the Federal Food, Drug and Cosmetic Act and 21 U.S.C. § 355(j)(2)(B)(ii) and § 314.95 of Title 21 of the Code of Federal Regulations", Par Pharmaceuticals, Inc., (Jun. 2, 2014), 54 pgs.
"Notice of Voluntary Dismissal of Counterclaims Pertaining to U.S. Pat. Nos. 7,668,730; 7,765,106; and 7,765,107 (Contained in Counts I, II) Pursuant to Fed. R. Civ. P. 41(a), (c)", *Jazz Pharmaceuticals, Inc.* v. *Amneal Pharmaceuticals, LLC,* (United States District Court, District of New Jersey Civil Action No. 13-391 ES-SCM, (Jul. 15, 2013), 2 pgs.
"Orange Book Approved Drug Products with Therapeutic Equivalence Evaluations: Search Results for Xyrem", U.S. Food and Drug Administration, [Online]. Retrieved from the Internet: <URL: http://www.accessdata.fda.gov/scripts/cder/ob/docs/obdetail.cfm?Appl_No=021196&TABLE1=OB_Rx>, (Accessed Jun. 12, 2014), 4 pgs.
"Orphan Medical Slides: Xyrem (sodium oxybate) oral solution", Peripheral and Central Nervous System Drugs Advisory Committee Meeting, [Online]. Retrieved from the Internet: <URL: http://www.fda.gov/ohrms/dockets/ac/01/slides/3754s1_01_orphanmedical/index.htm>, (Jun. 6, 2001), 167 pgs.
"Par Pharmaceautical, Inc.'s Power of Attorney", United States Patent and Trademark Office Before the Patent Trial and Appeal Board *Amneal Pharmaceauticals, LLC. and Par Parmaceutical, Inc.* Petitioners v. *Jazz Pharmaceauticals, Inc.*Patent Owner Case CMB: Unassigned U.S. Pat. No. 8,457,988, (Jul. 7, 2014), 3 pgs.
"Par Pharmaceutical Inc. Certified File History Part 1 of Exhibit 1002 for CBM for U.S. Pat. No. 8,589,182", 1,195 pgs.
"Par Pharmaceutical Inc.'s Power of Attorney", *Amneal Pharmaceuticals LLC and Par Pharmaceutical, Inc.* v. *Jazz Pharmaceuticals, LLC.* Inter Partes Review of U.S. Pat. No. 7,765,106, (Jan. 7, 2015), 3 pgs.
"Par Pharmaceutical's Power of Attorney for covered business methods review of U.S. Pat. No. 7,668,730", *Par Pharmaceutical, Inc., and Roxane Laboratories, Inc.* Petitioners v.*Jazz Pharmaceuticals, Inc.*Patent Owner Case CBM: Unassigned U.S. Pat. No. 7,668,730 Par Pharmaceutical, Inc.'s Power of Attorney, (Jul. 9, 2014), 3 pgs.

(56) References Cited

OTHER PUBLICATIONS

"Par Pharmaceutical's Power of Attorney for covered business methods review of U.S. Pat. No. 7,765,107", Amneal Pharmaceuticals, LLC's Power of Attorney for Inter Partes Review of U.S. Pat. No. 7,765,107, (Jan. 8, 2015), 3 pgs.
"Par Pharmaceutical, Inc's Power of Attorney for Inter Partes Review of U.S. Pat. No. 8,731,963" *Amneal Pharmaceuticals LLC and Par Pharmaceutical, Inc.* v. *Jazz Pharmaceuticals, Inc.* Case IPR: Unassigned, 4 pgs.
"Par Pharmaceutical, Inc. Certified File History Part 2 of Exhibit 1002 for CBM for U.S. Pat. No. 8,589,182", 1,195 pgs.
"Par Pharmaceutical, Inc.'s Power of Attorney", *Amneal Pharmaceuticals, LLC and Par Pharmaceutical, Inc.,* v. *Jazz Pharmaceuticals, Inc.* United States District Court, District of New Jersey, (Jul. 9, 2014), 3 pgs.
"Par Pharmaceutical, Inc.'s Power of Attorney", *Amneal Pharmaceuticals, LLC and Par Pharmaceutical, Inc.,* v. *Jazz Pharmaceuticals, Inc.* United States District Court, District of New Jersey, (Jul. 7, 2014), 3 pgs.
"Par Pharmaceutical, Inc.'s Power of Attorney", *Par Pharmaceutical, Inc. and Roxane Laboratories, Inc.* v. *Jazz Pharmaceuticals, Inc.* United States District Court, District of New Jersey, (Aug. 4, 2014), 3 pgs.
"Par Pharmaceutical, Inc.'s Power of Attorney", *Amneal Pharmaceuticals, LLC, Par Pharmaceutical, Inc., and Roxane Laboratories, Inc.* v. *Jazz Pharmaceuticals, Inc.* United States District Court, District of New Jersey, (Jun. 24, 2014), 3 pgs.
"Par Pharmaceutical, Inc., and Amneal Pharmaceuticals, LLC's exhibit list (petition for Inter Partes review of U.S. Pat. No. 7,668,730 )", Inter Partes Review of U.S. Pat. No. 7,668,730 Par and Amneal Exhibit List Certification of Service (37 C.F.R. §§ 42.6(e), 42.105(a)), (Jan. 8, 2015), 7 pgs.
"Par Pharmaceutical, Inc., and Roxane Laboratories, Inc.'s Exhibit List (CBM Patent Review of U.S. Pat. No. 7,668,730)", *Par Pharmaceutical, Inc., and Roxane Laboratories, Inc.* v. *Jazz Pharmaceuticals, Inc.* United States District Court, District of New Jersey, (Jul. 9, 2014), 6 pgs.
"Par Pharmaceutical, Inc.'s Exhibit List Petition for Inter Partes Review of U.S. Pat. No. 7,895,059", United States Patent and Trademark Office Before the Patent Trial and Appeal Board *Par Pharmaceutical, Inc.*, Petitioner v. *Jazz Pharmaceuticals. Inc*.Patent Owner Case IPR: Unassigned U.S. Pat. No. 7,895,059, (Jan. 8, 2015), 7 pgs.
"Par Pharmaceutical, Inc.'s Power of Attorney", United States Patent and Trademark Office Before the Patent Trial and Appeal Board *Amneal Pharmaceuticals LLC and Par Pharmaceutical, Inc*,Petitioners v. *Jazz Pharmaceuticals, LLC* Patent Owner Case IPR: Unassigned U.S. Pat. No. 8,589,182, (Jan. 8, 2015), 3 pgs.
"Par Pharmaceutical, Inc.Certified File History of Exhibit 1016 for CBM for U.S. Pat. No. 7,668,730", 818 pgs.
"Part 1 of Exhibit 1002 for CBM U.S. Pat. No. 7,895,059", 100 pgs.
"Part 1 of Exhibit 1002 for CBM U.S. Pat. No. 8,457,988", 100 pgs.
"Part 1 of Exhibit 1016 for CBM U.S. Pat. No. 7,668,730", 112 pgs.
"Part 2 of Exhibit 1002 for CBM U.S. Pat. No. 7,895,059", 101 pgs.
"Part 2 of Exhibit 1002 for CBM U.S. Pat. No. 8,457,988", 79 pgs.
"Part 2 of Exhibit 1016 for CBM U.S. Pat. No. 7,668,730", 112 pgs.
"Part 3 of Exhibit 1016 for CBM U.S. Pat. No. 7,668,730", 112 pgs.
"Part 4 of Exhibit 1016 for CBM U.S. Pat. No. 7,668,730", 112 pgs.
"Part 5 of Exhibit 1016 for CBM U.S. Pat. No. 7,668,730", 112 pgs.
"Patent application transmittal; Continuation of prior U.S. Appl. No. 10/322,348", The United States patent and Trademark Office, (Jan. 30, 2014), 201 pgs.
"Patent Assignment Abstract of Title for U.S. Appl. No. 12/704,097", Public Pair, [Online]. Retrieved from the Internet: <URL: (Accessed Mar. 9, 2015), 3 pgs.
"Patent Notice Pursuant to § 505(j)(2)(B)(ii) [21 USC§ 355(j)(2)(B)(ii)]", Roxane Laboratories, Inc., (Jan. 9, 2015), 32 pgs.
"Patti Engel, Exhibit 1012", LinkedIn, [Online]. Retrieved from the Internet: <URL: https://www.linkedin.com/...ple_res_name&trkInfo=VSRPsearchId%3A102316431425932629960%2CVSRPtargetId%3A3508435%2CVSRPcmpt%3Aprimary%2CVSRPnm%3A[03/09/2015 3:24:45 PM]>, (Accessed Mar. 9, 2015), 5 pgs.
"Peripheral and Central Nervous System Drugs Advisory Committee", Department of Health and Human Services Food and Drug Administration Center for Drug Evaluation and Research, Holiday Inn, Bethesda, Maryland, (Jun. 6, 2001), 7 pages.
"Peripheral and Central Nervous System Drugs Advisory Committee", Department of Health and Human Services Food and Drug Administration Center for Drug Valuation and Research. Holiday Inn Bethesda, Maryland, (Jun. 6, 2001), 400 pgs.
"Peripheral and Central Nervous System Drugs Advisory Committee—Transcript", Department of Health and Human Services Food and Drug Administration Center for Drug Evaluation and Research, Holiday Inn, Bethesda, Maryland, (Jun. 6, 2001), 381 pgs.
"Peripheral and Central Nervous System Drugs Advisory Committee, Briefing Information", [Online]. Retrieved from the Internet: <URL: https://web.archive.org/web/20010701233052/http://www.fda.gov/ohrms/dockets/ac/01/briefing/3754b1.htm>, (Jul. 1, 2001), 1 pg.
"Peripheral and Central Nervous System Drugs Advisory Committee; Notice of Meeting", Federal Register. vol. 66, No. 93, (May 14, 2001), p. 24391.
"Petition for Covered Business Method Patent Review of U.S. Pat. No. 7,668,730 Under 35 U.S.C. § 321 and §18 of the Leahy-Smith America Invents Act", *Par Pharmaceutical, Inc., and Roxane Laboratories, Inc.* v. *Jazz Pharmaceuticals, Inc.* United States District Court, District of New Jersey, (Jul. 9, 2014), 84 pgs.
"Petition for Covered Business Method Patent Review of U.S. Pat. No. 7,765,106 Under 35 U.S.C. § 321 and §18 of the Leahy-Smith America Invents Act", *Roxane Laboratories, Inc. and Par Pharmaceutical, Inc.,* v. *Jazz Pharmaceuticals, Inc.* United States District Court, District of New Jersey, (Aug. 4, 2014), 84 pgs.
"Petition for Covered Business Method Patent Review of U.S. Pat. No. 7,895,059 Under 35 U.S.C. § 321 and §18 of the Leahy-Smith America Invents Act", *Amneal Pharmaceuticals, LLC, Par Pharmaceutical, Inc., and Roxane Laboratories, Inc.* v. *Jazz Pharmaceuticals, Inc.* United States District Court, District of New Jersey, (Jun. 24, 2014), 84 pgs.
"Petition for Covered Business Method Patent Review of U.S. Pat. No. 8,457,988 Under 35 U.S.C. § 321 and §18 of the Leahy-Smith America Invents Act", *Amneal Pharmaceuticals, LLC, and Par Pharmaceutical, Inc.* v. *Jazz Pharmaceuticals, Inc.* United States District Court, District of New Jersey, (Jul. 7, 2014), 84 pgs.
"Petition for Covered Business Method Patent Review of U.S. Pat. No. 8,589,182 Under 35 U.S.C. § 321 and §18 of the Leahy-Smith America Invents Act", *Amneal Pharmaceuticals, LLC, and Par Pharmaceutical, Inc.* v. *Jazz Pharmaceuticals, Inc.* United States District Court, District of New Jersey, (Jul. 9, 2014), 84 pgs.
"Petition for Inter Partes Review of U.S. Pat. No. 7,668,730", United States Patent and Trademark Office Before the Patent Trial and Appeal Board *Wockhardt Bio AG* Petitioner V. *Jazz Pharmaceuticals, Inc.* Patent Owner Case IPR: Unassigned, (Aug. 27, 2015), 49 pgs.
"Petition for Inter Partes Review of U.S. Pat. No. 7,895,059", United States Patent and Trademark Office Before the Patent Trial and Appeal Board *Wockhardt BIO AG* Petitioner v. *Jazz Pharmaceuticals, Inc*.Patent Owner, (Aug. 27, 2015), 50 pgs.
"Petition for Inter Partes Review of U.S. Pat. No. 8,457,988", United States patent and trademark Office Before the Patent Trial and Appeal Board *Wockhardt Bio AG* Petitioner v.*Jazz Pharmaceauticals, Inc*.Patent Owner, (Aug. 27, 2015), 50 pgs.
"Petition for Inter Partes Review of U.S. Pat. No. 8,589,182", United States Patent and Trademark Office Before the Patent Trial and Appeal Board *Wockhardt Bio AG* Petitioner v.*Jazz Pharmaceauticals, Inc*.Patent Owner Case IPR: Unassigned, (Aug. 27, 2015), 45 pgs.
"Petition for Inter Partes Review of U.S. Pat. No. 7,668,730 Under 35 U.S.C. § 311-319 and 37 C.F.R. § 42.1-,80, 42.100-.123", *Amneal Pharmaceuticals, LLC, and Par Pharmaceutical, Inc.* v. *Jazz Pharmaceuticals, Inc.* United States District Court, District of New Jersey, (Jan. 8, 2015), 65 pgs.
"Petition for Inter Partes Review of U.S. Pat. No. 7,765,106 Under 35 U.S.C. §§ 311-319 and 37 C.F.R. §§ 42.1-.80, 42.100-.123",

(56) References Cited

OTHER PUBLICATIONS

*Amneal Pharmaceuticals, LLC, and Par Pharmaceutical, Inc.* v. *Jazz Pharmaceuticals, Inc.* United States District Court, District of New Jersey, (Jan. 8, 2015), 64 pgs.
"Petition for Inter Partes Review of U.S. Pat. No. 7,765,106 Under 35 U.S.C. §§ 311-319 and 37 C.F.R. §§ 42.1-.80, 42.100-.123", *Wockhardt Bio AG* v. *Jazz Pharmaceuticals, Inc.*, (Aug. 27, 2015), 41 pgs.
"Petition for Inter Partes Review of U.S. Pat. No. 7,765,107 Under 35 U.S.C. §§ 311-319 and 37 C.F.R. §§ 42.1-.80, 42.100-.12", *Wockhardt Bio AG* v. *Jazz Pharmaceuticals, Inc.* Case IPR: Unassigned, (Aug. 27, 2015), 43 pgs.
"Petition for Inter Partes Review of U.S. Pat. No. 7,765,107 Under 35 U.S.C. §§ 311-319 and 37 C.F.R. §§ 42.1-.80, 42.100-.123", *Amneal Pharmaceuticals, LLC, and Par Pharmaceutical, Inc.* v. *Jazz Pharmaceuticals, Inc.* United States District Court, District of New Jersey, (Jan. 8, 2015), 64 pgs.
"Petition for Inter Partes Review of U.S. Pat. No. 7,895,059 Under 35 U.S.C. § 311-319 and 37 C.F.R. § 42.1-.80, 42.100", *Coalition for Affordable Drugs III LLC* v. *Jazz Pharmaceuticals, Inc.* United States District Court, District of New Jersey, (Apr. 6, 2015), 67 pgs.
"Petition for Inter Partes Review of U.S. Pat. No. 7,895,059 Under 35 U.S.C. § 311-319 and 37 C.F.R. § 4 2.1-.80, 42.100-.123", *Par Pharmaceutical, Inc.* v. *Jazz Pharmaceuticals, Inc.* United States District Court, District of New Jersey, (Jan. 8, 2015), 65 pgs.
"Petition for Inter Partes Review of U.S. Pat. No. 8,457,988 Under 35 U.S.C. § 311-319 and 37 C.F.R. § 42.1-.80, 42.100-.123", *Par Pharmaceutical, Inc.* v. *Jazz Pharmaceuticals, Inc.* United States District Court, District of New Jersey, (Jan. 8, 2015), 65 pgs.
"Petition for Inter Partes Review of U.S. Pat. No. 8,589,182 Under 35 U.S.C. §§ 311-319 and 37 C.F.R. §§ 42.1-.80, 42.100-.123", *Amneal Pharmaceuticals, LLC, and Par Pharmaceutical, Inc.* v. *Jazz Pharmaceuticals, Inc.* United States District Court, District of New Jersey, (Jan. 8, 2015), 64 pgs.
"Petition for Inter Partes Review of U.S. Pat. No. 8,731,963", *Amneal Pharmaceuticals LLC and Par Pharmaceutical, Inc.* v. *Jazz Pharmaceuticals, Inc.* Case IPR: Unassigned, 65 pgs.
"Power of Attorney Certificate under 37 CFR § 3.73(b) & Change of Correspondence Address, Exhibit 1013", on behalf of Orphan Medical, (Feb. 11, 2010), 1 pg.
"Preliminary Amendment pursuant to 37 CFR Sec. 1.115", U.S. Appl. No. 11/104,013, filed Apr. 12, 2005, 3 pgs.
"Reply to Counterclaims", *Jazz Pharmaceuticals, Inc.* v. *Roxane Laboratories, Inc.*, United States District Court, District of New Jersey Civil Action No. 10-6108 (SDW) (MCA), (Feb. 7, 2011), 37 pgs.
"Reply to Counterclaims", *Jazz Pharmaceuticals, Inc.* v. *Roxane Laboratories, Inc.*, (United States District Court, District of New Jersey Civil Action No. 11-660 (SDW) (MCA) Lead Action CV-10-6108), (Apr. 18, 2011), 6 pgs.
"Report on the Filing or Determination of an Action Regarding a Patent or Trademark", *Jazz Pharmaceuticals, Inc.* v. *Par Pharmaceuticals, Inc.*, United States District Court, District of New Jersey, Case No. 2:13-cv-07884-ES-JAD, (Dec. 27, 2013), 1 pg.
"Roxane Laboratories, Inc. and Par Pharmaceutical, Inc.'s Exhibit List (CBM Patent Review of U.S. Pat. No. 7,765,106)", *Roxane Laboratories, Inc. and Par Pharmaceutical, Inc.*, v. *Jazz Pharmaceuticals, Inc.* United States District Court, District of New Jersey, (Aug. 4, 2014), 5 pgs.
"Roxane Laboratories, Inc. File History of Exhibit 1002 for CBM for U.S. Pat. No. 7,765,106 0", 266 pgs.
"Roxane Laboratories, Inc. File History Part 1 of Exhibit 1016 for CBM for U.S. Pat. No. 7,765,106", 112 pgs.
"Roxane Laboratories, Inc. File History Part 2 of Exhibit 1016 for CBM for U.S. Pat. No. 7,765,106", 112 pgs.
"Roxane Laboratories, Inc. File History Part 3 of Exhibit. 1016 for CBM for U.S. Pat. No. 7,765,106", 112 pgs.
"Roxane Laboratories, Inc. File History Part 4 of Exhibit 1016 for CBM for U.S. Pat. No. 7,765,106", 112 pgs.
"Roxane Laboratories, Inc. File History Part 5 of Exhibit 1016 for CBM for U.S. Pat. No. 7,765,106", 112 pgs.
"Roxane Laboratories, Inc.'s Amended Answer and Affirmative Defenses to Plaintiff's Complaint Regarding U.S. Pat. No. 8,234,275", Exhibit 2, (Apr. 26, 2013), 15 pgs.
"Roxane Laboratories, Inc.'s Amended Answer, Affirmative Defenses and Counterclaims to Plaintiff's Complaint Regarding U.S. Pat. No. 8,263,650", Exhibit 1, (Apr. 26, 2013), 23 pgs.
"Roxane Laboratories, Inc.'s Answer and Affirmative Defenses to Plaintiff's Complaint", (Jan. 4, 2013), 8 pgs.
"Roxane Laboratories, Inc.'s Answer, Affirmative Defenses and Counterclaims to Plaintiff's Complaint", (Dec. 29, 2010), 21 pgs.
"Roxane Laboratories, Inc.'s Answer, Affirmative Defenses and Counterclaims to Plaintiff's Complaint", (Mar. 9, 2011), 13 pgs.
"Roxane Laboratories, Inc.'s Answer, Affirmative Defenses and Counterclaims to Plaintiff's Complaint", (Jun. 1, 2011), 12 pgs.
"Roxane Laboratories, Inc.'s Answer, Affirmative Defenses and Counterclaims to Plaintiff's Complaint", (Nov. 9, 2012), 18 pgs.
"Roxane Laboratories, Inc.'s Answer, Affirmative Defenses and Counterclaims to Plaintiff's Complaint", *Jazz Pharmaceuticals, Inc.* v. *Roxane Laboratories, Inc.*, United States District Court, District of New Jersey Civil Action No. 10-6108 (ES) (CLW), (Dec. 29, 2010), 21 pgs.
"Roxane Laboratories, Inc.'s Initial Invalidity and Noninfringement Contentions Pursuant to Local Patent Rule 3.6", *Jazz Pharmaceuticals, Inc.* v. *Roxane Laboratories, Inc.*, (United States District Court, District of New Jersey Civil Action No. 2:10-cv-06108 (SDW) (MCA)), (Apr. 14, 2011), 317 pgs.
"Roxane Laboratories, Inc.'s Opening Markman Brief in Support of Its Claim Constructions", *Jazz Pharmaceuticals, Inc.* v. *Roxane Laboratories, Inc.*, )United States District Court, District of New Jersey Civil Action No. 2.10-cv-06108 (ES) (CLW)), (Dec. 5, 2011), 37 pgs.
"Roxane Laboratories, Inc.'s Power of Attorney", *Par Pharmaceutical, Inc., and Roxane Laboratories, Inc.* v. *Jazz Pharmaceuticals, Inc.* United States District Court, District of New Jersey, (Aug. 4, 2014), 3 pgs.
"Roxane Laboratories, Inc.'s Power of Attorney", *Par Pharmaceutical, Inc., and Roxane Laboratories, Inc.* v. *Jazz Pharmaceuticals, Inc.* United States District Court, District of New Jersey, (Jul. 9, 2014), 3 pgs.
"Roxane Laboratories, Inc.'s Power of Attorney", *Amneal Pharmaceuticals, LLC, Par Pharmaceutical, Inc., and Roxane Laboratories, Inc.* v. *Jazz Pharmaceuticals, Inc.* United States District Court, District of New Jersey, (Jun. 24, 2014), 3 pgs.
"Roxane Laboratories, Inc.'s Responsive Markman Brief in Support of Its Claim Constructions", *Jazz Pharmaceuticals, Inc.* v. *Roxane Laboratories, Inc.*, (United States District Court, District of New Jersey Civil Action No. 2:10-cv-06108 (ES) (CLW)), (Feb. 21, 2012), 27 pgs.
"Section 793, Exhibit 1009", Webster's Third New International Dictionary of the English Language Unabridged, (2002), p. 3.
"Slides: Pediatric Subcommittee of the Peripheral and Central Nervous system Drugs Advisory Committee", [Online]. Retrieved from the Internet: <URL: http://www.fda.gov/ohrms/dockets/ac/01/slides/3754s1.htm>, (Jun. 6, 2001), 86 pgs.
"Sodium oxybate, Exhibit 1010", Wikipedia, (Accessed Mar. 10, 2015), 7 pgs.
"Statement Under 37 CFR 3.73(b)", Wockhardt '059 IPR, 2 pgs.
"Statement Under 37 CFR 3.73(b)", Wockhardt '988 IPR, 2 pgs.
"Statement Under 37 CFR 3.73(b)", Wockhardt '106 IPR, 2 pgs.
"Statement Under 37 CFR 3.73(b)", Wockhardt '107 IPR, 2 pgs.
"Statement Under 37 CFR 3.73(b)", Wockhardt '182 IPR, 2 pgs.
"Statement Under 37 CFR 3.73(b)", Wockhardt '730 IPR, 2 pgs.
"Summons in a Civil Case", *Jazz Pharmaceuticals, Inc.* v. *Par Pharmaceuticals, Inc.*, United States District Court, District of New Jersey, Case No. 213-CV-07884-ES-JAD, (Dec. 31, 2013), 2 pgs.
"System for Thalidomide Education and Prescribing Safety (S.T.E. P.S.) Starter Kit", Celgene Corporation, (2001), 103 pgs.
"The Controlled substance control system (CSCS)", CSCS Enterprises, Inc. AMN1036 IPR of U.S. Pat. No. 8,589,182, (Sep. 10, 2001), 19 pgs.

(56) References Cited

OTHER PUBLICATIONS

"Wockhardt Bio AG's Exhibit List", United States Patent and Trademark Office Before the Patent Trial and Appeal Board *Wockhardt Bio AG* Petitioner v. *Jazz Pharmaceuticals, Inc*. Patent Owner Case: IPR2015-00546 U.S. Pat. No. 7,765,106, (Aug. 27, 2015), 6 pgs.
"Wockhardt Bio Ag's Exhibit List", United States Patent and Trademark Office Before the Patent Trial and Appeal Board *Wockhardt BIO AG* Petitioner v.*Jazz Pharmaceuticals, Inc*. Patent Owner Case Unassigned U.S. Pat. No. 8,589,182, (Aug. 27, 2015), 5 pgs.
"Wockhardt Bio Ag's Exhibit List", United States Patent and Trademark Office Before the Patent Trial and Appeal Board *Wockhardt Bio AG* Petitioner v.*Jazz Pharmaceuticals, Inc*. Patent Owner CASE: Unassigned U.S. Pat. No. 7,895,059, (Aug. 27, 2015), 6 pgs.
"Wockhardt Bio Ag's Exhibit List", USPTO Before the Patent Trial and Appeal Board *Wockhardt BIO AG* Petitioner v.*Jazz Pharmaceuticals, Inc*.Patent Owner Case U.S. Pat. No. 8,457,988, (Aug. 27, 2015), 5 pgs.
"Wockhardt Bio Ag's Exhibit List", United States Patent and Trademark Office Before the Patent Trial and Appeal Board *Wockhardt BIO AG* Petitioner v.*Jazz Pharmaceuticals, Inc*. Patent Owner Case Unassigned U.S. Pat. No. 7,668,730, (Aug. 27, 2015), 5 pgs.
"Wockhardt Bio Ag's Power of Attorney", United States Patient and Trademark Office Before the Patent Trial and Appeal Board *Wockhardt Bio AG* Petitioner v.*Jazz Pharmaceuticals, Inc*. U.S. Pat. No. 7,668,730, (Aug. 27, 2015), 3 pgs.
"Wockhardt Bio Ag's Power of Attorney", United States Patient and Trademark Office Before the Patent Trial and Appeal Board *Wockhardt BioAG* Petitioner v.*Jazz Pharmaceuticals, Inc*.U.S. Pat. No. 8,457,988, (Aug. 27, 2015), 3 pgs.
"Wockhardt Bio Ag's Power of Attorney", United States Patient and Trademark Office Before the Patent Trial and Appeal Board *Wockhardt Bio AG* Petitioner v.*Jazz Pharmaceuticals, Inc*. U.S. Pat. No. 7,765,107, (Aug. 27, 2015), 3 pgs.
"Wockhardt Bio Ag's Power of Attorney", United States Patient and Trademark Office Before the Patent Trial and Appeal Board *Wockhardt Bio AG* Petitioner v.*Jazz Pharmaceuticals, Inc*. U.S. Pat. No. 7,765,106, (Aug. 27, 2015), 3 pgs.
"Wockhardt Bio Ag's Power of Attorney", United States Patent and Trademark Office Before the Patent Trial and Appeal Board *Wockhardt BIO AG* Petitioner v.*Jazz Pharmaceuticals, Inc*. Patent Owner Case:Unassigned U.S. Pat. No. 8,589,182, (Aug. 27, 2015), 3 pgs.
"Wockhardt Bio Ag's Power of Attorney", United States Patient and Trademark Office Before the Patent Trial and Appeall Board *Wockhardt BIO AG* Petitioner v.*Jazz Pharmaceuticals, Inc*. Patent Owner U.S. Pat. No. 7,895,059, (Aug. 27, 2015), 3 pgs.
"Workhardt Bio Ag's Exhibit List", United States Patent and Trademark Office Before the Patent Trial and Appeal Board *Wockhardt Bio AG* Petitioner v.*Jazz Pharmaceuticals, Inc*. Patent Owner Case: IPR2015-00547 U.S. Pat. No. 7,765,107, (Aug. 27, 2015), 5 pgs.
"Xyrem Prescription and Distribution Process-Video Script", (Feb. 2, 2001), 10 pgs.
Burleson, Ken W, "Review of Computer Applicaitons in Institutional Pharmacy—1975-1981", American Journal of Hospital Pharmacy. vol. 39, (Jan. 1982), 53-70.
Deutsch, Sheryl, "The Verification and Information-Gathering Process", The Credentialing Handbook, Aspen Publishers, Inc., (1999), 231-275.
Fudin, Jeffrey, "Curriculum Vitae", (Feb. 9, 2015), 36 pgs.
Honigfeld, Gilbert, "Effects of the Clozapine National Registry System on Incidence of Deaths Related to Agranulocytosis", Psychiatric Services. vol. 47, No. 1, (Jan. 1996), 52-56.
Honigfeld, Gilbert, et al., "Reducing Clozapine-Related Morbidity and Mortality: 5 Years of Experience with the Clozaril National Registry (Exhibit PAR 1034)", J Clin Psychiatry 59 (suppl 3), (1998), 7 pgs.
Korfhage, Robert R, , Information Storage and Retrieval, Wiley Computer Publishing, (1997), 368.
Mani, Ranjit, "Preliminary Clinical Safety Review of NDA No. 21196", Orphan Medical, Inc., (May 3, 2001), 122 pgs.

Mitchell, Allen, et al., "A Pregnancy-Prevention Program in Women of Childbearing Age Receiving Isotretinoin", The New England Journal of Medicine, vol. 333, No. 2, (Jul. 13, 1995), 101-106.
Oxtoby, David W, et al., , Principles of Modern Chemistry, Fort Worth : Saunders College Pub., (1996), 52-56.
Rome, Ellen, "It's a Rave New World: Rave Culture and Illicit Drug Use in the Young", Cleveland Clinic Journal of Medicine. vol. 68, No. 6, (Jun. 2001), 541-550.
Scrima, L, et al., "Efficacy of Gamma-Hydroxybutyrate Versus Placebo in Treating Narcolepsy-Cataplexy: Double-Blind Subjective Measures", Biol. Psychiatry, 26(4), (1989), 331-343.
Shulman, Sheila R, "The Broader Message of Accutane", AJPH Nov. 1989, vol. 79, No. 11, (Nov. 1989), 1565-1568.
Spurgeon, David, "Advent of Mail-Order Pharmacy Causes Concern Among Some Pharmacists", Can Med Assoc J. 152 (9), (May 1, 1995), 1485-1486.
Ukens, C., "Specialty Pharmacy", Drug Topics, 144, (Jun. 5, 2000), 40-47.
Valuck, Robert J, "Curriculum Vitae", (Jun. 13, 2014), 41 pgs.
Zeldis, Jerome, et al., "S.T.E.P.S: A Comprehensive Program for Controlling and Monitoring Access to Thalidomide", Clinical Therapeutics. vol. 21, No. 2, (1999), 319-330.
"U.S. Appl. No. 15/014,831, Response filed Nov. 16, 2020 to Non Final Office Action dated May 15, 2020", 29 pgs.
"U.S. Appl. No. 15/057,898, Examiner Interview Summary dated Jan. 28, 2021", 2 pgs.
"U.S. Appl. No. 15/057,898, Non Final Office Action dated Oct. 14, 2020", 20 pgs.
"U.S. Appl. No. 15/014,831, Non Final Office Action dated Mar. 8, 2021", 75 pgs.
"U.S. Appl. No. 15/057,898, Final Office Action dated May 5, 2021", 23 pgs.
"U.S. Appl. No. 15/057,898, Response filed Feb. 4, 2021 to Non Final Office Action dated Oct. 14, 2020", 32 pgs.
Jayawant, et al., "The controversy surrounding OxyContin abuse: issues and solutions", Therapeutics and Clinical Risk Management; 77-82, (2005), 6 pgs.
"Advisory Committee Video on Xyrem, Oral Solution", (May 29, 2001), 9 minutes, 8 seconds.
"Xyrem (sodium oxybate) oral solution Videos", Orphan Medical, Inc. 2001 Videos_1-14 on disk, must be paper filed, (Jun. 20, 2014).
"Order—Termination of the Proceedings as to Petitioner Wockhardt Bio AG", *Amneal Pharm. LLC, Par Pharm., Inc., and Wockhardt Bio AG v. Jazz Pharm., Inc*., (May 5, 2016), 5 pgs.
"Stipulation and Order of Dismissal in NJ Civil Action No. 13-391-ES-JAD Consolidated", *Jazz Pharm., Inc*., et al., v. *Amneal Pharm., LLC*, (Oct. 15, 2018), 2 pgs.
"Order on Consolidation in NJ Civil Action No. 13-391-ES-JAD and 13-7884-ES-MAH", *Jazz Pharm., Inc v. Amneal Pharm., LLC; Jazz Pharm., Inc, v. Par Pharm, Inc*., (May 5, 2014), 3 pgs.
"Stipulation and Consolidation Order in NJ Civil Action No. 13-391-ES-JAD and 16-1505-ES-JAD", *Jazz Pharm., Inc. and Jazz Pharm. Ireland Ltd*., v. *Amneal Pharm., LLC; Jazz Pharm, Inc. and Jazz Pharm. Ireland Ltd*. v. *Watson Laboratories, Inc*., (Jun. 28, 2016), 3 pgs.
"Order of Reassignment in NJ Civil Action 11-2523", *Jazz Pharm, Inc,* et al. v. *Roxane Laboratories, Inc*., et al., (Jun. 30, 2011), 1 pg.
"U.S. Appl. No. 15/014,831, Non Final Office Action dated May 15, 2020", 81 pgs.
"U.S. Appl. No. 15/057,898, Examiner Interview Summary dated Jun. 29, 2020", 3 pgs.
"U.S. Appl. No. 15/057,898, Non Final Office Action dated Apr. 20, 2020", 12 pgs.
"U.S. Appl. No. 15/057,898, Response filed Jul. 2, 2020 to Non Final Office Action dated Apr. 20, 2020", 20 pgs.
Nicholson, Katherine L, et al., "GHB: a new and novel drug of abuse", Drug and Alcohol Dependence vol. 63, Issue 1. 1-22, (Jun. 1, 2001), 22 pgs.
"Opinion in *Jazz v. Amneal*", United States Court of Appeals for the Federal Circuit, *Jazz Pharm., Inc*., v. *Amneal Pharm.,LLC*, Appeal No. 17-1671, (Jul. 13, 2018), 27 pgs.
"U.S. Appl. No. 15/014,831, Final Office Action dated Aug. 20, 2021", 37 pgs.

(56) References Cited

OTHER PUBLICATIONS

"U.S. Appl. No. 17/209,608, Notice of Non-Compliant Amendment dated Aug. 9, 2021".
"Complaint for Patent Infringement Exhibit 1026 for CBM Patents Part 1", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 10", *Jazz Pharmaceuticals, Inc. v. Par Pharmaceuticals, Inc*, (United States District Court, District of New Jersey, Civil Action No. 2:13-CV-07884-ES-JAD), 41 pgs.
"Complaint for Patent infringement Exhibit 1026 for CBM Patents Part 2", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 3", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 4", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 5", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 6", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 7", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 8", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 9", *Jazz Pharmaceuticals, Inc. v. Par Pharmaceuticals, Inc*, (United States District Court, District of New Jersey, Civil Action No. 2:13-CV-07884-ES-JAD), 47 pgs.
"Complaint for Patent Infringement Exhibit 1026 for CBM Patents Part 9", 47 pgs.
"Complaint for Patent Infringement of Exhibit 1025 for CBM Patents Part 1", *Jazz Pharmaceuticals, Inc. v. Par Pharmaceuticals, Inc*, Civil Action No. 2:13-CV-07884-ES-JAD, 47pgs.
"Complaint for Patent Infringement of Exhibit 1025 for CBM Patents Part 10", *Jazz Pharmaceuticals, Inc. v. Par Pharmaceuticals, Inc*, Civil Action No. 2:13-CV-07884-ES-JAD, 41 pgs.
"Complaint for Patent Infringement of Exhibit 1025 for CBM Patents Part 2", *Jazz Pharmaceuticals, Inc. v. Par Pharmaceuticals, Inc*, Civil Action No. 2:13-CV-07884-ES-JAD, 47 pgs.
"Complaint for Patent Infringement of Exhibit 1025 for CBM Patents Part 3", *Jazz Pharmaceuticals, Inc. v. Par Pharmaceuticals, Inc*, Civil Action No. 2:13-CV-07884-ES-JAD, 47 pgs.
"Complaint for Patent Infringement of Exhibit 1025 for CBM Patents Part 4", *Jazz Pharmaceuticals, Inc. v. Par Pharmaceuticals, Inc*, Civil Action No. 2:13-CV-07884-ES-JAD, 47 pgs.
"Complaint for Patent Infringement of Exhibit 1025 for CBM Patents Part 5", *Jazz Pharmaceuticals, Inc. v. Par Pharmaceuticals, Inc*, Civil Action No. 2:13-CV-07884-ES-JAD, 47 pgs.
"Complaint for Patent Infringement of Exhibit 1025 for CBM Patents Part 6", *Jazz Pharmaceuticals, Inc. v. Par Pharmaceuticals, Inc*, Civil Action No. 2:13-CV-07884-ES-JAD, 47 pgs.
"Complaint for Patent Infringement of Exhibit 1025 for CBM Patents Part 7", *Jazz Pharmaceuticals, Inc. v. Par Pharmaceuticals, Inc*, Civil Action No. 2:13-CV-07884-ES-JAD, 47 pgs.
"Complaint for Patent Infringement of Exhibit 1025 for CBM Patents Part 8", *Jazz Pharmaceuticals, Inc. v. Par Pharmaceuticals, Inc*, Civil Action No. 2:13-CV-07884-ES-JAD, 47 pgs.
"Complaint for Patent Infringement of Exhibit 1025 for CBM Patents Part 9", *Jazz Pharmaceuticals, Inc. v. Par Pharmaceuticals, Inc*, Civil Action No. 2:13-CV-07884-ES-JAD, 47 pgs.
"Exhibit 1002 for CBM U.S. Pat. No. 7,895,059 Part 1", 51 pgs.
"Exhibit 1002 for CBM U.S. Pat. No. 7,895,059 Part 2", 51 pgs.
"Exhibit 1002 for CBM U.S. Pat. No. 7,895,059 Part 3", 51 pgs.
"Exhibit 1002 for CBM U.S. Pat. No. 7,895,059 4", 48 pgs.
"Exhibit 1016 for CBM U.S. Pat. No. 7,668,730 Part 1", 56 pgs.
"Exhibit 1016 for CBM U.S. Pat. No. 7,668,730 Part 10", 56 pgs.
"Exhibit 1016 for CBM U.S. Pat. No. 7,668,730 Part 2", 56 pgs.
"Exhibit 1016 for CBM U.S. Pat. No. 7,668,730 Part 3", 56 pgs.
"Exhibit 1016 for CBM U.S. Pat. No. 7,668,730 Part 4", 56 pgs.
"Exhibit 1016 for CBM U.S. Pat. No. 7,668,730 Part 5", 56 pgs.
"Exhibit 1016 for CBM U.S. Pat. No. 7,668,730 Part 6", 56 pgs.
"Exhibit 1016 for CBM U.S. Pat. No. 7,668,730 Part 7", 56 pgs.
"Exhibit 1016 for CBM U.S. Pat. No. 7,668,730 Part 8", 56 pgs.
"Exhibit 1016 for CBM U.S. Pat. No. 7,668,730 Part 9", 56 pgs.
"Letter from Theodora McCormick to Magistrate Judge Cathy L. Waldor Part 1", (Mar. 19, 2012), 26 pgs.
"Letter from Theodora McCormick to Magistrate Judge Cathy L. Waldor Part 2", (Mar. 19, 2012), 26 pgs.
"Letter from Theodora McCormick to Magistrate Judge Cathy L. Waldor Part 3", (Mar. 19, 2012), 26 pgs.
"Letter from Theodora McCormick to Magistrate Judge Cathy L. Waldor Part 4", (Mar. 19, 2012), 26 pgs.
"Letter from Wockhardt Bio AG regarding Paragraph IV—Part 1", Pursuant to § 505G)(2)(B)(ii) of the Fed. Food, Drug & Cosmetic Act for U.S. Patents, (Jun. 5, 2015), 35 pgs.
"Letter from Wockhardt Bio AG regarding Paragraph IV—Part 2", Pursuant to § 505G)(2)(B)(ii) of the Fed. Food, Drug & Cosmetic Act for U.S. Patents, (Jun. 5, 2015), 35 pgs.
"Letter from Wockhardt Bio AG regarding Paragraph IV—Part 3", Pursuant to § 505G)(2)(B)(ii) of the Fed. Food, Drug & Cosmetic Act for U.S. Patents, (Jun. 5, 2015), 35 pgs.
"Letter from Wockhardt Bio AG regarding Paragraph IV—Part 4", Pursuant to § 505G)(2)(B)(ii) of the Fed. Food, Drug & Cosmetic Act for U.S. Patents, (Jun. 5, 2015), 35 pgs.
"Par Pharmaceutical Inc. Certified File History Exhibit 1002 for CBM for U.S. Pat. No. 8,589,182 Part 1", 160 pgs.
"Par Pharmaceutical Inc. Certified File History Exhibit 1002 for CBM for U.S. Pat. No. 8,589,182 Part 10", 160 pgs.
"Par Pharmaceutical Inc. Certified File History Exhibit 1002 for CBM for U.S. Pat. No. 8,589,182 Part 11", 160 pgs.
"Par Pharmaceutical Inc. Certified File History Exhibit 1002 for CBM for U.S. Pat. No. 8,589,182 Part 12", 160 pgs.
"Par Pharmaceutical Inc. Certified File History Exhibit 1002 for CBM for U.S. Pat. No. 8,589,182 Part 13", 160 pgs.
"Par Pharmaceutical Inc. Certified File History Exhibit 1002 for CBM for U.S. Pat. No. 8,589,182 Part 14", 160 pgs.
"Par Pharmaceutical Inc. Certified File History Exhibit 1002 for CBM for U.S. Pat. No. 8,589,182 Part 15", 160 pgs.
"Par Pharmaceutical Inc. Certified File History Exhibit 1002 for CBM for U.S. Pat. No. 8,589,182 Part 3", 160 pgs.
"Par Pharmaceutical Inc. Certified File History Exhibit 1002 for CBM for U.S. Pat. No. 8,589,182 Part 4", 160 pgs.
"Par Pharmaceutical Inc. Certified File History Exhibit 1002 for CBM for U.S. Pat. No. 8,589,182 Part 5", 160 pgs.
"Par Pharmaceutical Inc. Certified File History Exhibit 1002 for CBM for U.S. Pat. No. 8,589,182 Part 6", 160 pgs.
"Par Pharmaceutical Inc. Certified File History Exhibit 1002 for CBM for U.S. Pat. No. 8,589,182 Part 7", 160 pgs.
"Par Pharmaceutical Inc. Certified File History Exhibit 1002 for CBM for U.S. Pat. No. 8,589,182 Part 8", 160 pgs.
"Par Pharmaceutical Inc. Certified File History Exhibit 1002 for CBM for U.S. Pat. No. 8,589,182 Part 9", 160 pgs.
"Par Pharmaceutical, Inc. Certified File History Exhibit 1002 for CBM for U.S. Pat. No. 8,589,182 Part 2", 160 pgs.
"Par Pharmaceutical, Inc. Certified File History of Exhibit 1016 for CBM for U.S. Pat. No. 7,668,730 Part 1", 137 pgs.

(56) References Cited

OTHER PUBLICATIONS

"Par Pharmaceutical, Inc. Certified File History of Exhibit 1016 for CBM for U.S. Pat. No. 7,668,730 Part 2", 137 pgs.
"Par Pharmaceutical, Inc. Certified File History of Exhibit 1016 for CBM for U.S. Pat. No. 7,668,730 Part 3", 137 pgs.
"Par Pharmaceutical, Inc. Certified File History of Exhibit 1016 for CBM for U.S. Pat. No. 7,668,730 Part 4", 137 pgs.
"Par Pharmaceutical, Inc. Certified FileHistory of Exhibit 1016 for CBM for U.S. Pat. No. 7,668,730 Part 5", 133 pgs.
"Roxane Laboratories, Inc. File History Exhibit 1016 for CBM for U.S. Pat. No. 7,765,106 Part 1", 56 pgs.
"Roxane Laboratories, Inc. File History Exhibit 1016 for CBM for U.S. Pat. No. 7,765,106 Part 10", 56 pgs.
"Roxane Laboratories, Inc. File History Exhibit 1016 for CBM for U.S. Pat. No. 7,765,106 Part 2", 56 pgs.
"Roxane Laboratories, Inc. File History Exhibit 1016 for CBM for U.S. Pat. No. 7,765,106 Part 3", 56 pgs.
"Roxane Laboratories, Inc. File History Exhibit 1016 for CBM for U.S. Pat. No. 7,765,106 Part 4", 56 pgs.
"Roxane Laboratories, Inc. File History Exhibit 1016 for CBM for U.S. Pat. No. 7,765,106 Part 5", 56 pgs.
"Roxane Laboratories, Inc. File History Exhibit 1016 for CBM for U.S. Pat. No. 7,765,106 Part 6", 56 pgs.
"Roxane Laboratories, Inc. File History Exhibit 1016 for CBM for U.S. Pat. No. 7,765,106 Part 7", 56 pgs.
"Roxane Laboratories, Inc. File History Exhibit 1016 for CBM for U.S. Pat. No. 7,765,106 Part 8", 56 pgs.
"Roxane Laboratories, Inc. File History Exhibit 1016 for CBM for U.S. Pat. No. 7,765,106 Part 9", 56 pgs.
Korfhage, Robert R, "Information Storage and Retrieval Part 1", Wiley Computer-Publishing, (1997), 184 pgs.
Korfhage, Robert R, "Information Storage and Retrieval Part 2", Wiley Computer Publishing, (1997), 184 pgs.
"U.S. Appl. No. 15/014,831, Response filed May 12, 2021 to Non Final Office Action dated Mar. 8, 2021", 19 pgs.
"U.S. Appl. No. 15/014,831, Examiner Interview Summary dated May 27, 2021", 2 pgs.
"Answer to Complaint for Patent Infringement, Defenses and Counterclaims", C.A. No. 21-691-MN Document 11, *Jazz Pharmaceuticals, Inc.*, v. *Avadel Pharmaceuticals PLC*, (Jun. 3, 2021), 51 pgs.
"U.S. Appl. No. 15/057,898, Response filed Jul. 19, 2021 to Final Office Action dated May 5, 2021", 24 pgs.
"U.S. Appl. No. 17/209,608, Preliminary Amendment filed Jul. 20, 2021", 16 pgs.
U.S. Appl. No. 17/061,783, filed Oct. 2, 2020, Sensitive Drug Distribution Systems and Methods.
U.S. Appl. No. 16/826,909, filed Mar. 23, 2020, Sensitive Drug Distribution Systems and Methods.
U.S. Appl. No. 17/209,608, filed Mar. 23, 2021, Sensitive Drug Distribution Systems and Methods.
"U.S. Appl. No. 15/057,898, Non Final Office Action dated Nov. 8, 2021", 13 pgs.
"U.S. Appl. No. 15/014,831, Response filed Nov. 9, 2021 to Final Office Action dated Aug. 20, 2021", 16 pgs.
"U.S. Appl. No. 15/014,831, Non Final Office Action dated Nov. 30, 2021", 36 pgs.
Cicero, "The Development of a Comprehensive Risk-Management Program for Prescription Opioid Analgesics: Researched Abuse, Diversion and Addiction-Related Surveillance (RADARS)", Pain Medicine, vol. 8, Issue 2, (Mar. 2007), 157-170.
"U.S. Appl. No. 15/014,831, Response filed Mar. 30, 2022 to Non Final Office Action dated Nov. 30, 2021", 22 pgs.
"U.S. Appl. No. 15/014,831, Final Office Action dated Apr. 29, 2022", 34 pgs.
"U.S. Appl. No. 15/057,898, Examiner Interview Summary dated Apr. 8, 2022", 2 pgs.
"U.S. Appl. No. 15/057,898, Response filed Apr. 8, 2022 to Non Final Office Action dated Nov. 8, 2021", 20 pgs.
"U.S. Appl. No. 16/826,909, Restriction Requirement dated May 25, 2022", 5 pgs.
"Application Serial No. 15/014,831, Response filed Jul. 8, 2022 to Final Office Action dated Apr. 29, 2022", 16 pgs.
"U.S. Appl. No. 15/057,898, Final Office Action dated Aug. 1, 2022", 14 pgs.
"U.S. Appl. No. 16/826,909, Response filed Jul. 12, 2022 to Restriction Requirement dated May 25, 2022", 13 pgs.
"U.S. Appl. No. 17/061,783, Non Final Office Action dated Jul. 21, 2022", 40 pgs.
Pham, Tammy, et al., "Household Diversion of Prescription Stimulants: Medication Misuse by Parents of Children with Attention-Deficit/Hyperactivity Disorder", J Child Adolesc Psychopharmacol, (2017), 2 pgs.

\* cited by examiner

PRESCRIPTION AND ENROLLMENT FORM

← 600

PRESCRIBER INFORMATION

PRESCRIBER'S NAME: _____ OFFICE CONTACT: _____
STREET ADDRESS: _____
CITY: _____ STATE: _____ ZIP: _____
PHONE: _____ FAX: _____
LICENSE NUMBER: _____ DEA NUMBER: _____
MD SPECIALTY: _____

PRESCRIPTION FORM

PATIENT NAME: _____ SS#: _____ DOB: _____ SEX M / F
ADDRESS: _____
CITY: _____ STATE: _____ ZIP: _____
Rx: XYREM ORAL SOLUTION (500 mg/mL) 180 ML. BOTTLE QUANTITY: _____ MONTHS SUPPLY
SIG: TAKE _____ GMS P.O. DILUTED IN 60 mL WATER AT H.S. AND THEN AGAIN 2 1/2 TO 4 HOURS LATER
REFILLS (CIRCLE ONE): 0 1 2 (MAXIMUM OF 3 MONTH SUPPLY)
_____ DATE: ____/____/____
PRESCRIBER'S SIGNATURE

| PHYSICIAN DECLARATION—PLEASE CHECK EACH BOX | TO BE COMPLETED AT INITIAL PRESCRIPTION ONLY |

☐ I HAVE READ THE MATERIALS IN THE XYREM PHYSICIAN SUCCESS PROGRAM
☐ I VERIFY THAT THE PATIENT HAS BEEN EDUCATED WITH RESPECT TO XYREM PREPARATION, DOSING AND SCHEDULING.
☐ I UNDERSTAND THAT XYREM IS APPROVED FOR THE TREATMENT OF CATAPLEXY IN PATIENTS WITH NARCOLEPSY, AND THAT SAFETY OR EFFICACY HAS NOT BEEN ESTABLISHED FOR ANY OTHER INDICATION.
☐ I UNDERSTAND THAT THE SAFETY OF DOSES GREATER THAN 9gm/DAY HAS NOT BEEN ESTABLISHED

PATIENT INFORMATION

BEST TIME TO CONTACT PATIENT: ☐ DAY ☐ NIGHT
DAY #: _____ EVENING #: _____
INSURANCE COMPANY NAME: _____ PHONE #: _____
INSURED'S NAME: _____ RELATIONSHIP TO PATIENT: _____
IDENTIFICATION NUMBER: _____ POLICY/GROUP NUMBER: _____
PRESCRIPTION CARD: ☐ NO ☐ YES IF YES, CARRIER: _____ POLICY #: _____ GROUP: _____
PLEASE ATTACH COPIES OF PATIENT'S INSURANCE CARDS

CAREGIVER INFORMATION

BEST TIME TO CONTACT CAREGIVER: ☐ DAY ☐ NIGHT
DAY #: _____ EVENING #: _____
INSURANCE COMPANY NAME: _____ PHONE #: _____
INSURED'S NAME: _____ RELATIONSHIP TO CAREGIVER: _____
IDENTIFICATION NUMBER: _____ POLICY/GROUP NUMBER: _____
PRESCRIPTION CARD: ☐ NO ☐ YES IF YES, CARRIER: _____ POLICY #: _____ GROUP: _____
PLEASE ATTACH COPIES OF CAREGIVER'S INSURANCE CARDS

FAX COMPLETED FORM TO XYREM SUCCESS PROGRAM (TOLL-FREE) 1-866-470-1744
FOR INFORMATION, CALL THE XYREM TEAM (TOLL FREE) AT 1-866-XYREM88 (1-866-997-3688)

FIG. 6

PATIENT ASSISTANCE APPLICATION REQUEST FORM

DATE:

TO: PATIENT ASSISTANCE ORGANIZATION
FROM: SDS

FAX #: 203-798-2291

PLEASE SEND A XYREM PATIENT ASSISTANCE PROGRAM APPLICATION TO:

PATIENT NAME _____

ADDRESS _____

_____

TELEPHONE: ( ) _____

PATIENT DOSAGE: _____ (GRAMS) TWICE NIGHTLY FOR A TOTAL DOSAGE OF _____ (GRAMS) _____ BOTTLES (THREE MONTHS SUPPLY)

BACKGROUND INFORMATION:

_____

_____

_____

_____

_____

CAREGIVER NAME _____

ADDRESS _____

_____

TELEPHONE: ( ) _____

SENSITIVE DRUG PATIENT ASSISTANCE PROGRAM
VOUCHER REQUEST FOR MEDICATION

PATIENT INFORMATION
<FIRST NAME><LAST NAME>
<ADDRESS 1>
<ADDRESS 2>
<CITY, STATE ZIP CODE>

PHONE: <123-456-7890
DOB: 01/01/1900
SSN: 123-45-6789
DRUG ALLOTMENT: 100%
LRD: 03/01/2001

CAREGIVER INFORMATION
<FIRST NAME><LAST NAME>
<ADDRESS 1>
<ADDRESS 2>
<CITY, STATE ZIP CODE>

CASE CODE: ********

PHYSICIAN INFORMATION
<PHYSICIAN NAME>
<ADDRESS 1>
<ADDRESS 2>
<CITY, STATE ZIP CODE>

PHONE: <123-456-7890

FIRST SHIPMENT THIS YEAR

| DRUG | QUANTITY |
|---|---|
| XYREEM 180ml btl | 1 |

VALIDATION DATE:   03/01/2001
EXPIRATION DATE:   05/31/2001
ISSUE DATE:        03/15/2001

APPROVED _____

*PHARMACY USE*

NORD COPY
********************************************************
(DETACH HERE)

PATIENT INFORMATION
<FIRST NAME><LAST NAME>
<ADDRESS 1>
<ADDRESS 2>
<CITY, STATE ZIP CODE>

PHONE: <123-456-7890
DOB: 01/01/1900
SSN: 123-45-6789
DRUG ALLOTMENT: 100%
LRD: 03/01/2001

CAREGIVER INFORMATION
<FIRST NAME><LAST NAME>
<ADDRESS 1>
<ADDRESS 2>
<CITY, STATE ZIP CODE>

CASE CODE: ********

PHYSICIAN INFORMATION
<PHYSICIAN NAME>
<ADDRESS 1>
<ADDRESS 2>
<CITY, STATE ZIP CODE>

PHONE: <123-456-7890

FIRST SHIPMENT THIS YEAR

| DRUG | QUANTITY |
|---|---|
| XYREM 180ml btl | 1 |

VALIDATION DATE:   03/01/2001
EXPIRATION DATE:   05/31/2001
ISSUE DATE:        03/15/2001

APPROVED _____

*PHARMACY USE*

FIG. 8

SENSITIVE DRUG PHYSICIAN'S CERTIFICATE OF MEDICAL NEED

900

PATIENT INFORMATION

DATE: _____

NAME: _____
      LAST                       FIRST                        M

DATE OF BIRTH: _____

PATIENT INFORMATION

CAREGIVER INFORMATION

DATE: _____

NAME: _____
      LAST                       FIRST                        M

DATE OF BIRTH: _____

DRUG BEING PRESCRIBED: XYREM

DIAGNOSIS/CONDITION FOR WHICH DRUG IS BEING PRESCRIBED: _____

ICD-9: _____

PHYSICIAN INFORMATION

PHYSICIAN'S NAME (PLEASE PRINT): _____

PHYSICIAN'S SIGNATURE: _____  DATE: _____

PLEASE FAX BACK TO SENSITIVE DRUG SUCCESS PROGRAM: (1-800-TOLL FREE NUMBER)

FIG. 9

ACTIVITY REPORTS

| | REPORT FREQUENCY | | |
|---|---|---|---|
| | WEEKLY | MONTHLY | QUARTERLY |
| SALES | | | |
| Rx BY ZIP (NEW AND TOTAL) | X | X | X |
| Rx BY PHYSICIAN BY ZIP | X | X | |
| $ BY ZIP | X | X | X |
| REGULATORY | | | |
| # OF PHYSICIAN REGISTRIES | | X | |
| # OF DENIED PHYSICIAN REGISTRIES AND REASON | | X | |
| # OF COMPLETED PATIENT REGISTRIES | | X | |
| # OF PROBLEM IDENTIFICATION & MANAGEMENT RISK DIVERSION REPORTS COMPLETED | X | | |
| # OF CYCLE COUNTS PERFORMED & ACCURACY OF EACH | | X | |
| QUALITY ASSURANCE | | | |
| # OF PRODUCT DEFECTS/COMPLAINTS REPORTED, TYPE AND LOT # | | X | |
| CALL CENTER | | | |
| # OF CALLS RECEIVED | | X | |
| # OF CALLS INITIATED | | X | |
| # OF CALLS ANSWERED IN 30 SECONDS, ETC. | | X | |
| PERCENTAGE OF CALLS ANSWERED IN 30 SECONDS | | X | |
| # OF ABANDONED CALLS | | X | |
| % OF ABANDONED CALLS | | X | |
| AVERAGE CALL LENGTH | | X | |
| PHARMACY | | | |
| # OF FAXED Rx/ENROLLMENT FORMS | | X | |
| # OF MAILED Rx/ENROLLMENT FORMS | | X | |
| # OF RxS SHIPPED W/IN 1, 2, 3, 4 ETC. DAYS (FROM THE TIME INITIAL RECEIPT TO SHIPMENT OF Rx) | | X | |
| # OF PATIENT SUCCESS PACKETS SHIPPED | | X | |

FIG. 10A

| ACTIVITY REPORTS | | |
|---|---|---|
| PHARMACY | | |
| # OF PHYSICIAN SUCCESS PACKETS SHIPPED | | X |
| # OF COMPLETED SHIPMENTS | | X |
| # OF INCOMPLETE SHIPMENTS AND REASON | | X |
| # OF SHIPPING ERRORS | | X |
| # OF PAP SHIPMENTS | | X |
| # OF PAP APPLICATIONS | | X |
| # OF PAP APPROVALS | | X |
| # OF CANCELED ORDERS | | X |
| # OF USPS ERRORS | | X |
| INVENTORY | | |
| # OF RETURNED PRODUCTS AND REASON | | X |
| # OF OUTDATED BOTTLES OF PRODUCT | | X |
| INVENTORY COUNTS OF CONSIGNMENT & PRODUCTION INVENTORY | | X |
| # OF UNITS RECEIVED | | X |
| LOTS RECEIVED | | X |
| REIMBURSEMENT | | |
| # OF PENDED AND WHY | | X |
| # OF APPROVALS | | X |
| # OF DENIALS | | X |
| # OF REJECTIONS | | X |
| PAYOR TYPES | | X |

FIG. 10B

| ACTIVITY REPORTS | | |
|---|---|---|
| PATIENT CARE | | |
| # OF ADVERSE EVENTS REPORTED AND TYPE | | X |
| # OF ADVERSE EVENTS SENT TO OMI | | X |
| # OF DOSING PROBLEMS AND TYPE | | X |
| # OF NONCOMPLIANCE EPISODES AND REASON | | X |
| # OF PATIENT COUNSELED AND REASON | | X |
| # OF PATIENTS DISCONTINUED AND REASON | | X |
| PATIENT CARE | | |
| # OF PATIENTS REFERRED TO PHYSICIAN AND REASON | | X |
| # OF ACTIVE PATIENTS | | X |
| # OF NEW PATIENTS | | X |
| # OF RESTART PATIENTS | | X |
| # OF DISCONTINUED PATIENTS AND REASON | | X |
| DRUG INFORMATION | | |
| # OF DRUG INFORMATION REQUESTS AND TYPE | | X |
| # OF CALLS TRIAGED TO OMI | | X |

FIG. 10C

SENSITIVE DRUG DISTRIBUTION SYSTEMS AND METHODS

RELATED APPLICATIONS

This application claims priority to U.S. Provisional Application No. 62/534,892, filed on Jul. 20, 2017, and claims priority to U.S. Provisional Application No. 62/607,221, filed on Dec. 18, 2017, both of which are related to U.S. Serial application Ser. No. 14/196,603, filed on Mar. 4, 2014, which is a Continuation of and claims priority to U.S. Serial application Ser. No. 13/592,202, filed on Aug. 22, 2012 and issued on May 20, 2014 as U.S. Pat. No. 8,731,963, which is a Continuation of and claims priority to U.S. application Ser. No. 13/013,680, filed on Jan. 25, 2011, which is a Continuation of and claims priority to U.S. application Ser. No. 12/704,097, filed on Feb. 11, 2010 and issued on Feb. 22, 2011 as U.S. Pat. No. 7,895,059, which is a Continuation of and claims priority to U.S. application Ser. No. 10/322,348, filed on Dec. 17, 2002 and issued on Feb. 23, 2010 as U.S. Pat. No. 7,668,730, which applications are herein incorporated by reference in their entirety.

TECHNICAL FIELD

The technical field generally relates to the distribution of drugs, and in particular, to the distribution of sensitive drugs to pediatric patients. Additionally, an embodiment relates to using an exclusive pediatric database to monitor and control the distribution of sensitive drugs to pediatric patients.

BACKGROUND

Sensitive drugs are controlled to minimize risk and ensure that they are not abused, or cause adverse reactions. Such sensitive drugs are approved for specific uses by the Food and Drug Administration, and must be prescribed by a licensed physician in order to be purchased by consumers. Some drugs, such as cocaine and other common street drugs are the object of abuse and illegal schemes to distribute for profit. Some schemes include doctor shopping, diversion, and pharmacy thefts. A locked cabinet or safe is a requirement for distribution of some drugs.

Certain agents, such as gamma hydroxy buterate (GHB) are also abused, yet also are effective for therapeutic purposes such as treatment of daytime cataplexy in patients with narcolepsy. Some patients however, will obtain prescriptions from multiple doctors, and have them filled at different pharmacies. Still further, an unscrupulous physician may actually write multiple prescriptions for a patient, or multiple patients, who use cash to pay for the drugs. These patients will then sell the drug to dealers or others for profit.

There is a need for a distribution system and method that directly addresses these abuses. There is a further need for such a system and method that provides education and limits the potential for such abuses.

SUMMARY

A drug distribution system and method utilizes a central pharmacy and database to track all prescriptions for a sensitive drug that is distributed to pediatric patients (or elderly or other special needs patients). Information is kept in a central database regarding all physicians allowed to prescribe the sensitive drug, all patients receiving the drug, and all caregivers associated with pediatric patients (or elderly or other special needs patients). Abuses are identified by monitoring data in the database for prescription patterns by physicians and prescriptions obtained by patients and/or caregivers. Further verification is made that the physician is eligible to prescribe the drug by consulting a separate database for a valid DEA license, and optionally state medical boards to determine whether any corrective or approved disciplinary actions relating to controlled substances have been brought against the physician. Multiple controls beyond those for traditional drugs are imposed on the distribution depending on the sensitivity of the drug.

Education is provided to the physician, patient, and caregiver. Prior to shipping the drug for the first time, the patient and caregiver are contacted to ensure that product- and abuse-related educational materials have been received and/or read. The patient and/or caregiver may provide the name of a designee to the central pharmacy who is authorized to accept shipment of the drug. Receipt of the initial drug shipment is confirmed by contacting the patient and/or caregiver. Either a phone call or other communication to the patient and/or caregiver within a set time after delivery may be made to ensure receipt. Further, a courier service's tracking system is used to confirm delivery in additional embodiments. If a shipment is lost, an investigation is launched to find it.

Prescription refills are permitted in the number specified in the original prescription. In addition, if a prescription refill is requested by the patient and/or caregiver prior to the anticipated due date, such refills will be questioned. A lost, stolen, destroyed or spilled prescription/supply is documented and replaced to the extent necessary to honor the prescription, and will also cause a review or full investigation.

An exclusive central database that is associated with the central pharmacy contains all relevant data related to distribution of the drug and the process of distributing it, including patient, caregiver, physician, and prescription information. Several queries and reports are run against the database to provide information which might reveal potential abuse of the sensitive drug, such as early refills.

BRIEF DESCRIPTION OF THE DRAWINGS

FIG. 6 is a copy of one example prescription and enrollment form.

FIG. 8 is a copy of one example voucher request for medication for use with the NORD application request form of FIG. 7.

FIG. 9 is a copy of certificate of medical need.

FIGS. 10A, 10B and 10C are descriptions of sample reports obtained by querying a central database having fields represented in FIG. 4.

DETAILED DESCRIPTION

Figure 1:
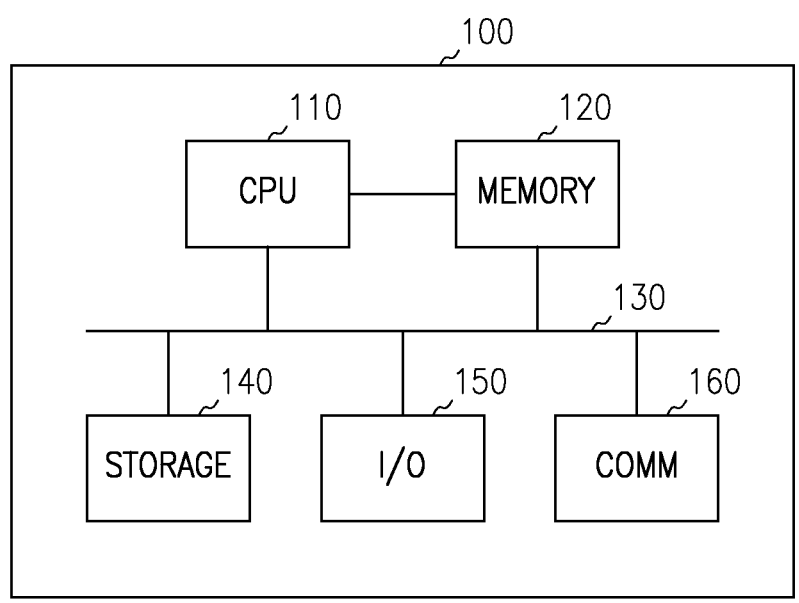
FIG. 1 is a block diagram of a computer system for use in implementing a sensitive drug distribution system.

In the following description, reference is made to the accompanying drawings that form a part hereof, and in which is shown by way of illustration specific embodiments in which the invention may be practiced. These embodiments are described in sufficient detail to enable those of ordinary skill in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

The functions or algorithms described herein are implemented in software or a combination of software and human implemented procedures in one embodiment. The software comprises computer executable instructions stored on computer readable media such as memory or other types of storage devices. The term "computer readable media" is also used to represent carrier waves on which the software is transmitted. Further, such functions correspond to modules, which are software, hardware, firmware of any combination thereof. Multiple functions are performed in one or more modules as desired, and the embodiments described are merely examples. The software is executed on a digital signal processor, ASIC, microprocessor, or other type of processor operating on a computer system, such as a personal computer, server or other computer system.

A sensitive drug is one which can be abused, or has addiction properties or other properties that render the drug sensitive. One example of such a drug is sodium oxybate, also known as gamma hydroxy butyrate (GHB $C_4H_7NaO_3$), which is useful for treatment of cataplexy in patients with narcolepsy. GHB is marketed under the trademark of Xyrem® (sodium oxybate oral solution), which trademark can be used interchangeably with GHB herein. Sensitive drugs also include narcotics or other drugs which require controls on their distribution and use to monitor behaviors to prevent abuse and adverse side effects.

In one embodiment, Xyrem® is subject to a restricted distribution program. One aspect of the program is to educate physicians and patients about the risks and benefits of Xyrem®, including support via ongoing contact with patients and a toll free helpline. Initial prescriptions are filled only after a prescriber and patient have received and read the educational materials. Further, patient, caregiver (who is associated with a pediatric, elderly, or other special needs patient), and prescribing physician registries are maintained and monitored to ensure proper distribution.

In a further embodiment, bulk sodium oxybate is manufactured at a single site, as is the finished drug product. Following manufacture of the drug product, it is stored at a facility compliant with FDA Schedule III regulations, where a consignment inventory is maintained. The inventory is owned by a company, and is managed by a central pharmacy, which uses an exclusive central computer database and which maintains the consignment inventory. Xyrem® is distributed and dispensed through a primary and exclusive central pharmacy, which as noted uses an exclusive central database, and is not stocked in retail pharmacy outlets. It is distributed by overnight carriers, or by US mail in one embodiment to potentially invoke mail fraud laws if attempts of abuse occur.

FIG. 1 is a simplified block diagram of a computer system 100, such as a personal computer for implementing at least a portion of the methods described herein. A central processing unit (CPU) 110 executes computer programs stored on a memory 120. Memory 120 in one embodiment comprises one or more levels of cache as desired to speed execution of the program and access to data on which the programs operate. The CPU is directly coupled to memory 120 in one embodiment. Both CPU 110 and memory 120 are coupled to a bus 130. A storage 140, I/O 150 and communications 160 are also coupled to the bus 130. Storage 140 is usually a long term storage device, such as a disk drive, tape drive, DVD, CD or other type of storage device. In one embodiment, storage 140 is used to house a database for use with one or more embodiments of the present invention. I/O 150 comprises keyboards, sound devices, displays and other mechanisms by which a user interacts with the computer system 100. Communications 160 comprise a network, phone connection, local area network, wide area network or other mechanisms for communicating with external devices. Such external devices comprise servers, other peer computers and other devices. In one embodiment, such external device comprises a database server that is used in place of the database on storage 140. Other computer system architectures capable of executing software and interacting with a database and users may also be used. Appropriate security measures such as encryption are used to ensure confidentiality. Further, data integrity and backup measures are also used to prevent data loss.

In many instances, a sensitive drug, such as Xyrem®, must be distributed under an umbrella of a Risk Evaluation and Mitigation Strategy (REMS) program. A purpose of a REMS program is to mitigate the risks of serious adverse outcomes resulting from inappropriate prescribing, misuse, abuse, and/or diversion of the sensitive prescription drug, such as Xyrem®, which as noted above, is used for the treatment of cataplexy in patients with narcolepsy and for the treatment of excessive daytime sleepiness (EDS) in patients with narcolepsy. This goal is achieved by 1) informing prescribers, pharmacists, patients, and caregivers of the risks, contraindications, potential for abuse, misuse, and overdose, and the safe use, handling, and storage of the sensitive drug, and 2) ensuring that central pharmacy controls exist prior to filling prescriptions, wherein the controls screen for concomitant use of sedative hypnotics and other potentially interacting agents, monitor for inappropriate prescribing, and monitor and notify prescribers about concomitant use of contraindicated medications or signs of potential abuse, misuse, and/or diversion. One feature of such a REMS program is a single, certified, central pharmacy, and its associated exclusive computer database, that handles all prescription requests, written by all prescribers, for all patients being prescribed the sensitive drug. To become certified, all pharmacy staff and pharmacists of the central pharmacy must have completed a REMS pharmacy training program. The exclusive central database contains information about patient, caregiver, and prescriber enrollments, prescriptions for sensitive drugs, sensitive drug shipments, and Risk Management Reports (RMRs) generated by the certified, central pharmacy whenever there is activity raising a suspicion of abuse, misuse, and/or diversion, including requests for early refills.

All patients must be enrolled in the REMS program before they can receive a sensitive drug shipment. Additionally, as noted below in connection with FIG. 2, an enrolled prescriber completes an enrollment form for the patient and submits the form to the REMS program for processing and completion of enrollment. This form provides the patient's demographic and insurance information, links an enrolled prescriber to an enrolled patient, and verifies that specified requirements have been met, including an acknowledgment that the prescriber has counseled the patient on the serious risks and safe use of the sensitive drug. This information is entered into the exclusive database of the certified, central pharmacy, thereby allowing the pharmacy to verify that the patient is enrolled as part of its validation process prior to dispensing the sensitive drug. Additionally, all prescriptions for the sensitive drug go directly from an enrolled prescriber to the REMS Program, which limits an individual's ability to forge prescriptions or secure uncontrolled amounts of the sensitive drug with multiple prescriptions from different prescribers. As a further precaution, the sensitive drug prescription form is only available directly from the REMS program, not indirectly from the REMS website or other secondary source. The prescriber is notified once a patient is successfully enrolled and can be prescribed the sensitive drug.

Prescribers are considered to be enrolled in the REMS program only after verification that the prescriber enrollment form has been completed and the requirements described on the form have been met. Enrollment information is entered into the exclusive database of the certified, central pharmacy so that the pharmacy can verify that the prescriber is enrolled in the REMS program as part of its validation process prior to accepting a sensitive drug prescription or dispensing the sensitive drug. The certified, central pharmacy fills prescriptions only from prescribers who have completed enrollment in the REMS program. Prescribers are not enrolled (and therefore their patients cannot receive the sensitive drug) until the prescribers verify that they have reviewed educational materials and understand the approved indications and risks of the sensitive drug and complete the prescriber enrollment form. Upon receipt of an initial prescription, the certified, central pharmacy checks the exclusive database to ensure that the prescriber is enrolled. If the prescriber is enrolled, the certified, central pharmacy will verify the prescriber's name, DEA number, and state license number using appropriate sources. The DEA and license confirmation ensures that only prescriptions from enrolled prescribers who can legally prescribe a controlled substance are filled.

The certified, central pharmacy tracks each shipment of the sensitive drug through a carrier's or delivery service's website to confirm shipment within a particular time frame, such as one business day. Tracking reports are generated to confirm the receipt of orders shipped during the previous 48 hours. If an order is not delivered on the initial attempt, the carrier can make multiple attempts to redeliver. If redelivery attempts are not successful, the carrier returns the shipment to the certified, central pharmacy, per its arrangement with the pharmacy. The returned product is inspected for evidence of damage or tampering, and it is noted in the exclusive database whether the product is acceptable for reshipment (only applicable if the product has not been delivered and has remained in the carrier's possession and reshipment is only to the same patient). In the event a shipment is lost by the carrier, a replacement shipment cannot be sent until approved by a pharmacist-in-charge at the certified, central pharmacy.

The certified, central pharmacy ensures that only one sensitive drug prescription is being dispensed at any one time to any one patient. Because the certified, central pharmacy contacts the prescriber to renew a prescription before the previous prescription has expired (to ensure continuity of treatment for the patient), new prescriptions often arrive before the current prescription has expired. When a new prescription arrives for a patient who already has an active prescription, the new prescription is put on hold until the prescription already in the exclusive database is depleted. If the certified, central pharmacy receives a prescription for a patient from more than one prescriber, certified, central pharmacy staff will know that the patient already has an active prescription in the exclusive database and will query the patient as to the reason for having more than one prescriber write prescriptions for the patient. If the patient has more than one prescription from more than one prescriber, the certified, central pharmacy will contact each prescriber for clarification. Depending on the clarification received from the different prescribers, the certified, central pharmacy will either terminate the current prescription prior to activating the new one or will put the new prescription on hold until the current prescription has been depleted. If there is a reasonable suspicion that a patient may be doctor shopping for purposes of abuse, misuse, and/or diversion, the prescription will not be filled, the prescriber(s) will be alerted, and the pharmacist at the certified, central pharmacy will complete an RMR.

Upon receipt of the initial prescription for every patient, the certified, central pharmacy verifies the patient's enrollment and checks the patient's profile in the exclusive database to ensure the patient has not previously enrolled. For each initial prescription, at the time of data entry, the certified, central pharmacy searches the database by last name, city and state, social security number (if provided), and date of birth to verify patient enrollment status. If there are no matches, the pharmacy will proceed with processing this patient as a new enrollment. In some instances, a patient may be enrolled under more than one name (for example, if the patient's name changes because of marriage). When a duplicate patient profile is detected, the certified, central pharmacy ensures that only one profile is active and eligible to receive shipments.

The certified, central pharmacy does not allow shipment to patients who have not enrolled in or have been removed from the REMS program or have stopped treatment using the sensitive drug. Upon receipt of each initial prescription, the certified, central pharmacy checks the enrollment status of each patient and prescriber. At each refill, the certified, central pharmacy contacts the patient to update the patient profile in the exclusive database, which provides another check on enrollment status.

As noted above, a tool used at the certified, central pharmacy to monitor for inappropriate prescribing, misuse, abuse, and/or diversion of the sensitive drug is a risk management report (RMR). Investigations into potential abuse, misuse, and/or diversion can be made a requirement of the REMS program, and the RMR procedures can be a requirement included in the certified, central pharmacy's elements to assure safe use (ETASU) of the REMS program. A pharmacist at the certified, central pharmacy must complete an RMR for any event that gives rise to a reasonable suspicion of abuse, misuse, and/or diversion of the sensitive drug. This includes all requests for an early refill, reports of potential misuse, abuse, and/or diversion, and all reports of lost, stolen, destroyed, or spilled drug.

A completed RMR includes patient identifier and profile information, the date of the event, a descriptive narrative of the event, a record of the certified, central pharmacy contact(s) with the prescriber related to the event, the outcome(s) of the event including any action taken by the certified, central pharmacy related to the event, and a list of any documents or reports related to the event (e.g., adverse event reports, police reports, DEA reports for lost shipments, and/or fire reports). In many cases, RMRs will document investigations that include multiple pharmacy-patient, pharmacy-caregiver, and/or pharmacy-prescriber interactions that transpire over several days. The completed RMR provides a concise compilation of relevant information associated with a potential risk event, and when documented in the exclusive database, provides longitudinal data that the certified, central pharmacy can consult to determine whether a patient's pattern of behavior indicates a likelihood of abuse, misuse, and/or diversion.

The RMR history for each enrolled patient who is receiving a sensitive drug from the certified, central pharmacy is available for consultation and review at the pharmacy, and this review is required as part of a pharmacist's handling of an early refill request or any time the pharmacist suspects abuse, misuse, and/or diversion of the sensitive drug. In addition, the REMS program requires that the pharmacist at the certified, central pharmacy notifies a prescriber in the event of suspected abuse, misuse, and/or diversion of the drug and when a patient has requested an early refill. Any information contained in a patient's RMR history provides an organized summary of previous patient experiences and problems with the drug that can be reviewed with the prescriber to ensure awareness of individual patient behaviors and the possible need for additional patient counseling or other actions, ranging from restrictions on early refills to removal from the REMS program.

Alerts on a patient's and/or caregiver's profile stored in the exclusive database help to direct any subsequent interaction with the patient and/or alert all pharmacy staff of the certified, central pharmacy that this patient or caregiver has a history of potential abuse, misuse, and/or diversion of the sensitive drug and that requests for early refills or reports of lost or stolen drug or other irregularities should be met with greater scrutiny. In the event that a patient changes his or her prescriber, the certified, central pharmacy provides longitudinal information about the patient, including any relevant alerts, to the new prescriber. In addition, pharmacists at the certified, central pharmacy review prior alerts as part of the RMR procedure, ensuring that both the prescriber and pharmacist are aware of a patient's and/or caregiver's history of possible abuse, misuse, and/or diversion.

An early refill request occurs when a patient, caregiver, and/or prescriber report that the patient will not have sufficient quantities of the sensitive drug to last until the next scheduled shipment, and therefore will require drug to be shipped sooner than scheduled. Early refill requests do not include changes to scheduling that are a result of shipment logistics, such as the carrier not shipping on weekends and holidays. In these cases, the product is delivered prior to a patient's next shipment date, but the patient's subsequent refill date does not shift to ensure the patient does not receive more than is prescribed.

The pharmacist at the certified, central pharmacy is required to complete an RMR for every early refill request, notify the prescriber of the request, and monitor a patient's and/or caregiver's history of early refill requests as part of the required monitoring of patients and/or caregivers for abuse, misuse, and/or diversion of the sensitive drug.

Under the REMS program, prescribers are notified regarding concomitant use of contraindicated medications and serious changes in the patient's medical condition. Notifications are documented in the certified, central pharmacy exclusive database. As noted, the REMS program also documents the number of notifications to prescribers for suspected abuse, misuse, and/or diversion, for alerts regarding potential abuse, misuse, and/or diversion on the patient's profile; for early refill requests; and for prescription errors in a way that is accessible for reporting.

Pharmacists at the certified, central pharmacy are required to notify the prescriber of every early refill request. As early refill requests, including repeated requests, may be a sign of abuse, misuse, and/or diversion, pharmacists are required to review the patient's and/or caregiver's RMR history and any alerts, and ensure that the request has been discussed with the prescriber prior to approving the early refill.

To ensure that the informational objectives of the REMS program are achieved, the REMS program requires all prescribers and the certified, central pharmacy to become specially certified in the REMS program, and further requires all patients and caregivers to enroll in the REMS program. Briefly, prescriber certification requires each prescriber to attest that that he or she has read the prescribing information and a REMS program prescriber brochure, and pharmacy certification requires that the pharmacy must, among other things, ensure that all pharmacists complete a REMS program certified pharmacy training program. The pharmacy training program ensures that all pharmacy staff are trained on the risks, safe use, handling, and storage of the sensitive drug and on the requirements of the REMS program, including completing knowledge assessments. The review of these educational and training materials ensures that all prescribers and pharmacists are informed of the risks and safe use of the sensitive drug. Patient and caregiver enrollment (or an association of the caregiver with the patient) requires that patients and caregivers be informed, during the enrollment process by their prescriber, of the risks of the sensitive drug. This informing can be by way of the information contained in a REMS program patient quick start guide, a medication guide, a caregiver brochure that is specific to pediatric patients (or elderly or other special needs patients), and through completion of a REMS program counseling checklist.

Regarding the counseling checklist, prior to dispensing the sensitive drug, a pharmacist at the certified, central pharmacy contacts the patient and completes the REMS program patient counseling checklist, and ensures that the information received is maintained in the REMS program exclusive database of the certified, central pharmacy. The REMS program patient counseling checklist is the primary tool used by the certified, central pharmacy to counsel newly enrolled patients before their first shipment of the sensitive drug and patients restarting use of the sensitive drug after not receiving the sensitive drug for six months or more. The pharmacist will counsel the patient on the checklist.

In addition to the checklist, the exclusive database includes and maintains patient and prescriber enrollment status, all completed REMS forms, prescription and shipment data, as well as information related to dosing, concomitant medications, and behavior that raises suspicion of misuse, abuse, and/or diversion, including complete RMR histories and alerts regarding potential abuse, misuse, and/or diversion on the patient profiles. The exclusive database also contains database-enabled controls and checks to ensure compliance with the REMS program.

More specifically, the information contained in the exclusive database includes the following:

Prescription date, titration and dosing, and prescriber instructions. Prescriber information, including all current patients who are prescribed the sensitive drug and whether the prescriber's DEA and state license numbers are active.

Patient information, including name and two identifiers, current and previous prescribers, comorbid conditions, concomitant medications and other potentially interacting agents, prescription history, and early refill requests and outcomes.

Certified, central pharmacy interactions with prescribers, patients, caregivers, and other parties regarding the patient, caregiver, prescriber, or prescription, including information that might suggest potential patient, caregiver, and/or prescriber misuse, abuse, and/or diversion.

Data and information on all shipments of the sensitive drug, including number and quantity of shipments sent daily.

Prior to dispensing a newly enrolled patient's first-time fill, a pharmacist at the certified, central pharmacy completes the patient counseling checklist, asking each patient for a list of his or her current medications and doses. The certified, central pharmacy also asks a patient if his or her medications have changed at the time of the scheduling call for subsequent shipments, and a pharmacist must notify the prescriber when the patient is receiving concomitant contraindicated medications.

Upon implementation of the REMS program, patient-reported changes in concomitant medications during any refills and notifications to prescribers are captured through the completion of the REMS program patient counseling checklist. Capture of these medications, with the subsequent confirmation regarding prescriber notification in the checklist, enables accurate reporting of data from both first fills and refills for assessment purposes.

Figure 2:
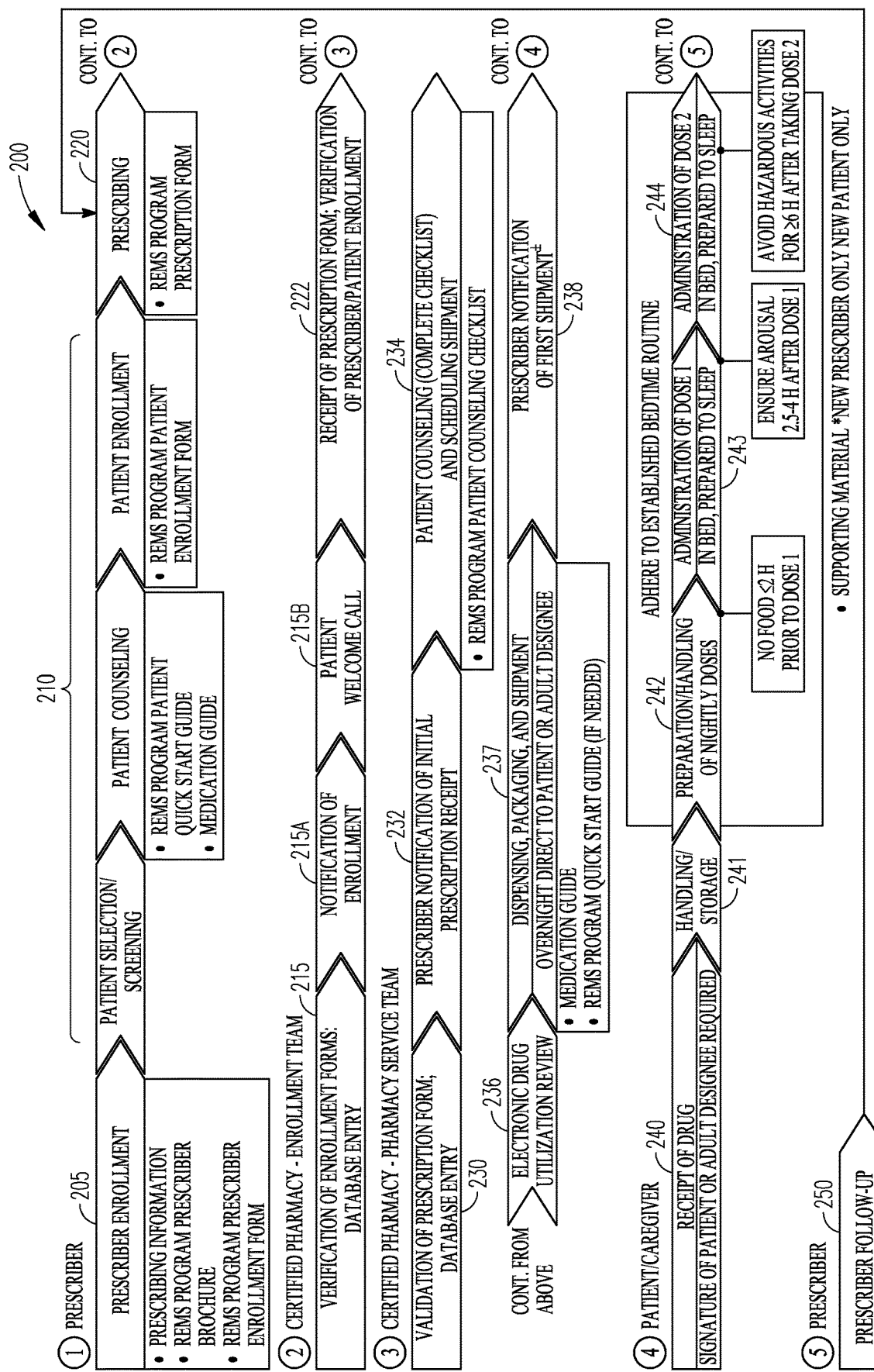
FIG. 2 is a flowchart describing a method for sensitive drug distribution at least partially utilizing a computer system such as that shown in FIG. 1.

An example embodiment of a restricted distribution program for a sensitive drug is illustrated in FIG. 2, and as noted above, can be referred to as a Risk Evaluation and Mitigation Strategy (REMS). The REMS system 200 begins with prescriber and patient enrollment, screening, counseling, and educating. Specifically, as illustrated at 205, a prescriber is enrolled in the REMS program. The prescriber enrollment 205 includes providing prescribing information and a prescribing program brochure to the potential prescriber. After review of the information and brochure, the prescriber can fill out a prescriber enrollment form. This prescriber enrollment form is submitted to a certified, central pharmacy, as will be discussed in more detail in connection with operation 215.

In a similar fashion, as indicated at 210, potential patients, including pediatric patients and caregivers associated with those pediatric patients, are screened, selected, counseled, and enrolled. It is noted that an elderly patient or other special needs patient, like a pediatric patient, can also have a caregiver, although it is not a strict requirement like in the case of a pediatric patient. The screening, selecting, counseling, and enrolling procedures include providing to the patient and caregiver a patient quick start guide, a medication guide, and a patient enrollment form. Additionally, a brochure is provided to the caregiver that is specific to pediatric patients (or elderly or other special needs patients). The patient quick start guide, medication guide, and brochure instruct and educate the patient and caregiver on the proper use, dosing, and handling of the sensitive drug. After review of the patient quick start guide, the medication guide, and the brochure, the patient and/or caregiver can fill out a patient enrollment form. This patient enrollment form is submitted to a certified, central pharmacy, as will be discussed in more detail in connection with operation 215.

As indicated at 215, a certified, central pharmacy includes an enrollment team. The enrollment team verifies the completion of the prescriber and patient enrollment forms, and enters the prescriber, patient, and if present caregiver, information into the exclusive database of the certified, central pharmacy. At 215A, the certified, central pharmacy notifies the prescriber or patient (and if appropriate the caregiver), as the case may be, of the successful enrollment, and as indicated at 215B, a welcome message is transmitted to the patient and/or caregiver such as via a telephone call, an email message, a mailed letter, a text message, or any other form of suitable communication.

After successful enrollment of a prescriber, the enrolled prescriber can prescribe the sensitive drug to one or more enrolled patients. Similarly, after successful enrollment of a patient, the enrolled patient can be prescribed the sensitive drug by an enrolled prescriber. The writing of a prescription for the sensitive drug is done using a REMS program prescription form (220). At 222, the prescriber transmits the prescription form to the certified, central pharmacy. Upon receipt of the prescription form, the certified, central pharmacy verifies the prescriber, patient, and caregiver information on the prescription form with the prescriber, patient, and caregiver information in the certified, central pharmacy's exclusive computer database. As noted previously, the prescriber, patient, and caregiver information in the certified, central pharmacy's exclusive database was extracted from the prescriber and patient enrollment forms.

Operation 230 commences the duties of the certified, central pharmacy's services team. Specifically, at 230, the certified, central pharmacy's services team validates the non-prescriber and non-patient prescription information (that is, the actual prescription information) on the prescription form. After the prescription information is validated, the prescription information is entered into the certified, central pharmacy's exclusive database. As noted elsewhere in this specification, requiring the entry into the certified, central pharmacy's exclusive database of all prescribers prescribing the prescription drug and all patients being prescribed the prescription drug assists in preventing abuse, misuse, and/or diversion of the prescription drug. At 232, the certified, central pharmacy notifies the prescriber that the certified, central pharmacy has received the prescription request from the prescriber.

At 234, the certified, central pharmacy verifies that the patient and any associated caregiver have completed the required counseling, and/or provides additional counseling and responds to any questions or concerns of the patient and/or caregiver. To ease the verification process for the certified, central pharmacy, the certified, central pharmacy can employ a counseling checklist, which can include items such as verifying that the patient or caregiver has read the educational materials, has completed all necessary forms, has completed any tests and/or assessments, and as explained in more detail herein, the patient has an associated caregiver if the patient is a pediatric patient. That is, the check list ensures that the patient is educated and counseled about safe use and handling of the sensitive drug and about the requirements of the REMS program, and documents information about concomitant medication use and comorbidities.

At 236, the certified, central pharmacy uses its computer systems and its exclusive database to conduct an electronic drug utilization review. In an embodiment, the electronic drug utilization review queries the exclusive database to determine what, if any, other pharmaceuticals the patient is presently taking or has taken in the past. For any pharmaceuticals that the patient is taking or has taken, the system checks its database to determine if any of these pharmaceuticals may cause an adverse reaction if taken in conjunction with the sensitive drug. If there is a potential for adverse reaction, the system notifies personnel of the certified, central pharmacy, and the personnel can take the appropriate action.

If the electronic drug utilization review does not identify any other pharmaceuticals that could cause an adverse reaction in connection with the sensitive drug, or any potential adverse reactions with other pharmaceuticals have been adequately addressed by certified, central pharmacy personnel, then the certified, central pharmacy proceeds with the dispensing, packaging, and shipment of the sensitive drug at 237. The dispensing involves placing the correct amount of the sensitive drug into the correct number and size of containers. The packaging of the sensitive drug includes adding the sensitive drug containers into a packaging/shipping box or other container, and adding incidentals such as measuring cups or other apparatus, a copy of the medication guide, and a copy of the patient quick start guide, and a copy of the caregiver brochure that is specific to pediatric and other special needs patients. The entire package is then shipped to the patient and/or the caregiver associated with the patient. In an embodiment, this shipment is via an overnight carrier.

At 238, the prescriber is notified of the shipment of the sensitive drug to the patient. Such notification can occur for only the first shipment of the sensitive drug, or for any shipment of the sensitive drug to the patient. Such notification enables the prescriber to follow the prescription history of the sensitive drug to the patient, and to more easily become aware of any abuse, misuse, and/or diversion of the sensitive drug.

Beginning at 240, operations are described that relate to the reception of the sensitive drug by the patient and/or caregiver, and the administering of the sensitive drug to the patient. Specifically, at 240, the patient and/or caregiver receives the sensitive drug via the delivery service, and signs for the sensitive drug before the delivery service leaves the sensitive drug with the patient and/or the caregiver. Two items are noteworthy here. The sensitive drug is only available through the certified, central pharmacy and its associated exclusive database; it is not available for delivery through a retail pharmacy. Also, the certified, central pharmacy can receive an immediate electronic communication from the delivery service that the sensitive drug has been delivered to and signed/accepted by the patient and/or the caregiver. The certified, central pharmacy can then also inform the prescriber that the sensitive drug has been successfully delivered to the patient. These procedures and sub-procedures contribute to the certified, central pharmacy's ability to prevent abuse, misuse, and/or diversion of the sensitive drug.

At 241, the patient and/or caregiver appropriately stores the sensitive drug. The appropriate storage of the sensitive drug is outlined and explained in the medication guide, the patient quick start guide, and the brochure provided to the caregiver that is specific to pediatric and other special needs patients. Storage requirements can involve such matters as the proper environment for the sensitive drug (light, temperature, humidity, etc.) and prevention of access of the drug by other persons (for example, storing the sensitive drug in a locked cabinet).

At 242, the patient and/or caregiver prepares a dosage of the sensitive drug. In a simple situation, this may only involve removing a pill, tablet, or capsule from its container, and taking or administering the sensitive drug to the patient with the proper type and amount of fluids and food. In a more complex situation, there may be multiple doses within a particular time period, wherein that time period may be during nighttime hours, and the sensitive drug may be in a liquid form that requires a measuring of the proper amount of the sensitive drug.

More specifically, as illustrated at operations 243 and 244, there is an administering of the sensitive drug in a first dosage and a second dosage. For example, as could be explained in the medication guide, the patient quick start guide, or the caregiver brochure, no food should be consumed during a certain time period prior to administering the sensitive drug. For example, no food should be consumed two hours (or less) before the sensitive drug is taken. If the sensitive drug relates to the treatment of sleep disorders, it may be required that the sensitive drug is only taken in bed, just prior to laying down in bed to sleep for the night. Additionally, if the second dose is to be taken before the patient wakes in the morning, the patient should set an alarm so that the patient can wake up and take the second dose of the sensitive drug. The second dose should be at the patient's bedside, so that the patient can take the second dose in bed, and immediately lay down again and return to sleep for the night. There may be additional provisos such as not operating any vehicles or machinery for a certain time period after any dose. The proper dosage regime of operations 243 and 244 are once again outlined and explained in the medication guide, the patient quick start guide, and/or the caregiver brochure.

At 250, the prescriber follows up with the patient (or associated caregiver) to verify that the patient is taking the sensitive drug in the appropriate manner, and to determine if there are any other issues with the patient and/or caregiver that need to be addressed. In addition to the prescriber follow-up, the certified, central pharmacy may also follow up with the patient and/or caregiver to determine that the sensitive drug is being properly administered and that there are no issues with the patient and/or caregiver.

Figure 3:
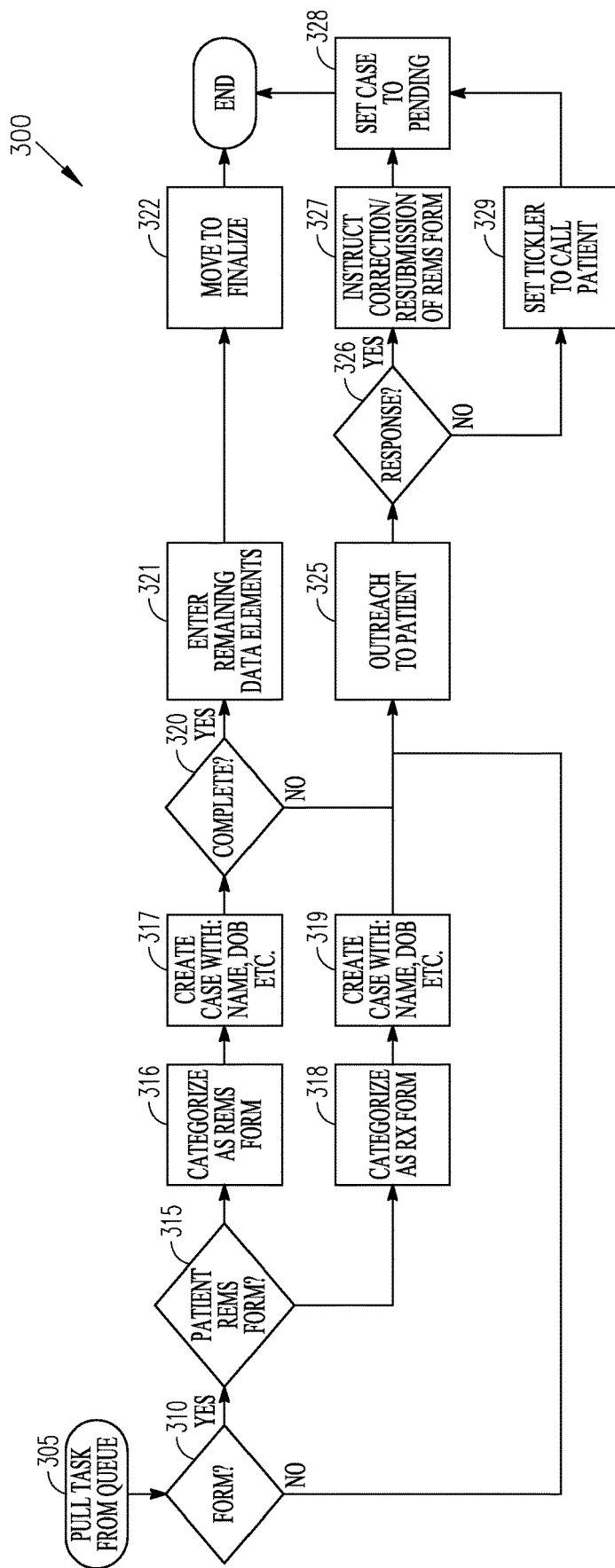
FIG. 3 is a flowchart describing a method for sensitive drug distribution at least partially utilizing a computer system such as that shown in FIG. 1.

Another embodiment of a REMS restricted distribution program 300 for a sensitive drug is illustrated in FIG. 3. At 305, a task is pulled from a queue. This task queue represents actions that have to be taken by the certified, central pharmacy in relation to distributing the sensitive drug, from enrollment to shipping to follow-up.

At decision block 310, the computer system of the certified, central pharmacy determines if the task in the queue relates to some type of form. If the task does not relate to a form, the system moves on to an outreach to the patient (and/or associated caregiver) as noted in operation 325, which is discussed in detail below. If the task does relate to a form, then at 315, the certified, central pharmacy determines if the form is a REMS form (that is, an enrollment form). If the task is a REMS form, then the form is formally categorized as a REMS form at 316, and at 317, a case is created for the patient that includes all the information needed to enroll the patient in the REMS system such as name, date of birth, gender, height, weight, etc.

If the certified, central pharmacy determines at operation 315 that the task is not a REMS form, then the certified, central pharmacy categorizes the form as a prescription form at 318. That is, the form at 318 is from a prescriber who is prescribing a sensitive drug to a patient. Then at 319, a case is created for this particular drug for this particular patient for this particular prescription.

At decision block 320, the certified, central pharmacy determines whether the creation of the REMS case at operation 317 has been completed. If the creation of the REMS case has not been completed, the remaining data are entered at operation 321. Such remaining data can include any data relating to the new patient enrollee (and/or associated caregiver) that was not previously available, such as marital status. After entering the remaining data at operation 321, a final review of the completed REMS form is performed at 322.

At operation 325, a patient (and/or caregiver) outreach is performed. This outreach occurs both after the certified, central pharmacy determines at 320 that the REMS form has not been completed, and after the certified, central pharmacy creates at 319 a prescription form that was written by a particular prescriber for a particular sensitive drug for a particular patient. For the uncompleted REMS form, the patient outreach may be to determine the information that is missing from the REMS form. For the prescription form, the outreach may be able to determine if the patient has begun taking any other prescription drugs, since the patient's enrollment in the REMS program, wherein such other prescription drugs could possibly negatively affect the patient if the patient begins taking the new sensitive drug.

At decision block 326, the certified, central pharmacy determines whether there was a response from the patient to the outreach to the patient at 325. If there was a patient response, then at 327 the REMS form is first corrected and/or updated, and at 328, the patient's case is set to pending. That is, it is waiting for a prescription to be received at the certified, central pharmacy or it is waiting for the certified, central pharmacy to act on distributing a pending prescription. If a response was not received from the patient at 326, then at 329, the certified, central pharmacy dockets a note to follow up with a call to the patient.

The central database described above is a relational database running on the system of FIG. 1, or a server-based system having a similar architecture coupled to workstations via a network, as represented by communications 160. The database is likely stored in storage 140, and contains multiple fields of information as indicated at 400 in FIG. 4. The organization and groupings of the fields are shown in one format for convenience. It is recognized that many different organizations or schemas may be utilized. In one embodiment, the groups of fields comprise prescriber fields 410, patient fields 420, prescription fields 430, caregiver fields 435, and insurance fields 440. For purposes of illustration, all the entries described with respect to the above processes are included in the fields. In further embodiments, no such groupings are made, and the data are organized in a different manner.

Figure 5:
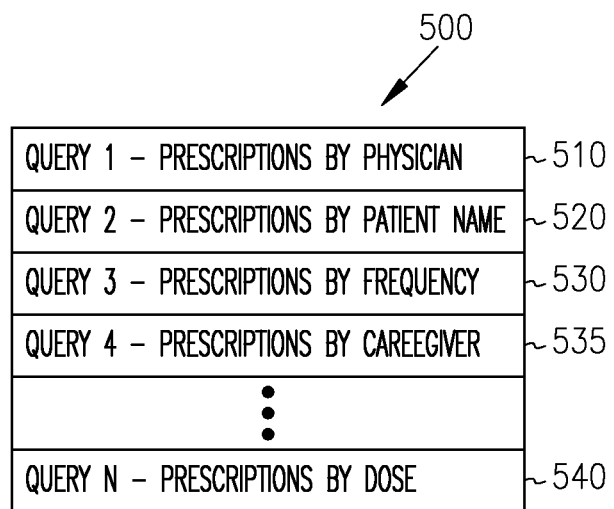
FIG. 5 is a block diagram showing a list of queries against the database fields.

Several queries are illustrated at 500 in FIG. 5. There may be many other queries as required by individual state reporting requirements. A first query at 510 is used to identify prescriptions written by physician. The queries may be written in structured query language, natural query languages or in any other manner compatible with the database. A second query 520 is used to pull information from the database related to prescriptions by patient name. A third query 530 is used to determine prescriptions by frequency. A fourth query 535 is used to determine prescriptions by caregiver, and an $n^{th}$ query finds prescriptions by dose at 540. Using query languages combined with the depth of data in the central database allows many other methods of investigating for potential abuse of the drugs. The central database ensures that all prescriptions, prescribers, patients, and caregivers are tracked and subject to such investigations. In further embodiments, the central database may be distributed among multiple computers provided a query operates over all data relating to such prescriptions, prescribers, patients, and caregivers for the drug.

An example of one prescription and enrollment form is shown at 600 in FIG. 6. As previously indicated, several fields are included for prescriber information, prescription information, patient information, and caregiver information.

Figure 7:
FIG. 7 is a copy of one example of a NORD application request form for patient financial assistance.
Figure 11A:
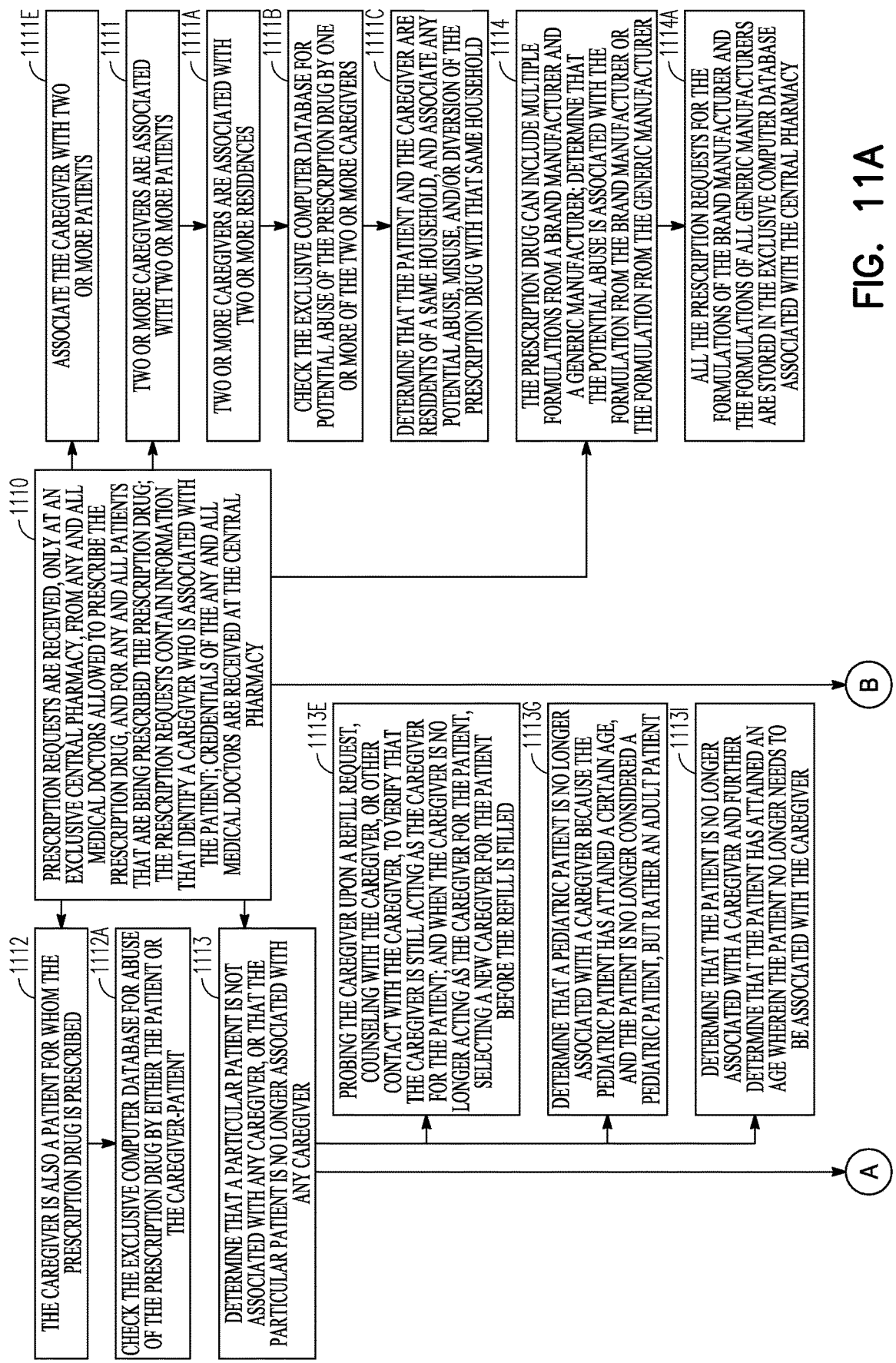
FIGS. 11A, 11B, 11C, and 11D are a flowchart describing a method for sensitive drug distribution to a pediatric patient population at least partially utilizing a computer system such as that shown in FIG. 1.
Figure 11B:
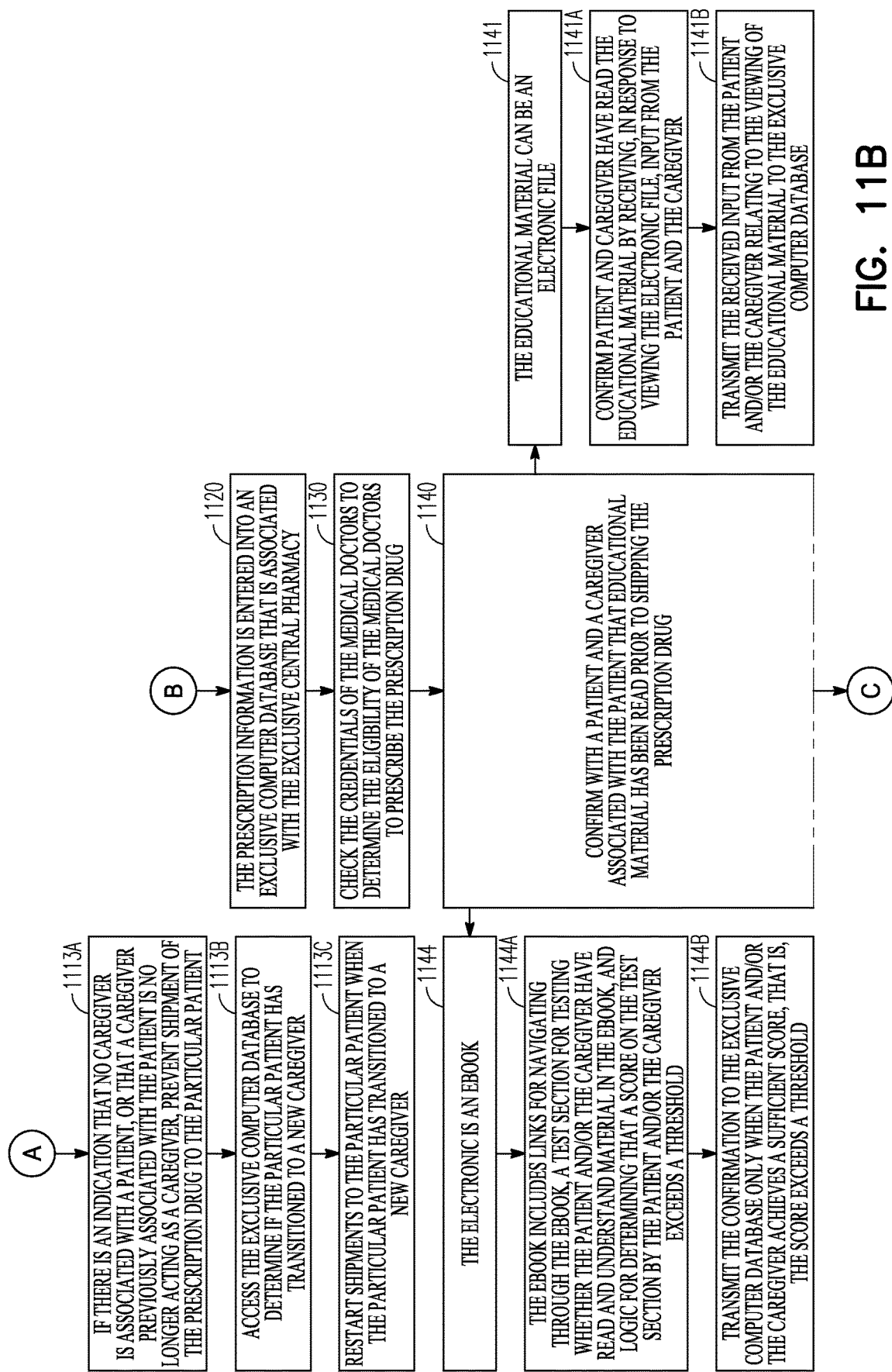
Figure 11C:
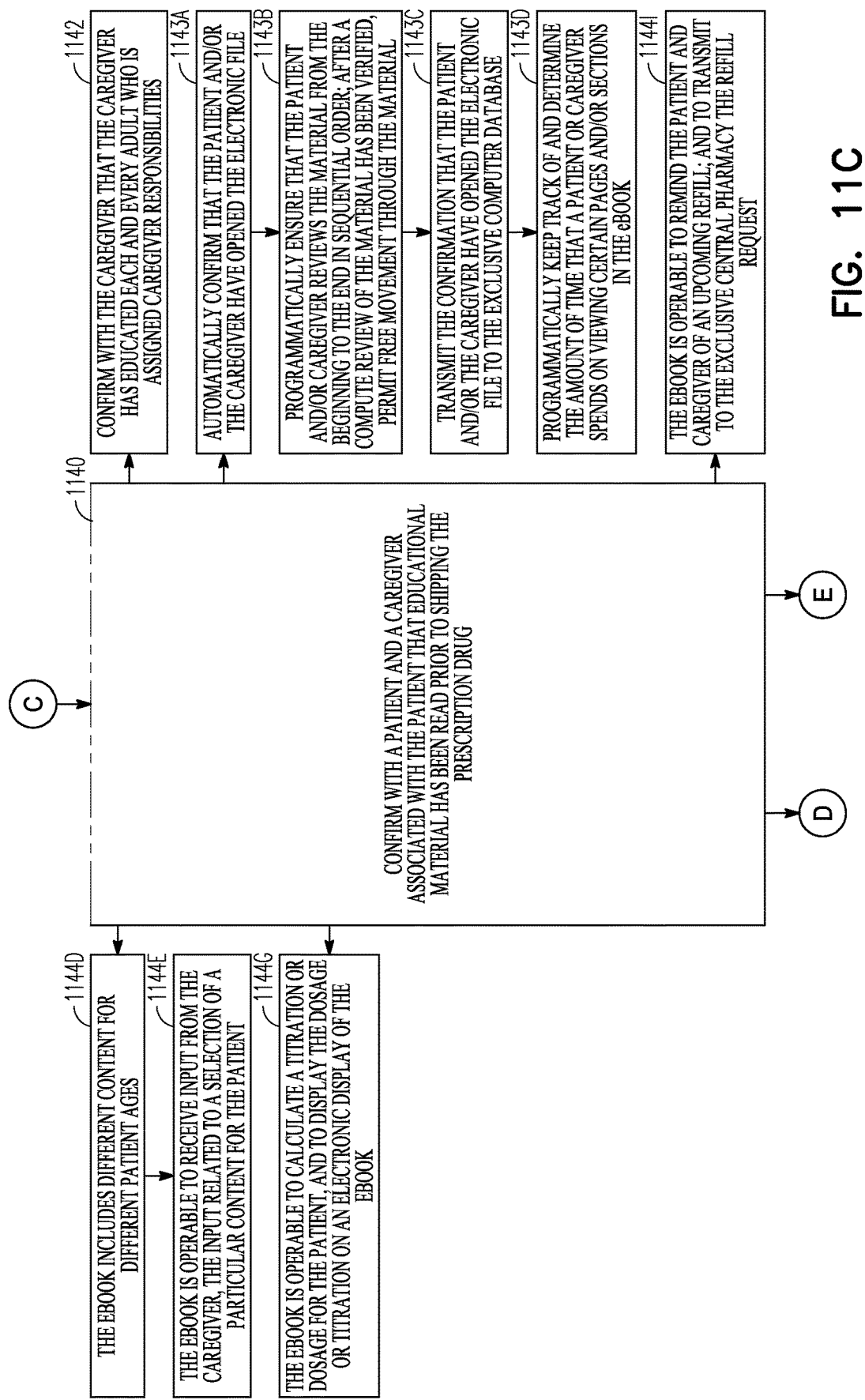
Figure 11D:
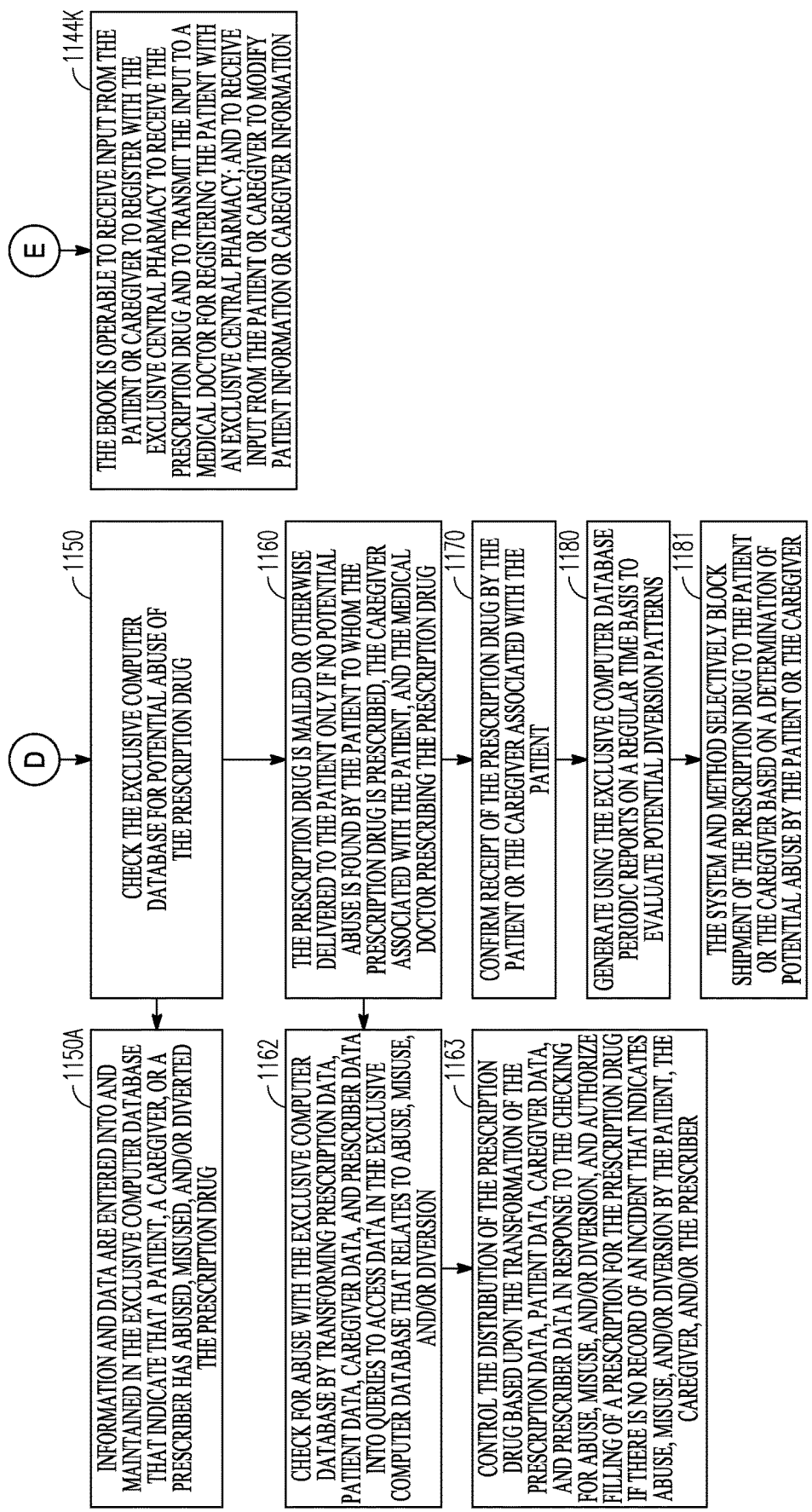

FIG. 7 is a copy of one example NORD application request form 700 used to request that an application be sent to a patient and/or caregiver for financial assistance.

FIG. 8 is a copy of one example application 800 for financial assistance as requested by form 800. The form requires patient, caregiver, and physician information. Social security number information is also requested. The form provides information for approving the financial assistance and for tracking assistance provided.

FIG. 9 is a copy of one example voucher request for medication for use with the NORD application request form of FIG. 7. In addition to patient, caregiver, and physician information, prescription information and diagnosis information is also provided.

Figure 4:
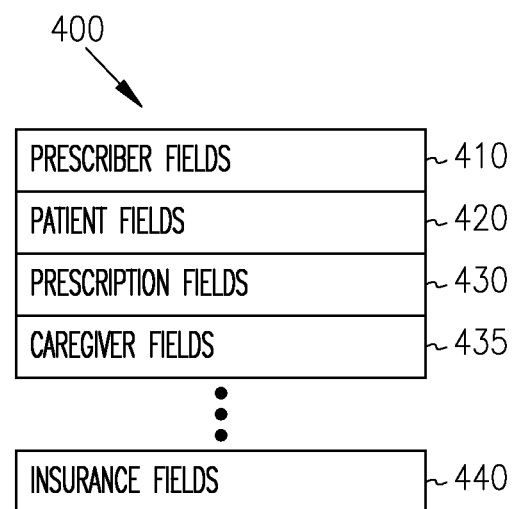
FIG. 4 is a block diagram of database fields.

FIGS. 10A, 10B and 10C are descriptions of sample reports obtained by querying a central database having fields represented in FIG. 4. The activities grouped by sales, regulatory, quality assurance, call center, pharmacy, inventory, reimbursement, patient care and drug information. Each report has an associated frequency or frequencies. The reports are obtained by running queries against the database, with the queries written in one of many query languages.

While an embodiment of the invention has been described with respect to a Schedule III drug, it is useful for other sensitive drugs that are DEA or Federally scheduled drugs in Schedule II-V, as well as still other sensitive drugs where multiple controls are desired for distribution and use.

Another embodiment is directed to a controlled distribution of a prescription drug to a pediatric patient base (or elderly or other special needs patient base), and in particular a prescription drug that is susceptible to abuse, misuse, and/or diversion. Similar to previously-described embodiments, these other embodiments utilize one or more of a central pharmacy and an exclusive computer database. Additionally, similar to previously-disclosed embodiments, these other embodiments maintain data on prescriptions, prescribers, and patients, and track these data to identify potential abuse, misuse, and/or diversion. As noted above, these previously-disclosed embodiments have become to be referred to as Risk Evaluation and Mitigation Strategies (REMS). The new other embodiments add several features, including associating a pediatric, elderly, or other special needs patient with a responsible caregiver, maintaining data on caregivers, and analyzing the data to identify potential abuse, misuse, and/or diversion of the prescription drug by the pediatric patients and/or caregivers. An eBook is also part of these additional REMS system embodiments, which makes it easier for patients and caregivers to review the educational material on the prescription drug, allows for automatic verification that the patient and/or caregiver have reviewed the material, and permits testing of the patient and/or caregiver to verify that the patient and/or caregiver have reviewed and understand the material. In yet another embodiment, the eBook can include a survey that is administered to the patient and/or caregiver. This survey can be used to determine, among other things, the effectiveness of the eBook and the contents thereof.

FIGS. 11A, 11B, 11C, 11D, 12A, and 12B are block diagrams illustrating features and operations of a system and method of distributing a prescription drug under exclusive control of an exclusive central pharmacy, and in particular, distributing a prescription drug to a pediatric patient (or elderly or other special needs patient) who is associated with a caregiver, and monitoring the patient, the prescriber, and the caregiver to identify potential abuse, misuse, and/or diversion of the prescription drug. FIGS. 11A, 11B, 11C, 11D, 12A, and 12B include a number of process blocks 1102-1181 and 1210-1243. Though arranged somewhat serially in the examples of FIGS. 11A, 11B, 11C, 11D, 12A, and 12B, other examples may reorder the blocks, omit one or more blocks, and/or execute two or more blocks in parallel using multiple processors or a single processor organized as two or more virtual machines or sub-processors. Moreover, still other examples can implement the blocks as one or more specific interconnected hardware or integrated circuit modules with related control and data signals communicated between and through the modules. Thus, any process flow is applicable to software, firmware, hardware, and hybrid implementations.

Referring now specifically to FIGS. 11A, 11B, 11C, and 11D, at 1110, prescription requests are received into a computer processor. The prescription requests are received from any and all medical doctors allowed to prescribe the prescription drug. The prescription requests are received for any and all patients that are being prescribed the prescription drug. All of these prescription requests are received only at an exclusive central pharmacy (also referred to as a certified, central pharmacy). In an embodiment, an exclusive central pharmacy is a pharmacy that is the only pharmacy that is permitted to process prescriptions for the prescription drug. By requiring that all of the prescription requests are received only at the exclusive central pharmacy, the system and method establish a high degree of control over the distribution of the prescription drug, and the system and method can more easily identify potential abuse, misuse, and/or diversion of the prescription drug, which will be explained in more detail in the following paragraphs. The prescription requests contain information that identify not only the patients, the prescribers, and the prescription drug, but also a caregiver who is associated with the patient, and in particular, a pediatric patient. Credentials of the any and all medical doctors are also entered into the computer processor.

As disclosed in operation 1120, the system and method require that the information is entered into an exclusive computer database that is associated with the exclusive central pharmacy. The exclusive central pharmacy can then use the exclusive computer database to analyze the prescription, patient, caregiver, and medical doctor data to identify potential abuse, misuse, and/or diversion situations. The requirement that all prescriptions for the prescription drug are processed only by the exclusive central pharmacy using only the exclusive computer database makes the system's ability to identify potential abuse, misuse, and/or diversions more robust by accessing the protected data in the exclusive computer database that has been collected over a period of time and using that data for proactively monitoring patient safety.

At 1130, the computer processor checks the credentials of the any and all medical doctors to determine the eligibility of the medical doctors to prescribe the prescription drug. At 1140, the method provides for confirming with a patient and a caregiver associated with the patient that educational material has been read prior to shipping the prescription drug. It can be important that both the patient and caregiver have read the educational material (notwithstanding that, as disclosed below, the caregiver may not be viewed as a stakeholder), since both are intimately involved with the treatment of the patient, and both must therefore understand the proper handling of the prescription drug.

At 1150, the computer processor checks/queries the exclusive computer database for potential abuse, misuse, and/or diversion of the prescription drug. For example, the computer processor can check to see if a patient or caregiver is requesting too many early refills, and/or if a medical doctor is prescribing an inordinate number of prescriptions to an inordinate number of patients. At 1150A, information and data are entered into and maintained in the exclusive computer database that indicate that a patient, a caregiver, and/or a prescriber has abused, misused, and/or diverted the prescription drug. This information can be gleaned from checking the database via queries, as just discussed in connection with operation 1150. Alternatively, this information can be directly entered by an official of the central pharmacy after identifying a potential abuse, misuse, and/or diversion of the prescription drug via some means other than a database query. At 1160, the prescription drug is mailed or otherwise delivered to the patient only if no potential abuse, misuse, and/or diversion is found by the patient to whom the prescription drug is prescribed, the caregiver associated with the patient, and the medical doctor prescribing the prescription drug. As noted throughout this specification, potential abuse, misuse, and/or diversion by the patient could be identified by a patient requesting early refills or claiming that prescriptions have been stolen, lost, or spilled. Potential abuse, misuse, and/or diversion by the caregiver could be identified in a similar manner. Potential abuse, misuse, and/or diversion by the medical doctor could be identified, for example, if the medical doctor writes prescriptions for early refills for several patients.

In another embodiment, as outlined at 1162, the system and method check for abuse, misuse, and/or diversion with the exclusive computer database by transforming prescription data, patient data, caregiver data, and prescriber data into one or more queries to access data in the exclusive computer database that relates to abuse, misuse, and/or diversion. The results of the queries can indicate whether abuse, misuse, and/or diversion has potentially occurred and should be investigated. In another embodiment, as indicated at 1163, the system and method control the distribution of the prescription drug based upon the transformation of the prescription data, patient data, caregiver data, and prescriber data in response to the checking for abuse, misuse, and/or diversion, and authorize filling of a prescription for the prescription drug if there is no record of an incident that indicates abuse, misuse, and/or diversion by the patient, the caregiver, and/or the prescriber. If there is a record of such incident, the exclusive computer database indicates that such incident has been investigated, and the exclusive computer database indicates that such incident does not involve abuse, misuse, and/or diversion.

At 1170, the system and method confirm receipt of the prescription drug by the patient or the caregiver associated with the patient. Such confirmation can be accomplished by having the patient and/or caregiver electronically sign using a mobile device of the delivery service, and receiving at the computer processor of the exclusive central pharmacy confirmation directly from the mobile device of the delivery service (or an intermediate server of the delivery service or other party).

At 1180, the system and method generate with the computer processor and the exclusive computer database periodic reports on a regular time basis to evaluate potential diversion patterns. A regular time basis has equally spaced time intervals between reports, and such reports are not generated in response to a specific report or incident of abuse, misuse, and/or diversion. A potential diversion pattern could be identifying that a caregiver has claimed that there have been three spillage incidents of the prescription drug within the last three months. Those of skill in the art will realize that other patterns could be identified. At 1181, the system and method selectively block shipment of the prescription drug to the patient or the caregiver based on a determination of potential abuse, misuse, and/or diversion by the patient or the caregiver.

At 1141, it is noted that the educational material can be an electronic file. When the educational material is an electronic file, the process of confirming that the patient and the caregiver have read the educational material can include receiving, in response to viewing the electronic file by the patient and the caregiver, input from the patient and the caregiver (1141A). This input can be, in an embodiment, a simple clicking on a button indicating that the patient and/or caregiver have read/reviewed the educational material. At 1141B, the system and method transmit, to the exclusive computer database, the received input from the patient and/or the caregiver relating to the viewing of the educational material. As indicated at 1142, the system and method confirm with the caregiver that the caregiver has educated each and every adult who is assigned caregiver responsibilities. Ensuring that all persons with caregiver responsibilities are properly educated further decreases the likelihood that the prescription drug with be abused, misused, and/or diverted.

In another embodiment wherein the educational material is an electronic file, the system and method at 1143A automatically confirm that the patient and/or the caregiver has opened the electronic file. This embodiment does not rely on the veracity of the input of the patient and/or caregiver, thereby mitigating another possible source of abuse, misuse, and/or diversion. In another embodiment, as indicated at 1143B, the system and method programmatically ensure that the patient and/or caregiver reviews the material from the beginning to the end in sequential order. After a complete review of the file, the system and method permit free movement through the file. Thereafter, at 1143C, the system and method transmit to the exclusive computer database the confirmation that the patient and/or the caregiver have opened the electronic file. In yet another embodiment, the system and method can determine whether the patient or caregiver has clicked on a link in the electronic file. The system and method can further programmatically keep track of and determine the amount of time that a patient or caregiver spends on viewing certain pages and/or sections in the electronic file (1143D).

As noted at 1144, the electronic file can be an eBook. The eBook can include links for navigating through the eBook, a test section for testing whether the patient and/or the caregiver have read and understand material in the eBook, and logic for determining that a score on the test section by the patient and/or the caregiver exceeds a threshold (1144A). This embodiment is an advance on a simple confirmation that the patient and/or caregiver have simply opened the electronic file or eBook. Specifically, the eBook will have to be read by the patient and/or caregiver in order to achieve a sufficient score on the test. At 1144B, the system and method transmit the confirmation to the exclusive computer database only when the patient and/or the caregiver achieves a sufficient score, that is, the score exceeds a threshold.

Further aspects and features of the eBook are as follows. The eBook can include different content for different ages of pediatric patients. That is, the content would likely be different if directed to a seven year old patient versus a seventeen year old patient (1144D). In a related embodiment, the eBook is operable to receive input from the caregiver, such that the caregiver can select the particular age-appropriate version of the eBook suitable to the pediatric patient associated with the caregiver (1144E).

Additionally, as noted at 1144G, the eBook is capable of calculating a titration or dosage for the patient. The patient and/or caregiver would provide certain information such as age of the patient, gender of the patient, and weight of the patient, and the eBook processor will calculate the appropriate dosage and/or titration. The calculated dosage and/or titration can then be displayed on the display unit of the eBook.

The eBook is also operable to remind the patient and/or caregiver of an upcoming refill. After the reminder is conveyed to the patient and/or caregiver, the eBook can receive input from the patient and/or caregiver indicating a desire for the refill, and the eBook can transmit the refill request to the exclusive central pharmacy (1144I).

As indicated at 1144K, the eBook is operable to receive input from the patient or the caregiver associated with the patient to register in a distribution program associated with the exclusive central pharmacy to receive the prescription drug and to transmit the input to a medical doctor for registering the patient with the exclusive central pharmacy. The eBook can then also receive input from the patient or caregiver to receive the initial prescription request from the patient or caregiver. Further, the eBook can receive input from the patient or caregiver to modify the patient information or caregiver information. The patient or caregiver can also receive via the eBook a message from the prescriber and/or the exclusive central pharmacy. In an embodiment, the eBook can include security features such as fingerprint recognition, retinal recognition, face recognition, and/or voice recognition to control access to the contents of the eBook.

Figure 13:
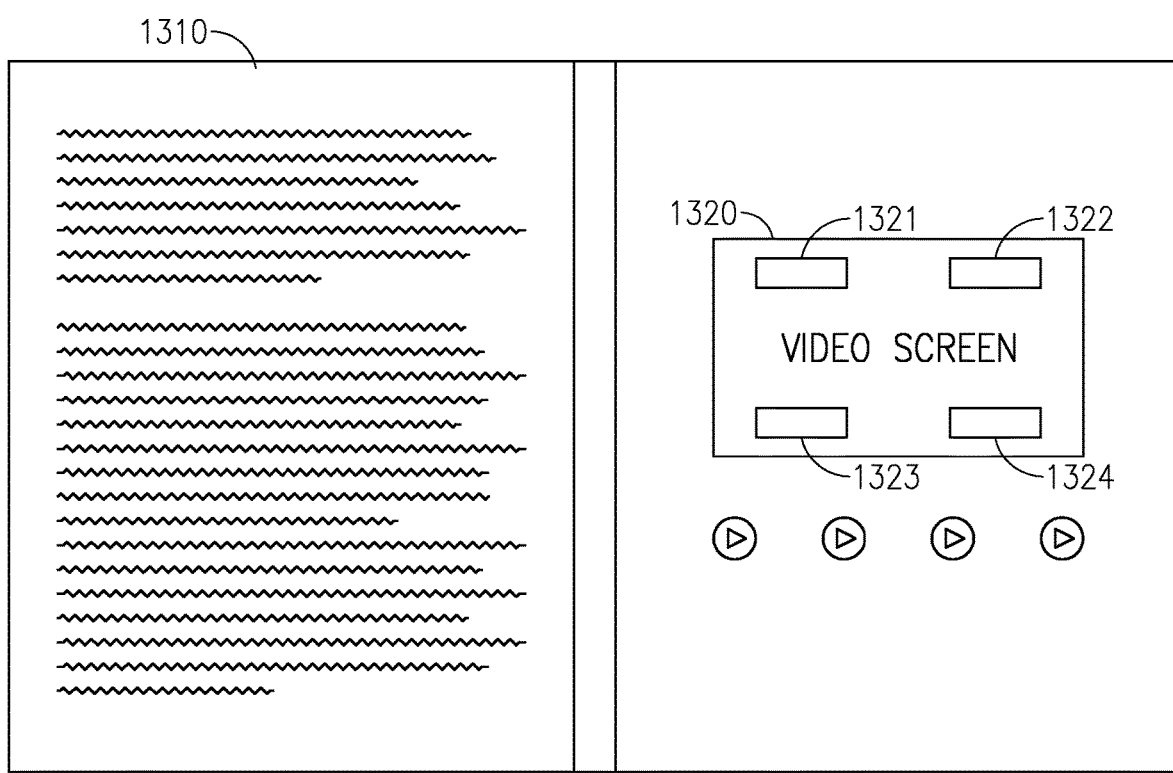
FIG. 13 is an example embodiment of an eBook.

The eBook can be entirely electronic in nature, or it can be a physical publication that includes an electronic component. For example, as illustrated in FIG. 13, a physical material brochure or book 1310 includes an electronic display 1320 that is coupled to a computer processor (not pictured in FIG. 13) that is embedded in or attached to the eBook in some manner. Any input received from the user via a hard button, a soft button, or other input from a touch sensitive electronic display on the eBook can be wirelessly transmitted to the central pharmacy. In an embodiment, the eBook contains an educational display region 1321, a testing display region 1322, an educational display region for pediatric-patient level educational information 1323, and a testing display region for a pediatric-patient test section 1324.

As indicated at 1111, the system and method can accommodate a situation wherein two or more caregivers are associated with a patient and/or two or more patients. Such an association can include virtually any familial relationship, such as two parents and three children; a parent, a grandparent, and a child; and a parent, an older sibling of the patients, and two child-patients, just to provide a few examples. The system and method also permit the two or more caregivers to be associated with two or more residences (1111A). This two-residence feature permits the system and method to more easily identify abuse, misuse, and/or diversion when the caregiver parents of the pediatric patient are separated or divorced. In any such situation, the system and method check the exclusive computer database for potential abuse of the prescription drug by one or more of the two or more caregivers (1111B). In an embodiment, the exclusive computer database is structured such that if only one of the caregivers is suspected of being the source of an abuse, misuse, and/or diversion of the prescription drug, at least because of the system's ability to maintain separate residences of the two caregivers, the system can identify the particular caregiver who is suspected of the abuse, misuse, and/or diversion. Likewise, at 1111C, the system and method can determine that the patient and the caregiver are residents of a same household, and the system and method can associate any potential abuse, misuse, and/or diversion of the prescription drug with that same household. More specifically, the system can track usage wherein there are multiple patients and/or caregivers who are patients in the same household. For example, if a mother is a caregiver and/or a patient, and two of the mother's children are also patients, then the system can monitor all of the mother and the two children as part of the same household. This functionality of the system addresses a scenario wherein the mother requests early refill for herself and for her two dependent children. Even though the mother and two children will all have separate patient identifiers, the system can interrelate the prescription requests of the mother and two children because the system knows that all three are within the same household. This triangular or higher order ability further permits the system to identify abuse, misuse, and/or diversion of the prescription drug. In another embodiment, as indicated at 1111E, the system and method associate the caregiver with two or more patients. In such an embodiment, the system and method check the exclusive computer database for potential abuse of the prescription drug by the caregiver or the two or more patients in much the same manner as when there are multiple patients associated with a caregiver as just described.

The system and method can also handle the situation wherein the caregiver is also a patient for whom the prescription drug is prescribed (1112). This can be accomplished by storing the caregiver's name in both the patient and caregiver's fields in the exclusive computer database, setting a flag associated with the caregiver field, and/or some other data structure technique known to those of skill in the art. Additionally, both patients and caregivers are associated with a unique identification (ID) in the system, and the patient and caregiver can be linked via these IDs. These IDs can further be used to monitor the patients and caregivers over an extended period of time, which contributes to the effectiveness of identifying abuse, misuse, and/or diversion. Whatever the implementation of the situation wherein the caregiver is also a patient, the system and method check the exclusive computer database for abuse of the prescription drug by either the patient or the caregiver-patient (1112A). The exclusive computer database can be further structured to permit the determination of whether a person is acting as a patient or a caregiver. For example, when the person signs for receipt of the prescription drug for the pediatric patient (or elderly or other special needs patient), it can be noted that the person for this transaction is acting as the caregiver. Thereafter, if the caregiver requests an early refill for the patient (and not for the caregiver as a caregiver-patient), then it can be determined that the person could be the source of an abuse, misuse, and/or diversion of the prescription drug as the caregiver.

The system and method can further determine that a particular patient is not associated with any caregiver, or that the particular patient is no longer associated with any caregiver (1113). Such a determination can be accomplished by checking that the caregiver field associated with a particular patient has data in it, and that the data are verified to the extent possible. For example, the system and method can check other sources to verify the data associated with the caregiver, such as the age of the caregiver. In an embodiment, the system and method can periodically check with the caregiver, for example via an email or text message that the caregiver is still serving in a caregiving capacity for the associated patient. At 1113A, if there is an indication that no caregiver is associated with a patient, or that a caregiver previously associated with the patient is no longer acting as a caregiver, the system and method prevent shipment of the prescription drug to the particular patient. Sometime thereafter, the system and method can access the exclusive database again to determine if the pediatric patient has transitioned to a new caregiver (1113B), so that shipments can be re-started (1113C). In another embodiment, as indicated at 1113E, the system and method can probe the caregiver upon a refill request, counseling with the caregiver, or other contact with the caregiver. This probing can be used to verify that the caregiver is still acting as the caregiver for the patient; and when the caregiver is no longer acting as the caregiver for the patient, selecting a new caregiver for the patient before the refill is filled. In an embodiment, the selection of a new caregiver for a patient involves acquiring information about the new caregiver, inputting the information into the system, and then associating the patient with the new caregiver.

In another embodiment, as indicated at 1113G, the system and method determine that a pediatric patient is no longer associated with a caregiver because the pediatric patient has attained a certain age (e.g., 18 years of age), and that patient is then no longer considered a pediatric patient, but rather an adult patient. Such a new adult patient may not need a caregiver. The transition from a pediatric patient with a caregiver to an adult patient with no caregiver can be facilitated by both the eBook and patient activity (e.g., submission of a form) at the pharmacy. This allows for the system to proceed without requiring the (former) caregiver to go into the prescriber's office. The transition from a pediatric patient to an adult patient can be driven by the patient, the caregiver, and/or the prescriber, at least after the patient turns 18 years of age. So once the patient turns 18 year of age, one of the patient, caregiver, and/or prescriber can request the initiation of this transition process, and the system can ensure that the appropriate attestation is obtained from the patient that they are assuming responsibility for their own care, and they will be treated as an adult from that point on. In another embodiment, an emancipated minor (less than 18 years of age) would follow an analogous process, except that they would not have to be 18 years of age or older.

In another embodiment, as indicated at 1113I, the system and method determine, by checking the exclusive computer database, that the patient is no longer associated with a caregiver. In this instance, as contrasted with 1113A wherein shipment is blocked because the patient still requires a caregiver, the system and method determine that the patient has attained an age wherein the patient no longer needs to be associated with the caregiver, for example, the age of 18 years or older.

As noted at 1114, the prescription drug can include multiple formulations from a brand manufacturer and a generic manufacturer. In such a situation, the system and method can determine that the potential abuse is associated with the formulation from the brand manufacturer or the formulation from the generic manufacturer. The ability to make this distinction can assist in identifying whether a particular formulation is susceptible to abuse, misuse, and/or diversion. The ability to make this determination and/or distinction is made possible by the system and method requiring that all the prescription requests for the formulations of the brand manufacturer and the formulations of all generic manufacturers are stored in the exclusive computer database associated with the central pharmacy (1114A).

Figure 12A:
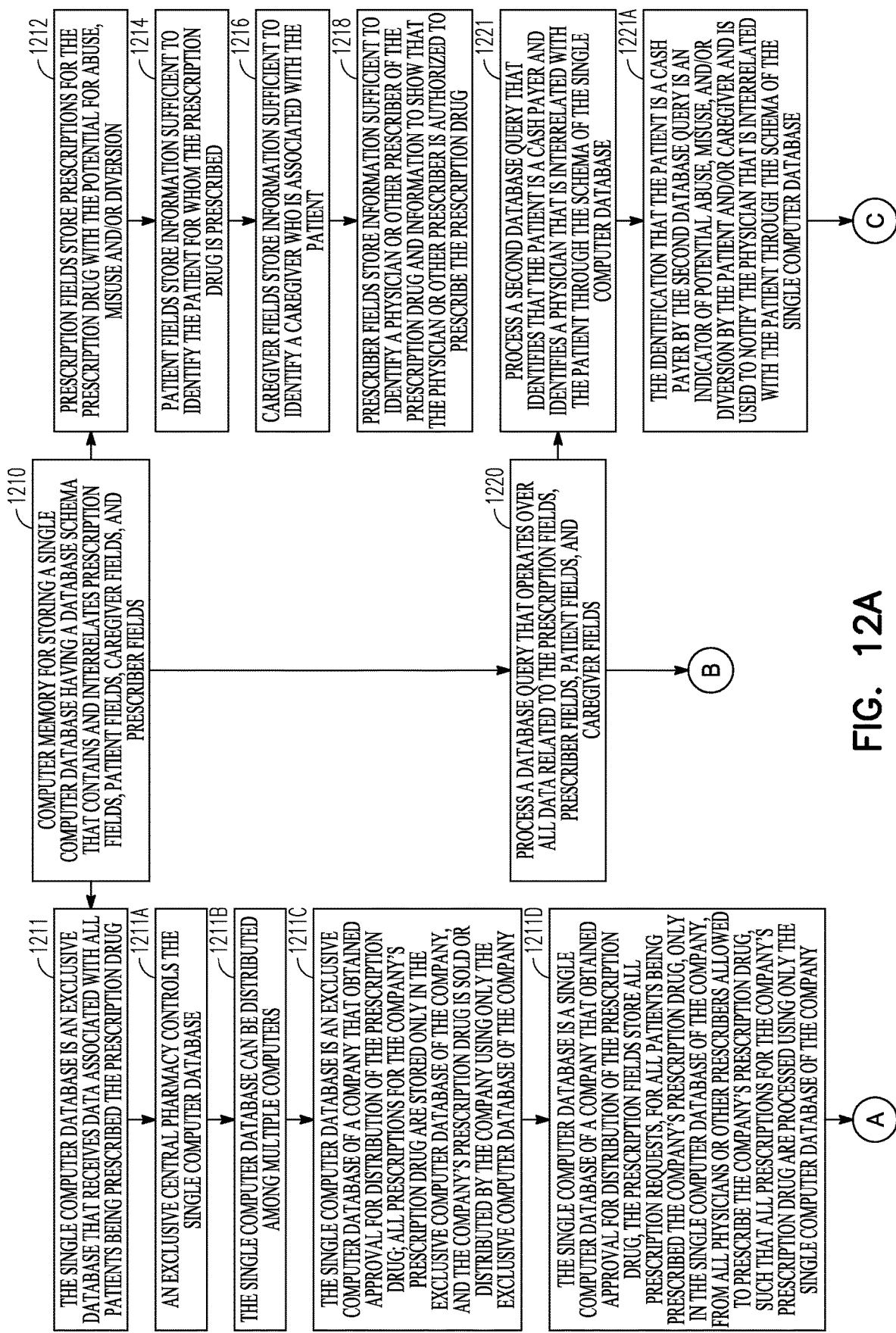
FIGS. 12A and 12B are a flowchart describing a method for sensitive drug distribution to a pediatric population at least partially utilizing a computer system such as that shown in FIG. 1.
Figure 12B:
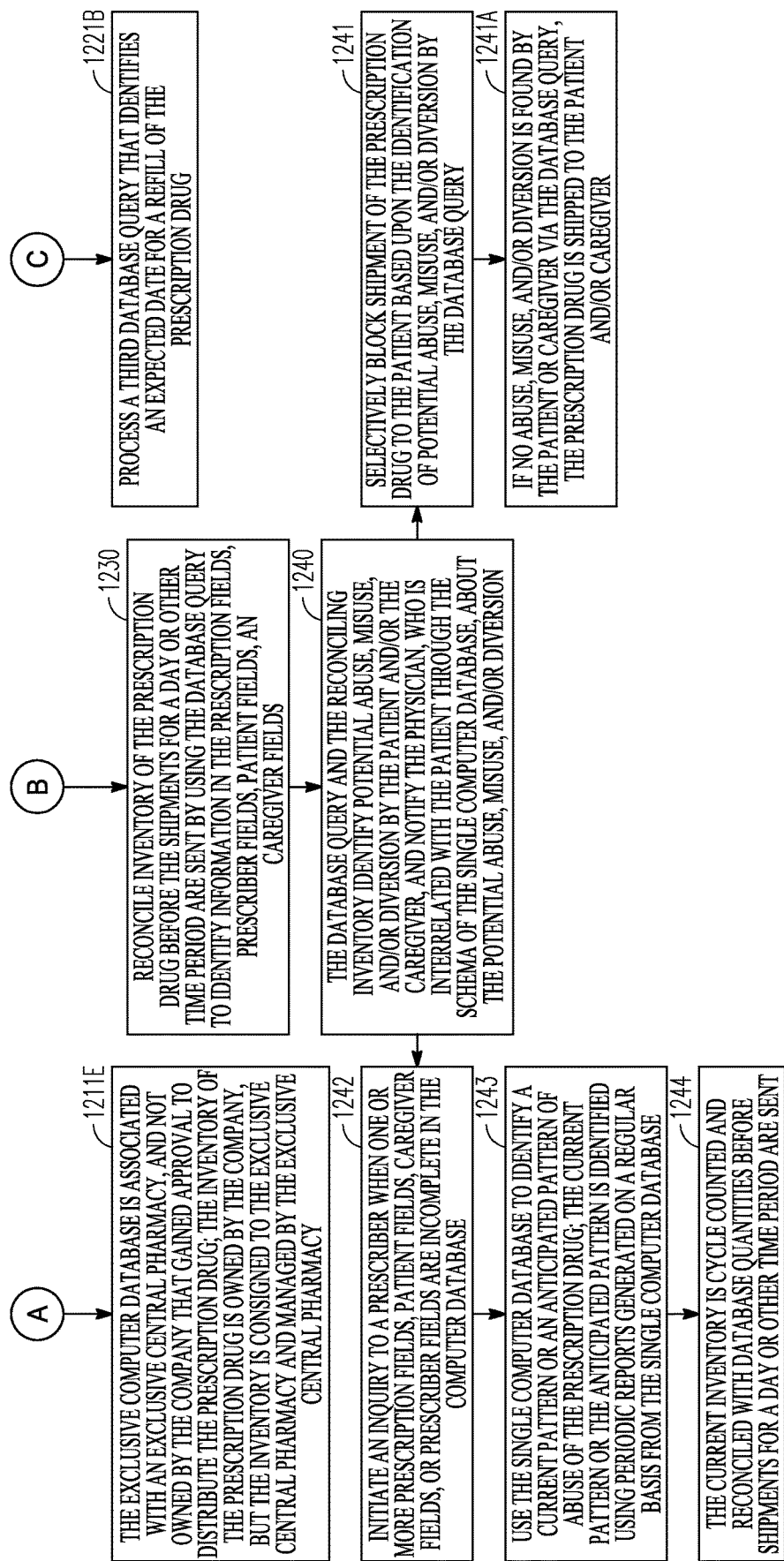

FIGS. 12A and 12B are a block diagram illustrating another embodiment of a system and method for distribution of a prescription drug that has a potential for abuse, misuse, and/or diversion, and in particular, distribution of the prescription drug to a pediatric patient (or elderly or other special needs patient) population. The embodiments of FIGS. 12A and 12B include one or more computer memories for storing a single computer database having a database schema that contains and interrelates prescription fields, patient fields, caregiver fields, and prescriber fields (1210). The prescription fields 1212 are contained within the database schema, and the prescription fields 1212 store prescriptions for the prescription drug with the potential for abuse, misuse and/or diversion. The patient fields 1214 are contained within the database schema, and the patient fields 1214 store information sufficient to identify the patient for whom the prescription drug is prescribed. The caregiver fields 1216 are contained within the database schema, and the caregiver fields 1216 store information sufficient to identify a caregiver who is associated with the patient. The prescriber fields 1218 are contained within the database schema, and the prescriber fields 1218 store information sufficient to identify a physician or other prescriber of the prescription drug and information to show that the physician or other prescriber is authorized to prescribe the prescription drug.

The embodiments of FIGS. 12A and 12B, at 1220, processes a database query that operates over all data related to the prescription fields, prescriber fields, patient fields, and caregiver fields, and at 1230, the system and method reconcile inventory of the prescription drug before the shipments for a day or other time period are sent by using the database query to identify information in the prescription fields, prescriber fields, patient fields, and caregiver fields. The database query and the reconciling inventory identify potential abuse, misuse, and/or diversion by the patient and/or the caregiver (1240). The system and method then, based on that identification of the potential abuse, misuse, and/or diversion, notify the physician, who is interrelated with the patient through the schema of the single computer database, about the potential abuse, misuse, and/or diversion. The physician can then take action to address the potential abuse, misuse, and/or diversion by contacting the patient and/or caregiver, or take other action to investigate the identified potential abuse, misuse, and/or diversion. In an embodiment, the inventory reconciliation is performed where current inventory is counted and reconciled with database quantities before shipments for a day or other time period are sent, and the system and method selectively block shipment of the prescription drug based on the inventory reconciliation.

In another embodiment, one or more database queries check for abuse, misuse, and/or diversion within the central computer database. Thereafter, a prescription is authorized for the prescription drug only if there is no record of incidents that indicate abuse, misuse, and/or diversion by the patient, caregiver, or prescriber. If there is a record of such incidents, the central computer database indicates that such incidents have been investigated, and the central computer database indicates that such incidents do not involve abuse, misuse, and/or diversion.

At 1221, the system and method process a second database query. The second database query identifies that the patient is a cash payer and identifies a physician that is interrelated with the patient through the schema of the single computer database. As noted at 1221A, the identification that the patient is a cash payer by the second database query is an indicator of potential abuse, misuse, and/or diversion by the patient and/or caregiver and is used to notify the physician that is interrelated with the patient through the schema of the single computer database.

Since payment for the prescription drug in cash may be an indication of a patient who does not want to leave a paper trail associated with the purchase of the prescription drug, payment in cash therefore may be indicative of a situation that could lead to abuse, misuse, and/or diversion of the prescription drug.

At 1241, the system and method selectively block shipment of the prescription drug to the patient and/or caregiver based upon the identification of potential abuse, misuse, and/or diversion by the database query. In the alternative, at 1241A, if no abuse, misuse, and/or diversion is found by the patient or caregiver via the database query, the prescription drug is shipped to the patient and/or caregiver.

As indicated at 1211, the single computer database is an exclusive database that receives data associated with all patients being prescribed the prescription drug. And as indicated at 1211A, an exclusive central pharmacy controls the single computer database. As indicated at 1211B, the single computer database can be distributed among multiple computers. In such an embodiment, the database query that checks for potential abuse, misuse, and/or diversion of the prescription drug operates over all data relating to the prescription fields, prescriber fields, patient fields, and caregiver fields.

In an embodiment, the system and method initiate an inquiry to a prescriber when one or more prescription fields, patient fields, caregiver fields, or prescriber fields are incomplete in the computer database (1242). For example, when there is no caregiver associated with a pediatric patient, this can be considered an automatic potential abuse, misuse, and/or diversion situation that needs to not only be investigated but remedied as soon as possible (by identifying a caregiver who will be associated with the pediatric patient).

At 1221B, the system and method process a third database query that identifies an expected date for a refill of the prescription drug. The expected date is based on a prescription for the prescription drug and a date of a previous filling of the prescription. The prescription identifies an amount of the prescription drug to be provided and a schedule for consumption of the prescription drug. The system and method, via the third database query, can predict when a refill should occur, and if an attempt is made to refill the prescription before the anticipated refill date, the attempted refill can be questioned. It is noted that such an early refill attempt may be quite legitimate. For example, a patient may be going on an extended trip, and the prescription needs to be refilled before the trip.

At 1243, the system and method use the single computer database to identify a current pattern or an anticipated pattern of abuse of the prescription drug. The current pattern or the anticipated pattern is identified using periodic reports generated on a regular basis from the single computer database. The term regular basis means that the reports are generated at equally spaced time intervals, and not sporadically such as after a situation of abuse, misuse, and/or diversion has been identified. In this embodiment, one or more controls for distribution of the prescription drug are selected based on the identified pattern, and the one or more controls are submitted to an approval body for approval of distribution of the prescription drug.

At 1244, the current inventory is cycle counted and reconciled with database quantities before shipments for a day or other time period are sent.

At 1211C, the single computer database is an exclusive computer database of a company that obtained approval for distribution of the prescription drug. In this embodiment, all prescriptions for the company's prescription drug are stored only in the exclusive computer database of the company. The company's prescription drug is sold or distributed by the company using only the exclusive computer database of the company. The control of this embodiment exerted by the presence of the company's exclusive computer database further lends to the prevention of any potential abuse, misuse, and/or diversion of the prescription drug. The exclusive computer database of the company that obtained approval for distribution of the prescription drug is the only database in existence for the company's prescription drug, such that all prescriptions for the company's prescription drug are processed only by the exclusive computer database of the company.

In yet another embodiment wherein the single computer database is a single computer database of a company that obtained approval for distribution of the prescription drug, the prescription fields store all prescription requests, for all patients being prescribed the company's prescription drug, only in the single computer database of the company, from all physicians or other prescribers allowed to prescribe the company's prescription drug, such that all prescriptions for the company's prescription drug are processed using only the single computer database of the company (1211D).

In yet another embodiment, the exclusive computer database is associated with an exclusive central pharmacy, and not owned by the company that gained approval to distribute the prescription drug. In this situation, the inventory of the prescription drug is owned by the company, but the inventory is consigned to the exclusive central pharmacy and managed by the exclusive central pharmacy (1211E). This can be considered a hybrid embodiment.

As can be inferred and seen from the foregoing, a system to control the distribution of a prescription drug, which can be referred to as a Risk Evaluation and Mitigation Strategy (REMS) Program, has a goal of mitigating the risks of serious adverse outcomes resulting from inappropriate prescribing, misuse, abuse, and/or diversion of the prescription drug. This goal is achieved by (1) informing prescribers, pharmacists, patients, and caregivers of the risks, contraindications, potential for abuse, misuse, diversion, and/or overdose, and the safe use, handling, and storage of the prescription drug, and (2) ensuring that pharmacy controls exist prior to filling prescriptions that screen for concomitant use of potentially interacting agents, monitoring for inappropriate prescribing, and monitoring and notifying prescribers about concomitant use of contraindicated medications or signs of potential abuse, misuse, and/or diversion.

When prescribing prescription drugs, which have the potential for abuse, misuse, and/or diversion, to pediatric patients, caregivers are critical for many aspects of safe prescribing and use, even though such caregivers have not been considered formal stakeholders in prior pediatric programs. Nevertheless, as noted above, for pediatric patients, a distribution program includes a mandatory responsible adult caregiver as a condition of safe use for each patient. The pediatric REMS system ensures that caregivers of pediatric patients are counseled on the serious risks and safe use of the prescription drug. Medication guides and other material have information to ensure that these tools are relevant to both adult and pediatric patient groups. Counseling and attestation forms and other resources such as the quick start guide, medication guide, and caregiver brochure are also helpful for caregivers. Finally, certain central certified pharmacy material, training, and processes ensures the consistent implementation of a pediatric REMS program for all pediatric patients.

A responsible adult caregiver can be critical for many aspects of safe prescribing of sensitive drugs and use in pediatric patients (or elderly or other special needs patients). To implement this, caregivers should be included as formal stakeholders of a REMS Program. Several features are useful in making a caregiver a formal stakeholder. Prescribers and pharmacists should be formally required to counsel caregivers. If such counseling is not required, caregivers will not be apprised of the serious risks, how to safely use a prescription drug, how to safely handle a prescription drug, and how to safely store a prescription drug prior to initiating therapy.

Also, caregivers should formally be required to maintain responsibility for aspects of the safe prescribing, use, handling, and storage of the prescription drug, so that such caregivers can consistently maintain responsibility for these aspects. These responsibilities include notifying healthcare professionals immediately of possible serious adverse reactions associated with the prescription drug, ensuring compliance with contraindications (for example, alcohol and sedative hypnotics) and avoidance of concomitant use of the prescription drug with other potentially interacting agents, adherence to preparation and dosing instructions, adherence to not allowing a pediatric patient (or elderly or other special needs patient) to operate hazardous machinery, including automobiles, for a specified time period after taking a dose of the prescription drug until the caregiver knows how the prescription drug affects the patient, and adhering to safe use, handling, and storage procedures for the prescription drug. It should be noted, that in an embodiment, caregivers are required to educate each adult who may be assigned caregiver responsibilities, so that there is a consistency in educating each adult who may be assigned temporary responsibility (interim caregiver) for one or more components of safe use procedures (for example, the preparation, administration, safe use, handling, and storage of the prescription drug).

When prescriptions come into the exclusive central pharmacy, central certified pharmacy personnel can remind the prescribers that one has to be properly certified to write a prescription for the prescription drug. That is, the prescriber can be reminded by the central pharmacy personnel that the prescriber must have been properly educated on the pertinent REMS program requirements as they relate to the pediatric population.

The central certified pharmacy personnel should consistently ensure that the prescription drug is dispensed only to pediatric patients with an associated responsible adult caregiver who has been counseled on the serious risks and safe use of the prescription drug. Central certified pharmacy personnel should have official material and processes regarding dispensing the prescription drug to pediatric patients and should be trained on informal processes that have evolved for dispensing the prescription drug to pediatric patients. A central certified pharmacy patient/caregiver counseling checklist should adequately and consistently achieve its objectives in the pediatric population - - - that is proper education, distribution, storage, and usage of the prescription drug in the patient population.

In summary, an embodiment of a pediatric REMS program ensures that the prescription drug is shipped only to pediatric patients enrolled in the REMS program, and only to those pediatric patients with an associated caregiver with documented counseling and attestations. An exclusive central database includes REMS program caregiver counseling and attestation forms and REMS program patient/caregiver counseling checklists.

Another embodiment of the present drug distribution system includes the use of a device to facilitate the administration and tracking of a medication. For example, U.S. Pat. No. 9,801,852, which is incorporated herein by reference, discloses a dispensing device that facilitates and controls the use of a medication. The medication facilitated and controlled by the dispensing device can be in liquid or solid form. The present drug distribution system may facilitate controlled distribution of the dispensing device coupled with detection of the proper use of the medication by the authorized patient. The device allows for accurate dispensing of a medication, such as oxybate, under controlled conditions. In some embodiments there are optional features that can enhance the secure distribution or administration of the medication. In one embodiment, the dispenser is used with a medication, such as oxybate, without any additional security features, like a formulation change with an aversive for example.

A dispensing device, such as the device disclosed in U.S. Pat. No. 9,801,852, can include two compartments. A first compartment can include a product bag configured to hold the product (medication or prescription drug) and a treatment stack configured to treat the product. A second compartment can include a treatment reservoir configured to hold the treated product, a water reservoir configured to retain/supply water for dilution, a mixer configured to generate a diluted dose of the treated product, and a dilution vessel configured to hold the diluted product. The second compartment can additionally include a dose receiver for receiving a dose of the diluted product. In another embodiment, the first compartment simply holds multiple doses of the product, and the second compartment is configured to receive a single dosage of the product from the first compartment and make the single dosage available to a patient.

The dispensing device can also include a controller configured to control operation of the dispensing device. In some embodiments, the controller can include at least a processor and a memory. The controller can further include an input/output interface I/O that can encompass, but is not limited to, interfaces for network connectivity (wired/wireless, including Bluetooth), a display unit, input interfaces (such as selectable keys, a touchscreen, a control panel, and/or the like) for use by the user, and/or the like.

In some embodiments, the controller can optionally include a database for storing information including, but not limited to, patient information, dosing information, compliance information, and/or the like. In some embodiments, the controller can optionally include one or more locks to limit access to and/or use of the dispensing device. The locks can encompass hardware-based lockout mechanisms (e.g., a physical lock, a coded latch, and/or the like) as well as software-based lockout approaches (e.g., password and/or pin-based authentication). In some embodiments, the controller can optionally include one or more indicators for communicating with a user such as, for example a visual indicator (e.g., an LED), an audible indicator (e.g., a beeping sound), a graphic indicator (e.g., an icon), and/or the like. It is understood that the various illustrated components of the controller need not be mutually exclusive: for example, the lock can include password-based authentication that is based on instructions stored in the memory and executed by the processor.

In an embodiment, the processor of the dispenser can communicate with a REMS (Risk Evaluation and Management Strategy) system such as via the computer system 100 of FIG. 1, the eBook of FIG. 13, and/or some other component of a REMS system. This exchange can include the REMS system logging any data captured by the dispenser, and the dispenser storing any data and/or executing any instructions from the REMS system. The communication can also include a registration of the drug dispensing device by the patient, and a tracking of usage of the drug dispensing device by the patient, thereby also tracking usage of prescription drug by the patient.

For example, the REMS computer system 100 of FIG. 1 could transmit signals to the dispenser to control any locking mechanism on the dispenser (thereby controlling when a dose can be administered), prescription and/or dosing information that can be stored in the memory or database of the dispenser, and/or control the indicator of the dispenser. Similarly, the dispenser could transmit to the REMS computer system 100 of FIG. 1 when the locking mechanism is engaged or disengaged, and/or when a dosage is prepared and/or dispensed. Additionally, the REMS system and the dispenser can communicate regarding prescription refills of the dispenser. For example, the REMS system can communicate to the dispenser that a patient should be refilling the dispenser within a particular time period, perhaps in a day or two. Thereafter, sensors in the dispenser can transmit a signal back to the REMS when the dispenser is refilled. Such sensors can include a sensor that detects the full weight of a new prescription refill, a signal that a compartment that contains the prescription has been opened and then closed, etc. The dispenser can also transmit to the REMS system that a refill has not been added to the dispenser, such as after the time period in which the REMS system informed the dispenser that a refill should have been added. As another example, the dispenser may have a scale or other sensing device, and the sensor can signal to the REMS system that a refill will soon be needed. The REMS system can then check its database to determine if such a refill would be too soon, and an investigation could be launched to look into the reasons why the dispenser is unexpectedly low on the prescription.

More specifically, in connection with controlling access to dosages and/or monitoring refills, the REMS system can transmit to the processor and the database of the dispenser the dates and times of day during which a dosage can be made available, and cause the indicator to become illuminated signaling to a patient that a dose can be prepared, received, and/or administered. This programming can be implemented by the prescriber, and can be modified as need be (such as after a doctor office visit or after a patient has spilled or lost a prescription). This programming assures that the pharmaceutical is made ready for consumption only when a patient is supposed to take the pharmaceutical. Likewise, the dispenser can communicate back to the REMS system a confirmation that the pharmaceutical has been properly removed from the dispenser.

The pharmaceutical can be stored in an internal reservoir of the dispenser and await usage by the patient. In an embodiment, the REMS system and/or the dispenser processor can control when a dosage is removed from the product container and placed in the internal reservoir for access by the patient. This internal reservoir can be secured by a physical lock, such as an electromagnetic lock, and this electromagnetic lock can be controlled by the dispenser processor and/or the REMS processor 100. If controlled by the dispenser processor, data relating to the access of the pharmaceutical can be transmitted to and stored in the REMS system. The communication between the REMS system and the dispenser is preferably via wireless means, but can also occur via wired means (such as over telephone lines).

In an embodiment, an aversive or other objectionable compound can be added to the pharmaceutical and the dispenser can remove the objectionable compound before the pharmaceutical is ingested by the patient. The presence of an aversive in the pharmaceutical helps prevent abuse or misuse of the pharmaceutical.

The data that can be exchanged between the REMS system and the dispenser can relate to one or more of the following - - - information displayed on a REMS or dispenser display unit; information input into the dispenser by a patient; the number of doses taken per time period, the time for the next dose, and the actual time of dosage; data relating to any manual override of some control features of the dispenser (such as allowing for dispensing multiple doses for travel); the functioning of an indicator light on the dispenser that a lockout period has lapsed and that another dose can be dispensed; an alarm to wake the patient for a second dose administration; passive authentication such as with infrared emitting diode on a bracelet worn by the patient; active authentication such as with a pincode entered by the patient; accessing a keyed enclosure to the product; programming controls that govern frequency and amount of administration and dispensing events; indicators displaying amount of drug treated, dispensed, and/or remaining within the dispenser; programming changes either by plug-in chip or cartridge or by remote connection such as a wireless device; a service life timer or performance measurement and indicator that may prompt the patient to either send the unit for service or replace consumable elements such as filters; distribution of fluids from the different reservoirs; the amount of fluid from each reservoir; changes to the amount of each dose; and balance (e.g., weight of product remaining and/or dispensed) information when a pharmaceutical is measured out by the dispenser.

It should be understood that there exist implementations of other variations and modifications of the invention and its various aspects, as may be readily apparent, for example, to those of ordinary skill in the art, and that the invention is not limited by specific embodiments described herein. Features and embodiments described above may be combined with each other in different combinations. It is therefore contemplated to cover any and all modifications, variations, combinations or equivalents that fall within the scope of the present invention.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate example embodiment.

The invention claimed is:

1. A system comprising:
an eBook comprising a physical brochure or book;
a computer processor embedded in the physical brochure or book;
a memory coupled to the computer processor; and
a drug dispensing device comprising a device computer processor and a locking mechanism;
wherein the memory comprises:
educational material relating to a prescription drug that has a potential for abuse;
a test section for testing whether a patient and a caregiver associated with the patient have read and understood material in the eBook; and
links for navigating through the eBook;
wherein the computer processor of the eBook is operable to:
receive input from the patient or the caregiver, the input for one or more of causing a display of the educational material, invoking the links for navigating through the eBook, and invoking the test section;
automatically confirm using the computer processor of the eBook that the patient or the caregiver has opened the eBook, and transmit using the computer processor of the eBook to an exclusive computer database a confirmation that the patient or the caregiver has opened the eBook;
determine that a score on the test section by the patient or the caregiver exceeds a threshold; and
transmit the score to the exclusive computer database for processing and determining whether the patient should be prescribed the prescription drug;
wherein the eBook is operable to receive input from the caregiver associated with the patient, the input related to a selection of particular content for the patient;
wherein the selection of the particular content comprises a selection of the particular content related to the patient of a first age or the selection of the particular content related to the patient of a second age;
wherein the computer processor of the eBook is operable to ensure that the patient or the caregiver has reviewed the educational material from a beginning of the eBook to an end of the eBook in sequential order and to permit the patient or the caregiver free movement throughout the eBook after the patient or the caregiver has completed review of the eBook in the sequential order; and
wherein the computer processor of the eBook is operable to communicate with the device computer processor; wherein the computer processor of the eBook transmits a signal to the device computer processor relating to the locking mechanism on the drug dispensing device; and wherein the drug dispensing device operates the locking mechanism based on the signal received from the computer processor of the eBook.

2. The system of claim 1,
wherein the prescription drug is distributed under exclusive control of an exclusive central pharmacy;
wherein all prescription requests, from any and all medical doctors allowed to prescribe the prescription drug, for any and all patients being prescribed the prescription drug, are received only at the exclusive central pharmacy, the prescription requests containing information identifying patients, patient caregivers, the prescription drug, and various credentials of the any and all medical doctors;
wherein the exclusive computer database is under control of the exclusive central pharmacy;
wherein an exclusive central pharmacy processor is operable to require entering of the information into the exclusive computer database for analysis of potential abuse situations, such that all prescriptions for the prescription drug are processed only by the exclusive central pharmacy using only the exclusive computer database;
wherein the exclusive central pharmacy processor is operable to check the credentials of the any and all medical doctors to determine the eligibility of the medical doctors to prescribe the prescription drug;
wherein the exclusive central pharmacy processor is operable to receive the test score from the eBook;
wherein the exclusive central pharmacy processor is operable to determine via the test score that the patient or the caregiver has read and understood the educational material in the eBook prior to shipping the prescription drug;
wherein the exclusive central pharmacy processor is operable to check the exclusive computer database for potential abuse of the prescription drug;
wherein the exclusive central pharmacy processor is operable to mail the prescription drug to the patient or the caregiver only if no potential abuse is found by the patient to whom the prescription drug is prescribed, the caregiver associated with the patient, and the medical doctor prescribing the prescription drug;
wherein the exclusive central pharmacy processor is operable to confirm receipt of the prescription drug by the patient or the caregiver; and
wherein the exclusive central pharmacy processor is operable to generate using the exclusive computer database periodic reports on a regular time basis to evaluate potential diversion patterns.

3. The system of claim 1, wherein the eBook comprises different content for different types of patients including patients of different ages.

4. The system of claim 1, wherein the eBook is operable to calculate a titration or dosage for the patient, and to display the dosage or titration on an electronic display of the eBook.

5. The system of claim 1, wherein the eBook is operable to remind the patient and caregiver associated with the patient of an upcoming refill; to receive a refill request from the patient or the caregiver associated with the patient; and to transmit the refill request only to an exclusive central pharmacy.

6. The system of claim 1, wherein the eBook is operable to receive input from the patient or the caregiver associated with the patient to register with an exclusive central pharmacy to receive the prescription drug and to transmit the input to a medical doctor for registering the patient with the exclusive central pharmacy; and to receive input from the patient or caregiver associated with the patient to modify patient information or caregiver information.

7. The system of claim 1, wherein the eBook is configured to receive input from the patient and/or the caregiver associated with the patient, the input notifying an exclusive central pharmacy of possible adverse reactions associated with the prescription drug.

8. The system of claim 1, comprising a patient survey or a caregiver survey.

9. The system of claim 1, wherein the computer processor of the eBook is operable to communicate with the device computer processor, wherein the computer processor of the eBook and the device computer processor exchange data relating to the educational material, the test section, the score on the test section, and the links for navigating through the eBook.

10. The system of claim 9, wherein the computer processor of the eBook and the device computer processor exchange data relating to prescriptions, the prescription drug, the patient, the caregiver, physicians, prescribers, and database queries of the exclusive computer database relating to abuse, misuse, or diversion of the prescription drug; and wherein the drug dispensing device dispenses the prescription drug to the patient when the database query indicates that there is no abuse, misuse, or diversion of the prescription drug.

11. The system of claim 9, wherein the computer processor of the eBook and the device computer processor exchange data relating to a registration of the drug dispensing device by the patient, and a tracking of usage of the drug dispensing device by the patient.

12. The system of claim 1, wherein the computer processor of the eBook is operable to communicate with the device computer processor; wherein the device computer processor senses when a prescription has been refilled; and wherein the device computer processor transmits to the eBook an indication that the prescription has been refilled.

13. The system of claim 1, wherein the computer processor of the eBook is operable to communicate with the device computer processor; wherein the computer processor of the eBook transmits a signal to the device computer processor informing the drug dispensing device that the prescription drug should be made available to the patient; wherein the device computer processor makes the prescription drug available to the patient based on the signal received from the computer processor of the eBook; and wherein the device computer processor informs the eBook that the prescription drug has be dispensed.

14. The system of claim 1, wherein the computer processor of the eBook is operable to communicate with the device computer processor; and wherein the computer processor of the eBook transmits a signal to the device computer processor causing the drug dispensing device to sound an alarm to remind or wake the patient to take a dose of the prescription drug.

15. The system of claim 1, wherein the patient and the caregiver are different persons.

* * * * *

UNITED STATES PATENT AND TRADEMARK OFFICE
CERTIFICATE OF CORRECTION

PATENT NO. : 11,456,081 B1
APPLICATION NO. : 16/032501
DATED : September 27, 2022
INVENTOR(S) : Lillaney et al.

Page 1 of 2

It is certified that error appears in the above-identified patent and that said Letters Patent is hereby corrected as shown below:

On the Title Page

On page 2, in Column 2, under "Other Publications", Line 2, delete "Adminstration," and insert --Administration,-- therefor On page 2, in Column 2, under "Other Publications", Line 5, delete "Commettees:" and insert --Committees:-- therefor On page 4, in Column 2, under "Other Publications", Line 7, delete "14/219,941,Response" and insert --14/219,941, Response-- therefor On page 6, in Column 2, under "Other Publications", Line 34, delete "(Jazz:" and insert --(Jazz-- therefor On page 7, in Column 2, under "Other Publications", Line 13, delete "inital" and insert --Initial-- therefor On page 7, in Column 2, under "Other Publications", Line 16, delete "Inital" and insert --Initial-- therefor On page 7, in Column 2, under "Other Publications", Line 27, delete "Sodilum" and insert --Sodium-- therefor On page 7, in Column 2, under "Other Publications", Line 30, delete "Sodilum" and insert --Sodium-- therefor On page 7, in Column 2, under "Other Publications", Line 57, delete "Pharmaceautical," and insert --Pharmaceutical,-- therefor Signed and Sealed this
Twenty-seventh Day of December, 2022

Katherine Kelly Vidal
*Director of the United States Patent and Trademark Office*

CERTIFICATE OF CORRECTION (continued)
U.S. Pat. No. 11,456,081 B1

On page 7, in Column 2, under "Other Publications", Line 59, delete "*Pharmaceauticals,*" and insert --*Pharmaceuticals,*-- therefor On page 7, in Column 2, under "Other Publications", Line 59, delete "*Parmaceutical,*" and insert --*Pharmaceutical,*-- therefor On page 7, in Column 2, under "Other Publications", Line 60, delete "*Pharmaceauticals,*" and insert --*Pharmaceuticals,*-- therefor On page 8, in Column 2, under "Other Publications", Line 61, delete "*Pharmaceauticals,*" and insert --*Pharmaceuticals,*-- therefor On page 8, in Column 2, under "Other Publications", Line 65, delete "*Pharmaceauticals,*" and insert --*Pharmaceuticals,*-- therefor On page 9, in Column 1, under "Other Publications", Line 60, delete "7,765,106 0"," and insert --7,765,106",-- therefor On page 9, in Column 1, under "Other Publications", Line 65, delete "Exhibit." and insert --Exhibit-- therefor On page 10, in Column 1, under "Other Publications", Line 42, delete "Appeall" and insert --Appeal-- therefor On page 10, in Column 1, under "Other Publications", Line 45, delete ""Workhardt" and insert --"Wockhardt-- therefor On page 10, in Column 1, under "Other Publications", Line 51, delete "Applicaitons" and insert --Applications-- therefor On page 12, in Column 1, under "Other Publications", Line 7, delete "FileHistory" and insert --File History-- therefor In the Specification In Column 1, Line 44, delete "buterate" and insert --butyrate-- therefor In Column 22, Line 23, after "database.", delete a linebreak